US011262340B2

(12) United States Patent
Chiu et al.

(10) Patent No.: US 11,262,340 B2
(45) Date of Patent: Mar. 1, 2022

(54) MULTI-SENSOR GAS SAMPLING DETECTION SYSTEM FOR RADICAL GASES AND SHORT-LIVED MOLECULES AND METHOD OF USE

(71) Applicant: MKS Instruments, Andover, MA (US)

(72) Inventors: Johannes Chiu, Bedford, MA (US);
Xing Chen, Lexington, MA (US);
Chiu-Ying Tai, Chelmsford, MA (US);
Michael Harris, Hudson, MA (US);
Atul Gupta, Lexington, MA (US)

(73) Assignee: MKS Instruments, Inc., Andover, MA (US)

( * ) Notice: Subject to any disclaimer, the term of this patent is extended or adjusted under 35 U.S.C. 154(b) by 208 days.

(21) Appl. No.: 16/205,064

(22) Filed: Nov. 29, 2018

(65) Prior Publication Data

US 2019/0170715 A1    Jun. 6, 2019

Related U.S. Application Data

(60) Provisional application No. 62/593,721, filed on Dec. 1, 2017, provisional application No. 62/646,867, filed on Mar. 22, 2018.

(51) Int. Cl.
*G01N 33/00* (2006.01)
*G01K 17/06* (2006.01)
(Continued)

(52) U.S. Cl.
CPC ......... *G01N 33/0031* (2013.01); *G01K 17/06* (2013.01); *G01N 21/3504* (2013.01); *G01N 27/122* (2013.01); *G01N 33/0016* (2013.01)

(58) Field of Classification Search
None
See application file for complete search history.

(56) References Cited

U.S. PATENT DOCUMENTS 3,718,437 A    2/1973  Paloniemi
4,333,735 A    6/1982  Hardy et al.
(Continued)

FOREIGN PATENT DOCUMENTS

CN    101023199 A    8/2007
CN    100350584 C    11/2007
(Continued)

OTHER PUBLICATIONS

Yuan, W. et al., Graphene-based gas sensors, Journal of Materials Chemistry A, 1, 10078-10091 (Year: 2013).*
(Continued)

*Primary Examiner* — Xiaoyun R Xu

(57) ABSTRACT

The present application is directed to a multi-sensor gas sampling detection system and method for detecting and measuring the radicals in a radical gas stream and includes at least one radical gas generator in communication with at least one gas source. The radical gas generator may be configured to generate at least one radical gas stream which may be used within a processing chamber. As such, the processing chamber is in fluid communication with the radical gas generator. At least one analysis circuit in fluid communication with the radical gas generator may be used in the detection and measurement system. The analysis may be configured to receive a defined volume and/or flow rate of the radical gas stream. In one embodiment, the analysis circuit may be configured to react at least one reagent with radicals within the defined volume of the radical gas stream thereby forming at least one chemical species within at least one compound stream. At least one sensor module within the analysis circuit may be configured to measure a concentration of the chemical species within the compound stream. One or more flow measurement modules may be in fluid communication with the sensor module. During use, the flow measurement module may be configured to measure the (Continued)

volume of at least one of the compound stream and radical gas stream.

7 Claims, 34 Drawing Sheets

(51) Int. Cl.
*G01N 27/12* (2006.01)
*G01N 21/3504* (2014.01)

(56) References Cited

U.S. PATENT DOCUMENTS

| | | | |
|---|---|---|---|
| 5,032,435 | A | 7/1991 | Biefeld et al. |
| 5,261,452 | A | 11/1993 | McAndrew et al. |
| 5,744,696 | A | 4/1998 | Wang et al. |
| 6,341,890 | B1 | 1/2002 | Vally et al. |
| 6,421,127 | B1 | 7/2002 | McAndrew et al. |
| 6,686,594 | B2 | 2/2004 | Ji et al. |
| 6,823,743 | B2 | 11/2004 | Sato et al. |
| 7,572,052 | B2 | 8/2009 | Ravi et al. |
| 7,651,269 | B2 | 1/2010 | Comendant |
| 7,691,204 | B2 | 4/2010 | Chacin et al. |
| 7,835,874 | B2 | 11/2010 | Wong et al. |
| 8,154,714 | B2 | 4/2012 | Furtaw et al. |
| 9,234,775 | B2 | 1/2016 | Larson et al. |
| 2002/0180991 | A1 | 12/2002 | Takoudis et al. |
| 2004/0084147 | A1* | 5/2004 | Dando ............ C23C 16/452 |
| | | | 156/345.29 |
| 2010/0022397 | A1 | 9/2010 | Boone et al. |
| 2017/0276527 | A1 | 9/2017 | Chen et al. |

FOREIGN PATENT DOCUMENTS

| | | |
|---|---|---|
| EP | 2075584 A1 | 7/2009 |
| JP | 2009-50085 A | 1/2009 |
| JP | 2012-088090 A | 5/2012 |
| JP | 2012088090 A | 5/2012 |
| WO | WO 88-04409 A1 | 6/1988 |
| WO | WO8804409 A1 | 6/1998 |

OTHER PUBLICATIONS

Kim, S., et al. Mid-Infrared Trace Gas Analysis with Single-Pass Fourier Transform Infrared Hollow Waveguide Gas Sensors, Applied Spectroscopy, 63(3), 331-337 (Year: 2009).*
The International Search Report dated Jul. 15, 2019 to PCT/US2018/063124, 5 pages.
The Written Opinion dated Jul. 15, 2019 to PCT/US2018/063124, 14 pages.
The Written Opinion dated Jun. 2, 2021 to Singapore application No. 11202006380U, 4 pages.

* cited by examiner

MULTI-SENSOR GAS SAMPLING DETECTION SYSTEM FOR RADICAL GASES AND SHORT-LIVED MOLECULES AND METHOD OF USE

CROSS-REFERENCE TO RELATED APPLICATIONS

The present application claims priority to U.S. Patent Application Ser. No. 62/593,721, filed on Dec. 1, 2017, entitled "Multi-Sensor Gas Sampling Detection System for Radical Gases and Short-Lived Molecules and Method of Use," and U.S. Patent Application Ser. No. 62/646,867, filed on Mar. 22, 2018, entitled "Multi-Sensor Gas Sampling Detection System for Radical Gases and Short-Lived Molecules and Method of Use," the contents both of which are hereby incorporated by reference in their entirety herein.

BACKGROUND

Electronic devices and systems are being incorporated into an ever-increasing number of device, systems, and applications. As a result, market demand for low-cost integrated circuits having increased complexity and diminished scale continues to grow. Various microfabrication processes such as radical-based semiconductor wafer processes have been developed to address scaling challenges. In order to design and manufacture a high performance integrated circuit cost-effectively, the parameters of the radical-based semiconductor wafer manufacturing process need to be carefully controlled.

Presently, a number of radical-based semiconductor wafer processing methods are in use. The radical gases used in the processes include atoms, excited molecules as well as many short-lived molecules that do not normally exist in a gas, such as H, O, N, F, Cl, Br, NH, $NH_2$, NF, CH, $CH_2$, COF, etc. While presently available radical-based semiconductor wafer processes have proven somewhat useful in the past a number of shortcomings have been identified. For example, the radical species generated during wafer processing are short-lived thereby making accurate measurement and analysis challenging. As a result, rather than relying on quantitative analysis, presently available radical-based semiconductor wafer manufacturing methodologies involve precise formulations and virtual metrology to achieve the desired wafer architecture. Any variation in the formulations and/or control processes may greatly affect production yield. In addition, the highly reactive radical species generated during wafer processing tend to quickly degrade analyzing devices and sensors, optical windows and components, and other systems or devices positioned within the radical stream or processing chamber.

Thus, in light of the foregoing, there is an ongoing need for a multi-sensor gas sampling detection system useful in radical-based semiconductor wafer processing.

SUMMARY

The present application is directed to a multi-sensor gas sampling detection system and method for detecting and measuring atomic radicals, molecular radicals, and/or short-lived molecules in a radical gas stream or similar gas stream. The detecting and measuring system may include at least one radical gas generator in communication with at least one gas source. The radical gas generator may be configured to generate at least one radical gas stream which may be used within a processing chamber. As such, the processing chamber is in fluid communication with the radical gas generator. At least one analysis circuit may be in fluid communication with the radical gas radical gas generator may be used in the detection and measurement system. The analysis circuit may be configured to receive a defined volume and/or flow rate of the radical gas stream. In one embodiment, the analysis circuit may be configured to react at least one reagent with the radical gases within the defined volume of the radical gas stream. The reaction produces at least one compound stream (or reaction products) from the radical gases and the at least one reagent, which may be in the form of a chemical species, charged particles, photon emission, or a thermal energy release, which may be measured by at least one sensor module within the analysis circuit. One or more flow measurement modules may be in fluid communication with the sensor module. During use, the flow measurement module may be configured to measure the volume and/or flow rate of at least one of the compound stream and radical gas stream. Based on the amount of reaction products measured and the volume and/or flow rate of the compound stream and the radical gas stream, the concentration or the amount of radical gases in the radical gas stream can be obtained.

The present application further discloses a method of measuring radical gases in a radical gas stream. More specifically, the method for measuring radicals in a gas stream includes providing at least one radical gas stream having radicals therein. A sampling gas stream may be created by directing a defined volume and/or flow rate of the radical gas stream to at least one sampling module. At least one reagent may be combined with the radicals within the sampling gas stream to form at least one compound stream having at least one chemical species therein. Thereafter, the concentration of the chemical species within the compound stream may be measured using at least one sensor module. Further, the remaining volume of the radical gas stream may be directed into at least one processing chamber. The flow rate of the radical gas stream and/or the compound gas stream may be measured using at least one flow measurement module in fluid communication with the sensor module. Finally, the concentration of radicals within the processing chamber may be calculated by comparing a ratio of the concentration of chemical species within the compound stream per defined volume of the radical gas stream forming the sampling gas stream to the remaining volume of the radical gas stream.

In another embodiment, the present application discloses a method of measuring radicals in a radical gas stream. The method includes providing at least one radical gas stream having radicals therein. At least one upstream gas stream may be formed by directing a defined volume of the radical gas stream to at least one upstream sampling module while directing the remaining volume of the radical gas stream into at least one processing chamber. At least one chamber sampling gas stream may be formed by directing a defined volume of the radical gas stream from the processing chamber to at least one chamber sampling module while a remaining volume of the radical gas stream within the processing chamber is exhausted therefrom thereby forming at least one exhaust gas stream. At least one exhaust sampling gas stream may be formed by directing a defined volume and/or flow rate of the exhaust gas stream to at least one exhaust sampling module. Thereafter, at least one reagent may be reacted with the radicals in the radical gas streams within at least one of the upstream sampling module, the chamber sampling module, and the exhaust sampling module to form at least one of an upstream compound stream, a chamber compound stream, and an exhaust compound stream at least one of which having at least one chemical species therein. The quantity of chemical species within at least one of the upstream compound stream, chamber compound stream, and exhaust compound stream compound stream may be measured and the concentration of radicals within the processing chamber may be calculated by comparing a ratio of the concentration of chemical species within at least one of the upstream compound stream, chamber compound stream, and exhaust compound stream per defined volume of the radical gas stream forming the upstream sampling gas stream, chamber sampling gas stream, and exhaust sampling gas stream to the remaining volume of the radical gas stream.

In addition, the present application discloses a multi-sensor gas detection system for use in a wafer processing system. The wafer processing system includes an upstream sampling module in fluid communication with a radical gas stream emitted from at least one source of radical gas source. The upstream sampling module may be configured to receive a controlled volume and/or flow rate of the radical gas stream from the radical gas source. At least one reagent is reacted with the controlled volume and/or flow rate of the radical gas stream to produce an upstream compound stream. Further, at least one chamber sampling module may be in fluid communication with the at least one radical gas stream present within at least one processing chamber. The chamber sampling module may be configured to receive a controlled volume and/or flow rate of the radical gas stream and react with the controlled volume and/or flow rate of the radical gas stream with at least one reagent to produce a chamber compound stream. In addition, at least one exhaust sampling module may be in fluid communication with the radical gas stream exhausted from the processing chamber. The exhaust sampling module may be configured to receive a controlled volume and/or flow rate of the radical gas stream and react with the controlled volume of the radical gas stream with at least one reagent to produce an exhaust compound stream. At least one sensor module may be communication with at least one of the upstream sampling module, chamber sampling module, and exhaust sampling module. The sensor module may be configured to measure the concentration of at least one of the upstream compound stream, chamber compound stream, and exhaust compound stream. At least one flow module may be in communication with at least one of the upstream sampling module, chamber sampling module, exhaust sampling module, and sensor module. The flow module may be configured to control the flow rate of at least one of the upstream compound stream, chamber compound stream, and exhaust compound stream.

The present application also discloses a sampling reaction module for use in a reactive gas processing system. The sampling reaction module may include at least one analysis fixture having an analysis fixture body. The analysis fixture body defines at least one fluid channel therein. At least one fluid inlet port and fluid outlet port may be formed in the analysis fixture body. The inlet port and outlet port may be in fluid communication with the fluid channel formed in the analysis fixture body. At least one coupling body extends from the analysis fixture body. In one embodiment, the coupling body includes at least one coupling passage formed therein. At least one sampling tube traversing through the analysis fixture body may be positioned within the coupling passage of the coupling body. Further, at least one module body defining at least one vacuum passage therein configured to receive at least one analysis fixture body thereon may be included in the sampling reaction module. The module body may have at least one sampling tube receiver formed therein such that the sampling tube receiver may be in fluid communication with the vacuum passage.

Lastly, the present application further discloses a calorimetry system. More specifically, the calorimetry system includes at least one reactive gas conduit defining at least one gas passage therein. During use, the gas passage is configured to have at least one reactive gas flowed therethrough. Further, at least a first sensor body may be positioned within the gas passage of the reactive gas conduit. In one embodiment, the sensor body is configured to measure a temperature of the reactive gas flowed through the gas passage. In addition, at least one sensor device may be in communication with the sensor body. During use, the at sensor device may be configured to receive temperature data relating to the reactive gas flow from the sensor body. At least one processor may be in communication with the first sensor device and may be configured to calculate a sample power of the reactive gas flowing through the reactive gas conduit.

Other features and advantages of the multi-sensor gas sampling detection system and method for detecting and measuring the radicals in a radical gas stream as described herein will become more apparent from a consideration of the following detailed description.

BRIEF DESCRIPTION OF THE DRAWINGS

The novel aspects of the multi-sensor gas sampling detection system and method for detecting and measuring the radicals in a radical gas stream as disclosed herein will be more apparent by review of the following figures, wherein.

DETAILED DESCRIPTION

The present application is directed to a multi-sensor gas sampling detection system for atomic radicals, molecular radicals, and short-lived molecules (hereinafter radicals) and method of use. More specifically, the present application discloses a gas sampling detection system configured to permit the user to easily and accurately measure the concentration of radicals in a gas stream. In one embodiment the gas sampling detection system disclosed herein may be configured to measure the concentration of radicals within a gas stream before introducing the gas stream into a processing chamber or similar vessel. In another embodiment, the gas sampling detection system disclosed herein may be configured to measure the concentration of radicals within a gas stream within the processing chamber or vessel. Optionally, the gas sampling detection systems disclosed herein may be used to measure the concentration of radicals within an exhaust stream, the exhaust stream being evacuated from the processing chamber or vessel. More specifically, the methods disclosed herein allow for measurement of the concentration of heretofore difficult-to-measure radicals by reacting the radicals within a gas sample with selected elements and compounds to create chemical species which can be easily and accurately detected and measured using a variety of measuring techniques. In some embodiments, the measurement process may be conducted in situ. Optionally, the measurement process may be conducted at a remote location.

Figure 1:
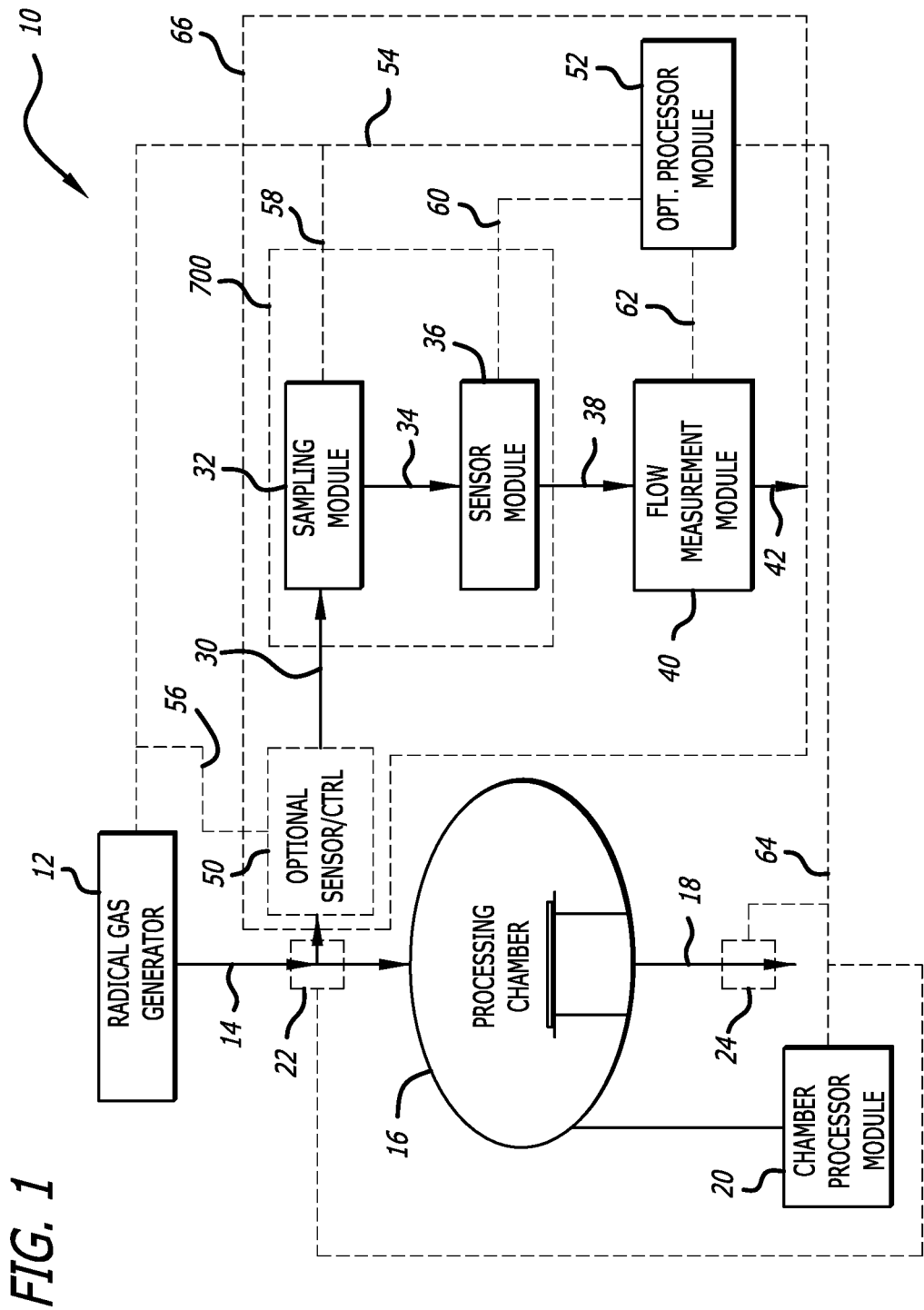
FIG. 1 shows a schematic diagram of an embodiment of a multi-sensor gas sampling detection system.

FIG. 1 shows schematically an embodiment of a gas sampling detection system useful for detecting the concentration of radicals within a gas stream. As shown, the gas sampling detection system 10 includes at least one plasma generator and/or radical gas generator 12 in fluid communication with at least one processing chamber 16 via at least one gas passage 14. In one embodiment, the radical gas generator 12 may include or may be in communication with at least one sample gas source and at least one plasma source. During use, the radical gas generator 12 may be configured to energize and dissociate sample gases and generate at least one reactive gas stream. In one specific embodiment the radical gas generator 12 comprises a RF toroidal plasma source, although those skilled in the art will appreciate that any variety of plasma sources or radical gas sources may be used with the present systems. In one embodiment the radical gas generator 12 uses hydrogen ($H_2$)

plasma to create atomic hydrogen. In another embodiment the radical gas generator 12 utilizes oxygen ($O_2$) plasma to create atomic oxygen. Optionally, the radical gas generator 12 may utilize nitrogen trifluoride ($NF_3$), fluorine ($F_2$), chlorine ($Cl_2$) or any variety of other materials to create a reactive plasma containing one or more radicals within the gas stream. Alternatively, radical gases may be generated by other gas excitation methods, including electron beam excitation, laser excitation, or hot-filament excitation. Further, the above description discloses various embodiments of RF-based plasma generation systems; although those skilled in the art will appreciate that any variety of alternate radical gas generation systems may be used with the present system. Exemplary alternate radical gas generation systems include, without limitation, glow discharge plasma systems, capacitively coupled plasma systems, cascade art plasma systems, inductively coupled plasma systems, wave heated plasma systems, arc discharge plasma systems, coronal discharge plasma systems, dielectric barrier discharge systems, capacitive discharge systems, Piezoelectric direct discharge plasma systems, and the like.

Referring again to FIG. 1, at least one processing chamber 16 may be in fluid communication with the radical gas generator 12 via at least one reactive gas conduit 14. In some applications, the reactive gas conduit 14 is manufactured from a chemically inert material or a material having low chemical reactivity. Exemplary materials include, without limitation, quartz, sapphire, stainless steel, strengthened steel, aluminum, ceramic materials, glass, brass, nickel, $Y_2O_3$, $YAlO_x$, various alloys, and coated metals such as anodized aluminum. In one embodiment a single reactive gas conduit 14 is in fluid communication with a single radical gas generator 12. In another embodiment multiple reactive gas conduits 14 are in fluid communication with a single reactive gas generator 12. In yet another embodiment a single reactive gas conduit 14 is in communication with multiple radical gas generators 12. As such, any number of reactive gas conduits 14 may be in communication with any number of radical gas generators 12. Optionally, the reactive gas conduit 14 may include one or more valve devices or systems, sensors, or similar devices 22 coupled thereto or in communication there with. For example, one or more valve devices 22 may be coupled to the reactive gas conduit 14 thereby permitting a user to selectively permit and/or restrict the flow of at least one reactive gas stream through the reactive gas conduit 14.

As shown in FIG. 1, the processing chamber 16 may be coupled to or in communication with the radical gas generator 12 via the reactive gas conduit 14. In one embodiment, the processing chamber 16 comprises one or more vacuum chambers or vessels configured to have one or more substrates, semiconductor wafers, or similar materials positioned therein. For example, the processing chamber 16 may be used for atomic layer processing of semiconductor substrates or wafers. Optionally, the processing chamber 16 may be used for processing any variety of substrates or materials using any variety of processing methods and/or systems. Exemplary processing methods include, without limitation, physical vapor deposition (PVD), chemical vapor deposition (CVD), rapid thermal chemical vapor deposition (RTCVD), atomic layer deposition (ALD), atomic layer etching (ALE), and the like. Those skilled in the art will appreciate that the processing chamber 16 be manufactured from any variety of materials, including, without limitation, stainless steel, aluminum, mild steel, brass, high-density ceramics, glass, acrylic, and the like. For example, at least one interior surface of the processing chamber 16 may include at least one coating, anodized material, sacrificial material, physical feature or element, and the like intended to selectively vary the reactivity, durability, and/or fill micro-pores on the interior surfaces of the processing chamber 16. At least one exhaust conduit 18 may be coupled to the processing chamber 16 and configured to evacuate one or more gases or materials from the processing chamber 16. Optionally, one or more control sensors, valves, scrubbers, or similar devices 24 may be coupled to or positioned proximate to the exhaust conduit 18, thereby permitting the user to selectively evacuate one or more gases or other materials from the processing chamber 16.

Referring again to FIG. 1, at least one chamber processor module 20 may be coupled to or otherwise in communication with the processing chamber 16 and/or various components of the processing system. The chamber processing module 20 may be configured to provide localized control of the various components forming the processing system 10. In the illustrated embodiment the chamber processing module 20 is in communication with the processing chamber 16 via a conduit, although those skilled in your will appreciate that the chamber processing module 20 may communicate with any of the components forming the processing system 10 via conduit, wirelessly, or both.

As shown in FIG. 1, at least one sampling module 32 may be in fluid communication with the radical gas generator 12 via at least one sampling conduit 30. Those skilled in the art will appreciate that the sampling conduit 30 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, in some embodiments the sampling conduit 30 may be configured to chemically react with the highly reactive atomic radicals, molecular radicals, and short-lived molecules contained within the radical gas stream flowing therein. In yet another embodiment, the sampling conduit 30 may consist of a catalytic material to facilitate the recombination of atomic gas species into its molecular gas species, such that the recombination energy of the atomic gas is released and measured. In other embodiments, the sampling conduit 30 may be configured to be chemically inert. Optionally, the sampling conduit 30 may include any variety of sensors, valves, heating elements, cooling elements, and the like thereon. In one embodiment, the sampling conduit 30 is coupled directly to and in fluid communication with the radical gas generator 12. In the illustrated embodiment the sampling conduit 30 is in fluid communication with the radical gas generator 12 via the reactive gas conduit 14. Optionally, the sampling conduit 30 may be in fluid communication with the sampling control valve 22 positioned on the reactive gas conduit 14. For example, the sampling control valve 22 may be configured to selectively direct a prescribed volume of reactive gas traversing through the reactive gas conduit 14 to the sampling module 32 via the sampling conduit 30. In another embodiment, the sampling control valve 22 may be configured to selectively direct a prescribed flow rate of reactive gas traversing through the reactive gas conduit 14 to the sampling module 32 via the sampling conduit 30. Further, any number of additional components, valves, sensors, and the like may be positioned anywhere along the sampling conduit 30. For example, in the illustrated embodiment at least one sensor and/or control device 50 may be positioned along the sampling conduit 30. Exemplary sensor devices include, without limitations, thermocouples, temperature sensors, optical sensors, UV, optical or infrared spectrometers, charge particle detectors, vacuum gauges, mass spectrometers, and the like. For example, in one embodiment the sensor device 50 comprises at least one thermistor. In another embodiment the sensor device 50 comprises at least one calorimetry system or device. An embodiment of a novel calorimetry system is discussed in detail and shown in FIGS. 8-15 of the present application. Optionally, the sensor device 50 may comprise one or more titration systems or devices. Those skilled in the arts will appreciate the sensor device 50 may comprise any number of in situ measuring devices were systems, flow valves, flowmeters, flow verifiers, and the like.

Referring again to FIG. 1, in the illustrated embodiment the sampling module 32 is coupled to at least one molecular compound stream conduit 34. Like the sampling conduit 30 the molecular compound stream conduit 34 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. In one embodiment at least a portion of at least one of the sampling conduit 30 and/or the molecular compound stream conduit 34 may be configured to react with the radical gas stream flowing therein. For example, one embodiment at least a portion of the sampling conduit 30 and/or molecular compound stream conduit 34 may be configured to react with radicals within the gas flow to form chemical species more stable and capable of accurate measurement as compared to the radicals within the radical gas stream.

As shown in FIG. 1, at least one sensor module 36 is in fluid communication with the sampling module 32 via the molecular compound stream conduit 34. In one embodiment, the sensor module 36 may be configured to detect and measure the concentration of radicals in at least one gas flow. Any variety of devices or systems may be used within or to form the sensor module 36. For example, in one embodiment the sensor module 36 comprises at least one detector configured to measure the radical flux within the radical gas stream. In another embodiment, the sensor module 36 is configured to measure the concentration of at least one chemical species within a gas flow. For example, the sensor module 36 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment the sensor module 36 includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 36 may further include at least one titration system or device. In one embodiment, in one embodiment, the sensing module 36 may be configured to reduce or eliminate recombination of the radicals within the gas stream into its molecular species. In another embodiment, the sensor module 36 may be configured to permit recombination of the radicals within a gas stream to its molecular species.

Referring again to FIG. 1, at least one sensor module output conduit 38 is in fluid communication with the sensor module 36 and the flow measurement and/or flow control module 40. In some embodiments, the flow measurement module 40 is configured to accurately measure a portion of the gas stream flowing there through. For example, the flow of the gas stream may be measured using a mass flow verifier (MFV). In another embodiment, the flow of the gas stream may be measured using a mass flow meter (MFM). Optionally, the flow may be determined by measuring the pressure differential between an orifice of known size within the multi-sensor gas sampling detection system 10 with the fluid conductance. Those skilled in the art will appreciate that any variety of flow measuring devices or systems they be used with the gas sampling detection system 10 disclosed herein. As shown in FIG. 1, at least one exhaust conduit 42 may be coupled to or in communication with the flow measurement module 40 and configured to exhaust the radical gas stream from the gas sampling detection system 10. Optionally, the exhaust conduit 42 may be in fluid communication with at least one vacuum source (not shown).

As shown in FIG. 1, the processing system 10 may include at least one optional processor module 52 which may be in communication with at least one component of the processing system 10. For example, in the illustrated embodiment, an optional processor module 52 is in communication with the radical gas generator 12 via at least one processor conduit 54. Further, the optional processor system 52 may be in communication with at least one of the optional sensor 50 via the processor conduit 54 and at least one optional sensor conduit 56, the sampling module 32 via the processor conduit 54 and at least one sampling conduit 58, the sensor module 36 via at least one sensor module conduit 60, and the flow measurement module 40 via at least one flow measurement conduit 62. In one embodiment, the optional processor module 52 may be configured to provide and receive data from at least one of the radical gas generator 12, the optional sensor 50, the sampling module 32, the sensor module 36, and the flow measurement module 40. As such, the optional processor module 52 may be configured to measure the flow condition within the processing system 10 and selectively vary the operating conditions of the processing system 10 to optimize system performance. More specifically, the optional processor module 52 may be configured to measure the concentration of radicals within the gas stream and vary the operating characteristics of the radical gas generator 12 to increase or decrease the concentration of radicals within the radical gas stream. Further, the optional processor module 52 may be in communication with and provide/receive data from at least one of the optional valve device 22, sensor 24, and chamber processor module 20 via at least one optional processing conduit 64. Optionally, the optional processor module 52 may be in communication with the various components of the processing system 10 wirelessly. Further, the optional processor module 52 may be configured to store performance data, processing formulas and times, lot number, and the like. In addition, the optional processor module 52 may be configured to communicate with one or more external processors via at least one computer network.

Optionally, as shown in FIG. 1, at least one analysis system or circuit 66 may be formed within the processing system 10. As shown, the analysis system 66 may include at least one of the sampling module 32, sensor module 36, flow measurement module 49, optional sensor 50, optional processor module 52, and the like. Further, the analysis system 66 may further include valve device 22 or other devices and components within the processing system 10.

Figure 2:
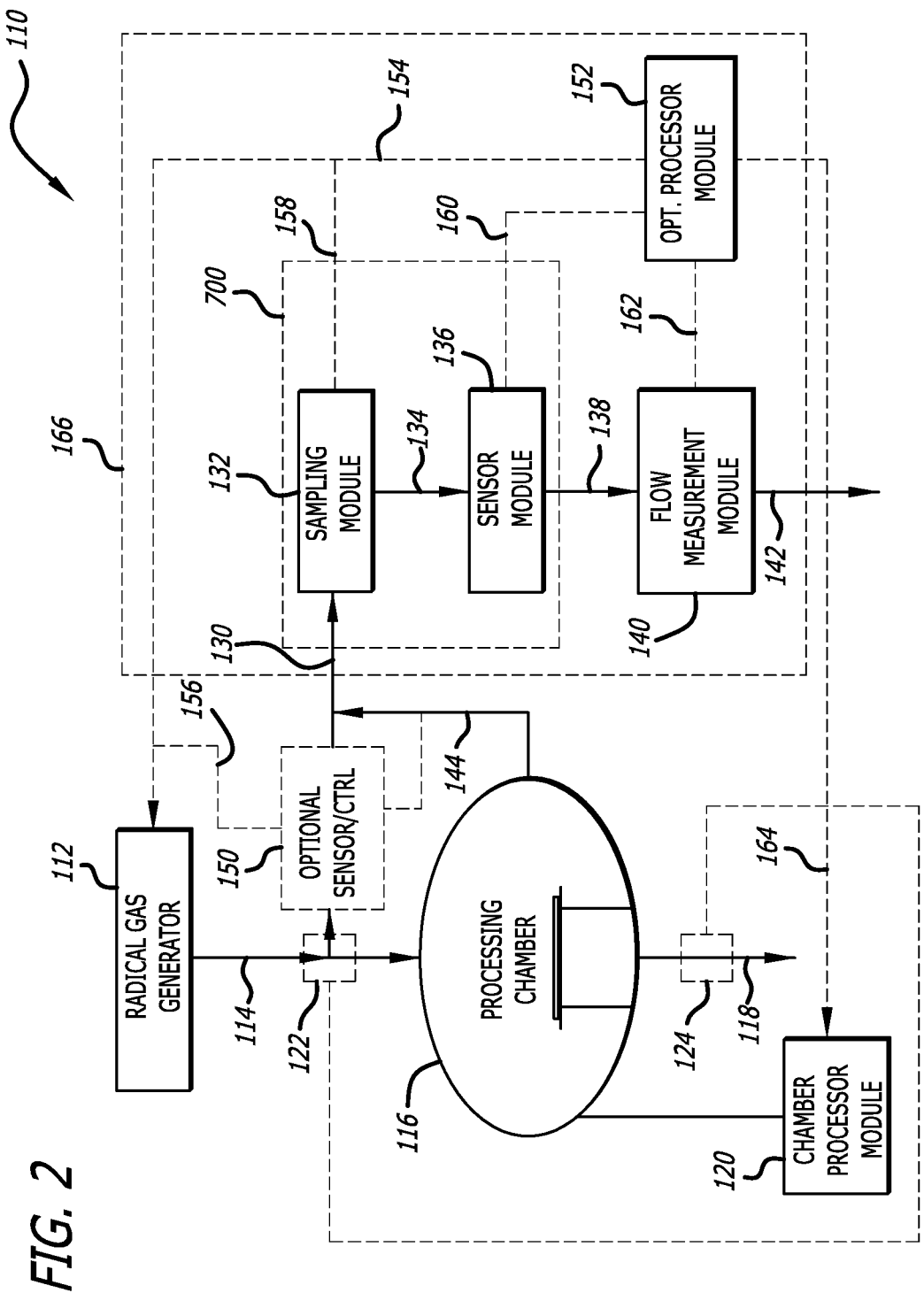
FIG. 2 shows a schematic diagram of another embodiment of a multi-sensor gas sampling detection system wherein gas samples are taken from a radical gas stream upstream from a processing chamber and from within the processing chamber.

FIG. 2 shows schematically another embodiment of a gas sampling detection system useful for detecting the concentration of radicals within a gas stream. The various components of the processing system 110 shown in FIG. 2 perform comparably to similarly named components shown in FIG.

1. Like the previous embodiment, the gas sampling detection system 110 may include at least one radical gas generator and/or reactive gas generator 112 configured to provide a reactive gas stream having radicals therein. The radical gas generator 112 may be in fluid communication with at least one processing chamber 116 via at least one gas passage 114. Like the previous embodiment, the radical gas generator 112 is in communication with at least one sample gas source and at least one plasma source configured to energize and dissociate sample gases and generate at least one reactive gas stream in response thereto.

Referring again to FIG. 2, optionally, the reactive gas conduit 114 may include one or more valve devices or systems, sensors, or similar devices 122 coupled thereto or in communication there with. For example, one or more valve devices 122 may be coupled to or otherwise in communication with the reactive gas conduit 114 thereby permitting a user to selectively permit and/or restrict the flow of at least one reactive gas stream through the reactive gas conduit 114. In one embodiment, the valve device 122 may be in communication with at least one optional processing module 152 via at least one processor conduit 154. Optionally, the processing module 152 may be configured to communicate with the various components of the processing system 110 wirelessly. During use, the processor module 152 may be configured to selectively open and/or close the valve device 122 thereby permitting or restrict the flow of the radical gas stream generated by the radical gas generator 112 into the sampling module 132.

As shown in FIG. 2, at least one processing chamber 116 may be coupled to or in communication with the radical gas generator 112 via the reactive gas conduit 114. At least one exhaust conduit 118 may be coupled to the processing chamber 116 and configured to evacuate one or more gases or materials from the processing chamber 116. Optionally, one or more control sensors, valves, scrubbers, or similar devices 124 may be coupled to or positioned proximate to the exhaust conduit 118, thereby permitting the user to selectively evacuate one or more gases or other materials from the processing chamber 116.

Referring again to FIG. 2, like the previous embodiment, at least one chamber processor module 120 may be coupled to or otherwise in communication with the processing chamber 118 and/or various components of the processing system. The chamber processing module 120 may be configured to provide localized control of the various components forming the processing system 110. In the illustrated embodiment the chamber processing module 120 is in communication with the processing chamber 116 via a conduit, although those skilled in the art will appreciate that the chamber processing module 120 may communicate with any of the components forming the processing system 110 via a conduit, wirelessly, or both.

As shown in FIG. 2, at least one sampling module 132 may be in fluid communication with the radical gas generator 112 via at least one sampling conduit 130. Those skilled in the art will appreciate that the sampling conduit 130 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, the sampling conduit 130 may be configured to chemically react with the highly reactive radicals contained within the radical gas stream flowing therein. In another embodiment, the sampling conduit 130 may be configured to be chemically inert. In one embodiment, the sampling conduit 130 is coupled directly to and in fluid communication with the radical gas generator 112. In the illustrated embodiment the sampling conduit 130 is in fluid communication with the radical gas generator 112 via the reactive gas conduit 114. Optionally, the sampling conduit 130 may be in fluid communication with the sampling control valve 122 positioned on the reactive gas conduit 114. For example, the sampling control valve 122 may be configured to selectively direct a prescribed volume of reactive gas traversing through the reactive gas conduit 114 to the sampling module 132 via the sampling conduit 130. Optionally, the sampling control valve 122 may be configured to selectively direct a prescribed flow rate of reactive gas traversing through the reactive gas conduit 114 to the sampling module 132 via the sampling conduit 130. Further, any number of additional components, valves, sensors, and the like may be positioned anywhere along the sampling conduit 130. For example, in the illustrated embodiment at least one sensor and/or control device 150 may be positioned along the sampling conduit 130. Exemplary sensor devices include, without limitations, thermocouples, temperature sensors, vacuum gauges, and the like. For example, in one embodiment the sensor device 150 comprises at least one thermistor. In another embodiment the sensor device 150 comprises at least one calorimetry system or device. Optionally, the sensor device 150 may comprise one or more titration systems or devices. Those skilled in the art will appreciate that the sensor device 150 may comprise any number of in situ measuring devices or systems, flow valves, flowmeters, flow verifiers, and the like.

Referring again to FIG. 2, the sampling module 132 may also be in fluid communication with the processing chamber 116 via at least one chamber sample gas conduit 144. As such, the sampling module 132 may be configured to analyze the radical gas stream upstream of the processing chamber 116 and within the processing chamber 116. Such analysis may occur sequentially or simultaneously. Like the sampling conduit 130, the chamber sample gas conduit 144 may include one or more valves, sensors, and the like thereon. As such, the flow of sample gas from the processing chamber 116 to the sampling module 132 may be selectively varied.

With reference to FIG. 2, the sampling module 132 may be coupled to at least one molecular compound stream conduit 134. Like the sampling conduit 130 the molecular compound stream conduit 134 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. In one embodiment at least a portion of at least one of the sampling conduit 130 and/or the molecular compound stream conduit 134 may be configured to react with the radical gas stream flowing therein. For example, in one embodiment at least a portion of the sampling conduit 130 and/or molecular compound stream conduit 134 may be configured to react with radicals within the gas flow to form chemical species more stable and capable of accurate measurement as compared to the radicals contained within the radical gas stream.

As shown in FIG. 2, like the previous embodiment, at least one sensor module 136 may be in fluid communication with the sampling module 132 via the molecular compound stream conduit 134. Optionally, the sensor module 136 may be configured to detect and measure the concentration of radicals in at least one gas flow. Any variety of devices or systems may be used within or to form the sensor module 136. For example, in one embodiment the sensor module 136 comprises at least one detector configured to measure the radical flux within the radical gas stream. In another embodiment, the sensor module 136 is configured to measure the concentration of at least one chemical species within a gas flow. For example, the sensor module 136 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment the sensor module 136 includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 136 may further include at least one titration system or device. In one embodiment, the sensing module 136 may be configured to reduce or eliminate recombination of the radicals within the gas stream into its molecular species. In another embodiment the sensor module 136 may be configured to permit recombination of the radicals within a gas stream to its molecular species.

Referring again to FIG. 2, at least one sensor module output conduit 138 is in fluid communication with the sensor module 136 in the flow measurement and/or flow control module 140, which may be configured to accurately measure a portion of the gas stream flowing there through. Like the previous embodiment, the flow of the gas stream may be measured using a mass flow verifier (MFV). In another embodiment, the flow of the gas stream may be measured using a mass flow meter (MFM). Optionally, the flow volume or rate may be determined by measuring the pressure differential between an orifice of known size within the multi-sensor gas sampling detection system 110 with the fluid conductance. Those skilled in the art appreciate that any variety of flow measuring devices or systems can be used with the gas sampling detection system 110 disclosed herein. As shown in FIG. 2, at least one exhaust conduit 142 may be coupled to or in communication with the flow measurement module 140 and configured to exhaust the radical gas stream from the gas sampling detection system 110. Optionally, the exhaust conduit 142 may be in fluid communication with at least one vacuum source (not shown).

As stated above, the processing system 110 may include at least one optional processor module 152 in communication with at least one component of the processing system 110. For example, the optional processor module 152 may be in communication with the radical gas generator 112 via at least one processor conduit 154. Further, the optional processor system 152 may be in communication with the optional sensor 150 via the processor conduit 154 and at least one optional sensor conduit 156, the sampling module 132 via the processor conduit 154 and at least one sampling conduit 158, the sensor module 136 via at least one sensor module conduit 160, and the flow measurement module 140 via at least one flow measurement conduit 162. In one embodiment, the optional processor module 152 may be configured to provide and receive data from at least one of the radical gas generator 112, the optional sensor 150, the sampling module 132, the sensor module 136, and the flow measurement module 140. As such, the optional processor module 152 may be configured to measure the flow conditions within the processing system 110 and selectively vary the operating conditions of the processing system 110 to optimize system performance. More specifically, the optional processor module 152 may be configured to measure the concentration of radicals within the gas stream vary the operating characteristics of the radical gas generator 112 to increase or decrease the concentration of radicals within the radical gas stream. Further, the optional processor module 152 may be in communication with and provide/receive data from at least one of the optional valve device 122, sensor 124, and chamber processor module 120 via at least one optional processing conduit 164. Optionally, the processor module 152 may be in communication with an external network.

Optionally, as shown in FIG. 2, like the previous embodiment, at least one analysis system or circuit 166 may be formed within the processing system 110. As shown, the analysis system 166 may include at least one of the sampling module 132, sensor module 136, flow measurement module 149, optional sensor 150, optional processor module 152, and the like. Further, the analysis system 166 may further include the valve device 122 or other devices and components within the processing system 110.

Figure 3:
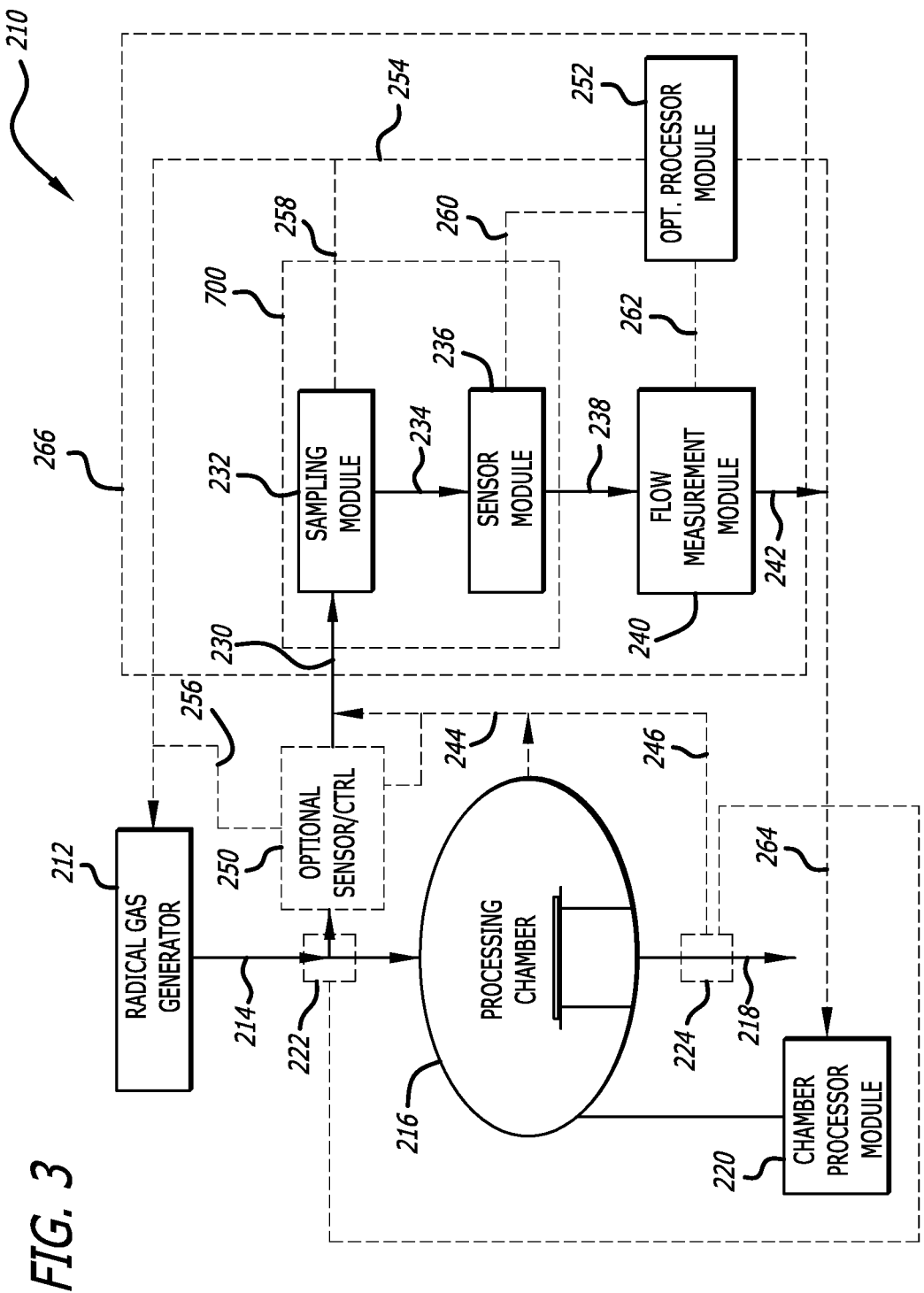
FIG. 3 shows a schematic diagram of another embodiment of a multi-sensor gas sampling detection system wherein gas samples are taken from a radical gas stream upstream from a processing chamber, from within the processing chamber, and downstream of the processing chamber.

FIG. 3 shows schematically still another embodiment of a gas sampling detection system useful for detecting the concentration of radicals within a gas stream. Like FIG. 2, the various components of the processing system 210 shown in FIG. 3 perform comparably to similarly named components shown in FIGS. 1 and 2. Like the previous embodiments, the gas sampling detection system 210 may include at least one radical gas generator and/or reactive gas generator 212 configured to provide a reactive gas stream having radicals therein. The radical gas generator 212 may be in fluid communication with at least one processing chamber 216 via at least one gas passage 214. Like the previous embodiment, the radical gas generator 212 is in communication with at least one sample gas source and at least one plasma source configured to energize and dissociate sample gases and generate at least one reactive gas stream in response thereto.

Referring again to FIG. 3, optionally, the reactive gas conduit 214 may include one or more valve devices or systems, sensors, or similar devices 222 coupled thereto or in communication there with. For example, one or more valve devices 222 may be positioned within or coupled to the reactive gas conduit 214 thereby permitting a user to selectively permit and/or restrict the flow of at least one reactive gas stream through the reactive gas conduit 214.

As shown in FIG. 3, at least one processing chamber 216 may be coupled to or in communication with the radical gas generator 212 via the reactive gas conduit 214. At least one exhaust conduit 218 may be coupled to the processing chamber 216 and configured to evacuate one or more gases or materials from the processing chamber 216. Optionally, one or more control sensors, valves, scrubbers, or similar devices 224 may be coupled to or positioned proximate to the exhaust conduit 218, thereby permitting the user to selectively evacuate one or more gases or other materials from the processing chamber 216.

Referring again to FIG. 3, like the previous embodiment, at least one chamber processor module 220 may be coupled to or otherwise in communication with the processing chamber 218 and/or various components of the processing system. The chamber processing module 220 may be configured to provide localized control of the various components forming the processing system 210. In the illustrated embodiment the chamber processing module 220 is in communication with the processing chamber 216 via a conduit, although those skilled in the art will appreciate that the chamber processing module 220 may communicate with any of the components forming the processing system 210 via a conduit, wirelessly, or both.

As shown in FIG. 3, at least one sampling module 232 may be in fluid communication with the radical gas generator 212 via at least one sampling conduit 230. Those skilled in the art appreciate the sampling conduit 230 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, the sampling conduit 230 may be configured to chemically react with the highly reactive radicals contained within the radical gas stream flowing therein. In another embodiment, the sampling conduit 230 may be configured to be chemically inert. In one embodiment, the sampling conduit 230 is coupled directly to and in fluid communication with the radical gas generator 212. In the illustrated embodiment the sampling conduit 230 is in fluid communication with the radical gas generator 212 via the reactive gas conduit 214. Optionally, the sampling conduit 230 may be in fluid communication with the sampling control valve 222 positioned on the reactive gas conduit 214. For example, the sampling control valve 222 may be configured to selectively direct a prescribed volume of reactive gas traversing through the reactive gas conduit 214 to the sampling module 232 via the sampling conduit 230. Optionally, the sampling control valve 222 may be configured to selectively direct a prescribed flow rate of reactive gas traversing through the reactive gas conduit 214 to the sampling module 232 via the sampling conduit 230. Further, any number of additional components, valves, sensors, and the like may be positioned anywhere along the sampling conduit 230. For example, in the illustrated embodiment at least one sensor and/or control device 250 may be positioned along the sampling conduit 230. Exemplary sensor devices include, without limitations, thermocouples, temperature sensors, vacuum gauges, and the like. For example, in one embodiment the sensor device 250 comprises at least one thermistor. In another embodiment the sensor device 250 comprises at least one calorimetry system or device. Optionally, the sensor device 250 may comprise one or more titration systems or devices. Those skilled in the art appreciate the sensor device 250 may comprise any number of in situ measuring devices or systems, flow valves, flowmeters, flow verifiers, and the like.

Referring again to FIG. 3, the sampling module 232 may also be in fluid communication with the processing chamber 216 and the exhaust conduit 218 via at least one of the at least one chamber sample gas conduit 244 and/or sample exhaust conduit 246. As such, the sampling module 232 may be configured to analyze the radical gas stream upstream of the processing chamber 216, the radical gas stream within the processing chamber 216, and the radical gas stream being emitted from the processing chamber via the exhaust conduit 218. Such analysis may occur sequentially or simultaneously. Like the sampling conduit 230, the chamber sample gas conduit 244, and/or the exhaust conduit 218 may include one or more valves, sensors, and the like thereon. As such, the flow of sample gas from the processing chamber 216 to the sampling module 232, and/or the flow of sample gas from the exhaust conduit 218 to the sampling module 232, or both, may be selectively varied.

With reference to FIG. 3, the sampling module 232 may be coupled to at least one molecular compound stream conduit 234. Like the sampling conduit 230, the molecular compound stream conduit 234 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. In one embodiment, at least a portion of at least one of the sampling conduit 230 and/or the molecular compound stream conduit 234 may be configured to react with the radical gas stream flowing therein. For example, in one embodiment at least a portion of the sampling conduit 230 in/or molecular compound stream conduit 234 may be configured to react with radicals within the gas flow to form chemical species more stable and capable of accurate measurement as compared to the radicals container within the radical gas stream.

As shown in FIG. 3, like the previous embodiments, at least one sensor module 236 is in fluid communication with the sampling module 232 via the molecular compound stream conduit 234. Optionally, the sensor module 236 may be configured to detect and measure the concentration of radicals in at least one gas flow. Any variety of devices or systems may be used within or to form the sensor module 236. For example, in one embodiment the sensor module 236 comprises at least one detector configured to measure the radical flux within the radical gas stream. In another embodiment, the sensor module 236 is configured to measure the concentration of at least one chemical species within a gas flow. For example, the sensor module 236 may be configured to measure the concentration of carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment, the sensor module 236 includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensor module 236 may further include at least one titration system or device. In one embodiment, in one embodiment, the sensor module 236 may be configured to reduce or eliminate recombination of the radicals within the gas stream into its molecular species. Another embodiment the sensor module 236 may be configured to permit recombination of the radicals within a gas stream to its molecular species.

Referring again to FIG. 3, at least one sensor module output conduit 238 is in fluid communication with the sensor module 236 and the flow measurement and/or flow control module 240, which may be configured to accurately measure a portion of the gas stream flowing there through. Like the previous embodiment, the flow of the gas stream may be measured using a mass flow verifier (MFV). In another embodiment, the flow of the gas stream may be measured using a mass flow meter (MFM). Optionally, the flow may be determined by measuring the pressure differential between an orifice of known size within the multi-sensor gas sampling detection system 210 with the fluid conductance. Those skilled in the art appreciate that any variety of flow measuring devices or systems may be used with the gas sampling detection system 210 disclosed herein. As shown in FIG. 3, at least one exhaust conduit 242 may be coupled to or in communication with the flow measurement module 240 and configured to exhaust the radical gas stream from the gas sampling detection system 210. Optionally, the exhaust conduit 242 may be in fluid communication with at least one vacuum source (not shown).

As stated above, the processing system 210 may include at least one optional processor module 252 in communication with at least one component of the processing system 210. For example, the optional processor module 252 may be in communication with the radical gas generator 212 via at least one processor conduit 254. Further, the optional processor system 252 may be in communication with at least one of the optional sensor 250 via the processor conduit 254 and at least one optional sensor conduit 256, the sampling module 232 via the processor conduit 254 and at least one sampling conduit 258, the sensor module 236 via at least one sensor module conduit 260, and the flow measurement module 240 via at least one flow measurement conduit 262. In one embodiment, the optional processor module 252 may be configured to provide and receive data from at least one of the radical gas generator 212, the optional sensor 250, the sampling module 232, the sensor module 236, and the flow measurement module 240. As such, the optional processor module 252 may be configured to measure the flow condition within the processing system 210 and selectively vary the operating conditions of the processing system 210 to optimize system performance. More specifically, the optional processor module 252 may be configured to measure the concentration of radicals within the gas stream vary the operating characteristics of the radical gas generator 212 to increase or decrease the concentration of radicals within the radical gas stream. Further, the optional processor module 252 may be in communication with and provide/receive data from at least one of the optional valve device 222, sensor 224, and chamber processor module 220 via at least one optional processing conduit 264. Further, the processor module 252 may be in communication with an external network.

Optionally, as shown in FIG. 3, like the previous embodiments, at least one analysis system or circuit 266 may be formed within the processing system 210. As shown, the analysis system 266 may include at least one of the sampling module 232, sensor module 236, flow measurement module 249, optional sensor 250, optional processor module 252, and the like. Further, the analysis system 266 may further include the valve device 222 or other devices and components within the processing system 210.

Figure 4:
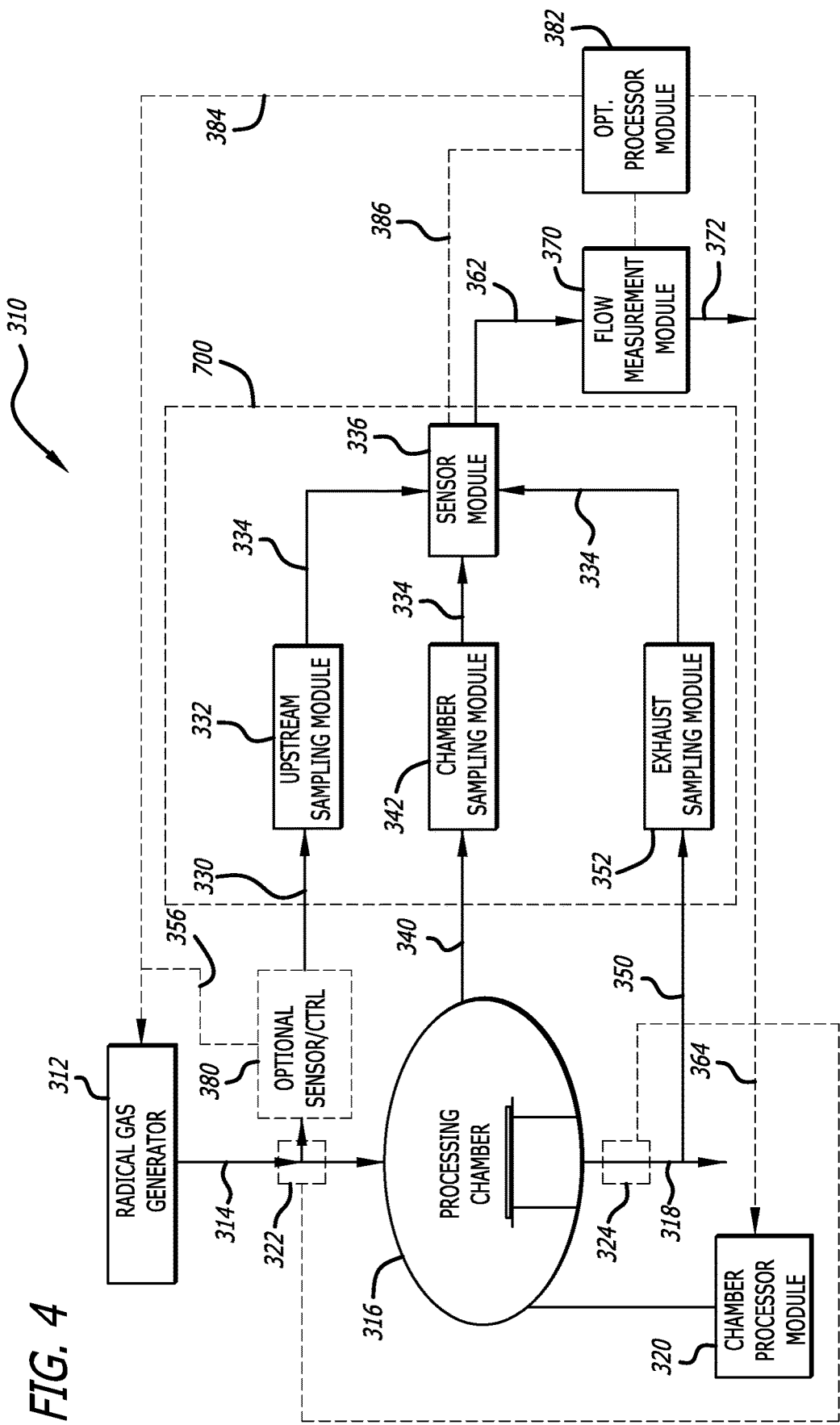
FIG. 4 shows a schematic diagram of an alternate embodiment of a multi-sensor gas sampling detection system.

FIG. 4 shows schematically another embodiment of a gas sampling detection system useful for detecting the concentration of radicals within a gas stream. Unlike the previous embodiments, the present embodiment includes multiple sampling modules providing data to one or more sensor modules. Like the previous embodiments, the various components of the processing system 310 shown in FIG. 4 perform comparably to similarly named components shown in FIGS. 1-3. Like the previous embodiments, the gas sampling detection system 310 may include at least one radical gas generator and/or reactive gas generator 312 configured to provide a reactive gas stream having radicals therein. The radical gas generator 312 may be in fluid communication with at least one processing chamber 316 via at least one gas passage 314. Optionally, the reactive gas conduit 314 may include one or more valve devices or systems, sensors, or similar devices 322 coupled thereto or in communication there with. For example, one or more valve devices 322 may be positioned or coupled to the reactive gas conduit 314 thereby permitting a user to selectively permit and/or restrict the flow of at least one reactive gas stream through the reactive gas conduit 314.

As shown in FIG. 4, at least one processing chamber 316 may be coupled to or in communication with the radical gas generator 312 via the reactive gas conduit 314. At least one exhaust conduit 318 may be coupled to the processing chamber 316 and configured to evacuate one or more gases or materials from the processing chamber 316. Optionally, one or more control sensors, valves, scrubbers, or similar devices 324 may be coupled to or positioned proximate to the exhaust conduit 318, thereby permitting the user to selectively evacuate one or more gases or other materials from the processing chamber 316.

Referring again to FIG. 4, like the previous embodiments, at least one chamber processor module 320 may be coupled to or otherwise in communication with the processing chamber 318 and/or various components of the processing system. The chamber processing module 320 may be configured to provide localized control over the various components forming the processing system 310. The illustrated embodiment the chamber processing module 320 is in communication with the processing chamber 316 via a conduit, although those skilled in the art appreciate that the chamber processing module 320 may communicate with any of the components forming the processing system 310 via a conduit, wirelessly, or both.

As shown in FIG. 4, at least one upstream sampling module 332 may be in fluid communication with the radical gas generator 312 via at least one sampling conduit 330. Those skilled in the art will appreciate that the sampling conduit 330 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, the sampling conduit 330 may be configured to chemically react with the highly reactive radicals contained within the radical gas stream flowing therein. In another embodiment, the sampling conduit 330 may be configured to be chemically inert. In one embodiment, the sampling conduit 330 is coupled directly to and in fluid communication with the radical gas generator 312. In the illustrated embodiment the sampling conduit 330 is in fluid communication with the radical gas generator 312 via the reactive gas conduit 314. Optionally, the sampling conduit 330 may be in fluid communication with the sampling control valve 322 positioned on the reactive gas conduit 314. For example, the sampling control valve 322 may be configured to selectively direct a prescribed volume of reactive gas traversing through the reactive gas conduit 314 to the upstream sampling module 332 via the sampling conduit 330. Optionally, the sampling control valve 322 may be configured to selectively direct a prescribed flow rate of reactive gas traversing through the reactive gas conduit 314 to the upstream sampling module 332 via the sampling conduit 230. Further, any number of additional components, valves, sensors, and the like may be positioned anywhere along the sampling conduit 330. For example, in the illustrated embodiment at least one sensor and/or control device 380 may be positioned along the sampling conduit 330. Exemplary sensor devices include, without limitations, thermocouples, temperature sensors, vacuum gauges, and the like. For example, in one embodiment the sensor device 380 comprises at least one thermistor. In another embodiment the sensor device 380 comprises at least one calorimetry system or device. Optionally, the sensor device 380 may comprise one or more titration systems or devices. Those skilled in the art will appreciate the sensor device 380 may comprise any number of in situ measuring devices or systems, flow valves, flowmeters, flow verifiers, and the like.

Referring again to FIG. 4, at least one chamber sampling module 342 may be in fluid communication with the processing chamber 316 via at least one chamber sample gas conduit 340. As such, the chamber sampling module 342 may be configured to analyze the radical gas stream within the processing chamber 316. Like the upstream sampling conduit 330, the chamber sample gas conduit 340 may include one or more valves, sensors, and the like thereon. As such, the flow of sample gas from the processing chamber 316 to the chamber sampling module 342 may be selectively varied.

As shown in FIG. 4, optionally, at least one exhaust sampling module 352 may be in fluid communication with the processing chamber 316 via at least one exhaust sample gas conduit 350. As such, the chamber sampling module 352 may be configured to analyze the radical gas stream emitted from the processing chamber 316 via the exhaust conduit 318. Optionally, the exhaust sample gas conduit 350 may include one or more valves, sensors, and the like thereon. As such, the flow of sample gas emitted from the processing chamber 316 via the exhaust conduit 318 may be selectively varied.

With reference to FIG. 4, at least one of the upstream sampling module 332, chamber sampling module 342, and exhaust sampling module 352 may be coupled to at least one molecular compound stream conduit 334. Like the sampling conduit 330 the molecular compound stream conduit 334 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. In one embodiment, at least a portion of at least one of the upstream sampling conduit 330, chamber sampling module 340, exhaust sampling module 350, and/or the molecular compound stream conduit 334 may be configured to react with the radical gas stream flowing therein. For example, in one embodiment at least a portion of the sampling conduit 330 and/or molecular compound stream conduit 334 may be configured to react with radicals within the gas flow to form chemical species more stable and capable of accurate measurement as compared to the radicals contained within the radical gas stream.

As shown in FIG. 4, like the previous embodiment at least one sensor module 336 is in fluid communication with at least one of the upstream sampling module 332, chamber sampling module 342, and exhaust sampling module 352 via the molecular compound stream conduit 334. The sensor module 336 may be configured to detect and measure the concentration of radicals in at least one gas flow. Any variety of devices or systems may be used within or to form the sensor module 336. For example, in one embodiment the sensor module 336 comprises at least one detector configured to measure the radical flux within the radical gas stream. In another embodiment, the sensor module 336 is configured to measure the concentration of at least one chemical species within a gas flow. For example, the sensor module 336 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment the sensor module 336 includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 336 may further include at least one titration system or device. In one embodiment, the sensing module 336 may be configured to reduce or eliminate recombination of the radicals within the gas stream into its molecular species. In another embodiment, the sensor module 336 may be configured to permit recombination of the radicals within a gas stream to its molecular species.

Referring again to FIG. 4, at least one sensor module output conduit 362 is in fluid communication with the sensor module 336 and the flow measurement and/or flow control module 370, which may be configured to accurately measure a portion of the gas stream flowing there through. Like the previous embodiment, the flow of the gas stream may be measured using a mass flow verifier (hereinafter MFV). In another embodiment, the flow of the gas stream may be measured using a mass flow meter (hereinafter MFM). Optionally, the flow may be determined by measuring the pressure differential between an orifice of known size within the multi-sensor gas sampling detection system 310 with the fluid conductance. Those skilled in the art will appreciate that any variety of flow measuring devices or systems may be used with the gas sampling detection system 310 disclosed herein. As shown in FIG. 4, at least one exhaust conduit 372 may be coupled to or in communication with the flow measurement module 370 and configured to exhaust the radical gas stream from the gas sampling detection system 310. Optionally, the exhaust conduit 372 may be in fluid communication with at least one vacuum source (not shown).

The processing system 310 may include at least one optional processor module 382 in communication with at least one component of the processing system 310. For example, the optional processor module 382 may be in communication with the radical gas generator 312 via at least one processor conduit 384. Further, the optional processor system 382 may be in communication with at least one of the optional sensor 380 and upstream sampling module 332 via the processor conduit 384 and at least one optional sensor conduit 356, the sensor module 336 via at least one sensor module conduit 386, or both. As such, the optional processor module 382 may be configured to measure the flow conditions within the processing system 310 and selectively vary the operating conditions of the processing system 310 to optimize system performance. More specifically, the optional processor module 382 may be configured to measure and/or calculate the concentration of radicals within the gas stream and vary the operating characteristics of the radical gas generator 312 to increase or decrease the concentration of radicals within the radical gas stream. Further, the optional processor module 382 may be in communication with and provide/receive data from at least one of the optional valve device 322, sensor 324, and chamber processor module 320 via at least one optional processing conduit 364.

Figure 5:
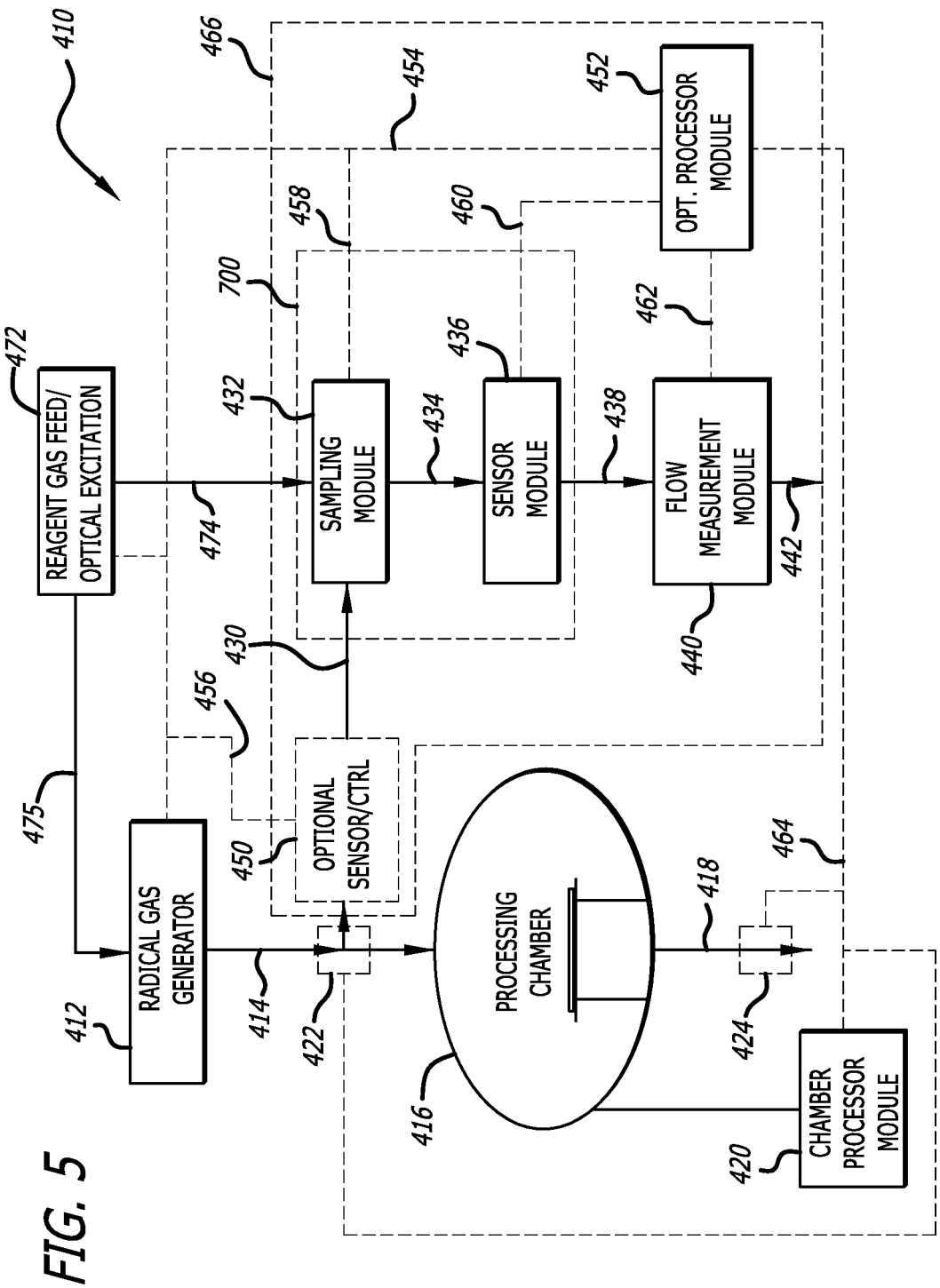
FIG. 5 shows a schematic diagram of an alternate embodiment of a multi-sensor gas sampling detection system having a reagent source coupled thereto.

FIG. 5 shows schematically an embodiment of a gas sampling detection system useful for detecting the concentration of radicals within a gas stream. As shown, the gas sampling detection system 410 includes at least one plasma generator and/or radical gas generator 412 in fluid communication with at least one processing chamber 416 via at least one gas passage 414. In one embodiment, the radical gas generator 412 is in communication with at least one sample gas source and at least one plasma source configured to energize and dissociate sample gases and generate at least one reactive gas stream. In one specific embodiment the radical gas generator 412 comprises a RF toroidal plasma source; although those skilled in the art will appreciate that any variety of plasma sources or radical gas sources may be used with the present systems. In one embodiment the radical gas generator 412 uses hydrogen ($H_2$) plasma to create atomic hydrogen. In another embodiment the radical gas generator 412 utilizes oxygen ($O_2$) plasma to create atomic oxygen. Optionally, the radical gas generator 412 may utilize nitrogen trifluoride ($NF_3$), fluorine ($F_2$), chlorine ($Cl_2$) or any variety of other materials to create a reactive plasma containing one or more radicals within the gas stream. Alternatively, radical gases may be generated by other gas excitation methods, including electron beam excitation, laser excitation, or hot-filament excitation. Further, the above description discloses various embodiments of RF-based plasma generation systems; although those skilled in the art will appreciate that any variety of alternate radical gas generation systems may be used with the present system. Exemplary alternate radical gas generation systems include, without limitation, glow discharge plasma systems, capacitively coupled plasma systems, cascade art plasma systems, inductively coupled plasma systems, wave heated plasma systems, arc discharge plasma systems, coronal discharge plasma systems, dielectric barrier discharge systems, capacitive discharge systems, Piezoelectric direct discharge plasma systems, and the like.

Referring again to FIG. 5, at least one processing chamber 416 may be in fluid communication with the radical gas generator 412 via at least one reactive gas conduit 414. In some applications, the reactive gas conduit 414 is manufactured from a chemically inert material or a material having low chemical reactivity. Exemplary materials include, without limitation, quartz, sapphire, stainless steel, strengthened steel, aluminum, ceramic materials, glass, brass, nickel, $Y_2O_3$, $YAlO_x$, various alloys, and coated metal such as anodized aluminum. In one embodiment, a single reactive gas conduit 414 is in fluid communication with a single radical gas generator 412. In another embodiment multiple reactive gas conduits 414 are in fluid communication with a single reactive gas generator 412. In yet another embodiment a single reactive gas conduit 414 is in communication with multiple radical gas generators 412. As such, any number of reactive gas conduits 414 may be in communication with any number of radical gas generators 412. Optionally, the reactive gas conduit 414 may include one or more valve devices or systems, sensors, or similar devices 422 coupled thereto or in communication there with. For example, one or more valve devices 422 may be coupled to the reactive gas conduit 414 thereby permitting a user to selectively permit and/or restrict the flow of at least one reactive gas stream through the reactive gas conduit 414.

The processing chamber 416 may be coupled to or in communication with the radical gas generator 412 via the reactive gas conduit 414. In one embodiment, the processing chamber 416 comprises one or more vacuum chambers or vessels configured to have one or more substrates, semiconductor wafers, or similar materials positioned therein. Optionally, the processing chamber 416 may be used for atomic layer processing of semiconductor substrates or wafers. Optionally, the processing chamber 416 may be used for processing any variety of substrates or materials using any variety of processing methods were systems. Exemplary processing methods include, without limitation, physical vapor deposition (PVD), chemical vapor deposition (CVD), rapid thermal chemical vapor deposition (RTCVD), atomic layer deposition (ALD), atomic layer etching (ALE), and the like. Those skilled in the art will appreciate that the processing chamber 416 be manufactured from any variety of materials, including, without limitation, stainless steel, aluminum, mild steel, brass, high-density ceramics, glass, acrylic, and the like. In one embodiment, at least one interior surface of the processing chamber 416 may include at least one coating, anodized material, sacrificial material, physical feature or element, and the like intended to selectively vary the reactivity, durability, and/or fill micro-pores of the interior surfaces of the processing chamber 416. At least one exhaust conduit 418 may be coupled to the processing chamber 416 and configured to evacuate one or more gases or materials from the processing chamber 416. Optionally, one or more control sensors, valves, scrubbers, or similar devices 424 may be coupled to or positioned proximate to the exhaust conduit 418, thereby permitting the user to selectively evacuate one or more gases or other materials from the processing chamber 416.

Referring again to FIG. 5, at least one chamber processor module 420 may be coupled to or otherwise in communication with the processing chamber 418 and/or various components of the processing system. The chamber processing module 420 may be configured to provide localized control of the various components forming the processing system 10. In the illustrated embodiment the chamber processing module 420 is in communication with the processing chamber 416 via a conduit, although those skilled in your will appreciate that the chamber processing module 420 may communicate with any of the components forming the processing system 410 via conduit, wirelessly, or both.

As shown in FIG. 5, at least one sampling module 432 may be in fluid communication with the radical gas generator 412 via at least one sampling conduit 430. Those skilled in the art will appreciate that the sampling conduit 430 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, in some embodiments the sampling conduit 430 may be configured to chemically react with the highly reactive radicals contained within the radical gas stream flowing therein. In yet another embodiment, the sampling conduit 430 may consist of a catalytic material to facilitate the recombination of atomic gas species into its molecular gas species, such that the recombination energy of the atomic gas is released and measured. In other embodiments, the sampling conduit 430 may be configured to be chemically inert.

Referring again to FIG. 5, at least one reaction gas feed or source 472 may be configured to provide at least one reaction mechanism or stream 474 to the sampling module 432. Alternatively, the reaction source 472 may be in communication with the radical gas generator 412 through at least one stream conduit 475. Any variety of reaction sources 472 configured to provide any variety of may be used in the present system. For example, in one embodiment, the reaction source 472 comprises at least one source of a reactive gas and is configured to react with the atomic radicals, molecular radicals, and short-lived molecules within the sampling module 432. Exemplary reactive gases include, without limitations, gases such as nitrogen, oxygen, hydrogen, compounds, such as $NH_3NO_2$, or any variety of atomic radicals generated with a separate plasma source. In another embodiment, the reaction source 472 comprises at least one excitation source configured to provide excitation energy to the atomic radicals, molecular radicals, and short-lived molecules within the sampling module 432. For example, in one embodiment, the reaction source 472 comprises at least one source of optical radiation configured to provide excitation energy to the sampling module 432.

As shown in FIG. 5, the sampling conduit 430 may include any variety of sensors, valves, heating elements, cooling elements, and the like thereon. In one embodiment, the sampling conduit 430 is coupled directly to and in fluid communication with the radical gas generator 412. In the illustrated embodiment the sampling conduit 430 is in fluid communication with the radical gas generator 412 via the reactive gas conduit 414. Optionally, the sampling conduit 430 may be in fluid communication with the sampling control valve 422 positioned on the reactive gas conduit 414. For example, the sampling control valve 422 may be configured to selectively direct a prescribed volume of reactive gas traversing through the reactive gas conduit 414 to the sampling module 432 via the sampling conduit 430. In another embodiment, the sampling control valve 422 may be configured to selectively direct a prescribed flow rate of reactive gas traversing through the reactive gas conduit 414 to the sampling module 432 via the sampling conduit 430. Further, any number of additional components, valves, sensors, and the like may be positioned anywhere along the sampling conduit 430. For example, in the illustrated embodiment at least one sensor and/or control device 450 may be positioned along the sampling conduit 430. Exemplary sensor devices include, without limitations, thermocouples, temperature sensors, optical sensors, UV, optical or infrared spectrometers, charge particle detectors, vacuum gauges, mass spectrometers, and the like. For example, in one embodiment the sensor device 450 comprises at least one thermistor. In another embodiment the sensor device 450 comprises at least one calorimetry system or device. In another embodiment, a novel calorimetry system is discussed in detail and shown in FIGS. 8-15 of the present application. Optionally, the sensor device 450 may comprise one or more titration systems or devices. Those skilled in the arts will appreciate the sensor device 450 may comprise any number of in situ measuring devices were systems, flow valves, flowmeters, flow verifiers, and the like.

Referring again to FIG. 5, in the illustrated embodiment the sampling module 432 is coupled to at least one molecular compound stream conduit 434. Like the sampling conduit 430, the molecular compound stream conduit 434 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. In one embodiment, at least a portion of at least one of the sampling conduit 430 and/or the molecular compound stream conduit 434 may be configured to react with the radical gas stream flowing therein. For example, in one embodiment, at least a portion of the sampling conduit 430 and/or molecular compound stream conduit 434 may be configured to react with radicals within the gas flow to form chemical species more stable and capable of accurate measurement as compared to the radicals.

As shown in FIG. 5, at least one sensor module 436 is in fluid communication with the sampling module 432 via at least one molecular compound stream conduit 434. In one embodiment, the sensor module 436 may be configured to detect and measure the concentration of radicals in at least one gas flow. Any variety of devices or systems may be used within or to form the sensor module 436. For example, in one embodiment, the sensor module 436 comprises at least one detector configured to measure the radical flux within the radical gas stream. In another embodiment, the sensor module 436 is configured to measure the concentration of at least one chemical species within a gas flow. For example, the sensor module 436 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment, the sensor module includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 436 may further include at least one titration system or device. In one embodiment, the sensing module 436 may be configured to reduce or eliminate recombination of the radicals within the gas stream into its molecular species. In another embodiment, the sensor module 436 may be configured to permit recombination of the radicals within a gas stream to its molecular species.

Referring again to FIG. 5, at least one sensor module output conduit 438 is in fluid communication with the sensor module 436 and the flow measurement and/or flow control module 440. In some embodiments, the flow measurement module 440 is configured to accurately measure a portion of the gas stream flowing there through. For example, the flow of the gas stream may be measured using a mass flow verifier (MFV). In another embodiment, the flow of the gas stream may be measured using a mass flow meter (MFM). Optionally, the flow may be determined by measuring the pressure differential between an orifice of known size within the multi-sensor gas sampling detection system 410 with the fluid conductance. Those skilled in the art will appreciate that any variety of flow measuring devices or systems may be used with the gas sampling detection system 410 disclosed herein. As shown in FIG. 5, at least one exhaust conduit 442 may be coupled to or in communication with the flow measurement module 440 and configured to exhaust the radical gas stream from the gas sampling detection system 410. Optionally, the exhaust conduit 442 may be in fluid communication with at least one vacuum source (not shown).

As shown in FIG. 5, the processing system 410 may include at least one optional processor module 452 in communication with at least one component of the processing system 410. For example, in the illustrated embodiment, an optional processor module 452 is in communication with the radical gas generator 412 via at least one processor conduit 454. Further, the optional processor system 452 may be in communication with at least one of the optional sensor 450 via the processor conduit 454 and at least one optional sensor conduit 456, the sampling module 432 via the processor conduit 454 and at least one sampling conduit 458, the sensor module 436 via at least one sensor module conduit 460, and the flow measurement module 440 via at least one flow measurement conduit 462. Further, the reaction source 472 may be in communication with the optional processor system 452 via the processor conduit 454. In one embodiment, the optional processor module 452 may be configured to provide and receive data from at least one of the radical gas generator 412, the optional sensor 450, the sampling module 432, the sensor module 436, and the flow measurement module 440. As such, the optional processor module 452 may be configured to measure the flow conditions within the processing system 410 and selectively vary the operating conditions of the processing system 410 to optimize system performance. More specifically, the optional processor module 452 may be configured to measure the concentration of radicals within the gas stream vary the operating characteristics of the radical gas generator 412 to increase or decrease the concentration of radicals within the radical gas stream. Further, the optional processor module 452 may be in communication with and provide/receive data from at least one of the optional valve device 422, sensor 424, and chamber processor module 420 via at least one optional processing conduit 464. Optionally, the processor 452 may be in communication with the various components of the processing system 410 wirelessly. Further, the processor 452 may be configured to store performance data, processing formulas and times, lot number, and the like. In addition, the processor 452 may be configured to communicate with one or more external processors via at least one computer network.

Optionally, as shown in FIG. 5, at least one analysis system or circuit 466 may be formed within the processing system 410. As shown, the analysis system 466 may include at least one of the sampling module 432, sensor module 436, flow measurement module 449, optional sensor 450, optional processor module 452, and the like. Further, the analysis system 466 may further include valve device 422 or other devices and components within the processing system 410.

Figure 6:
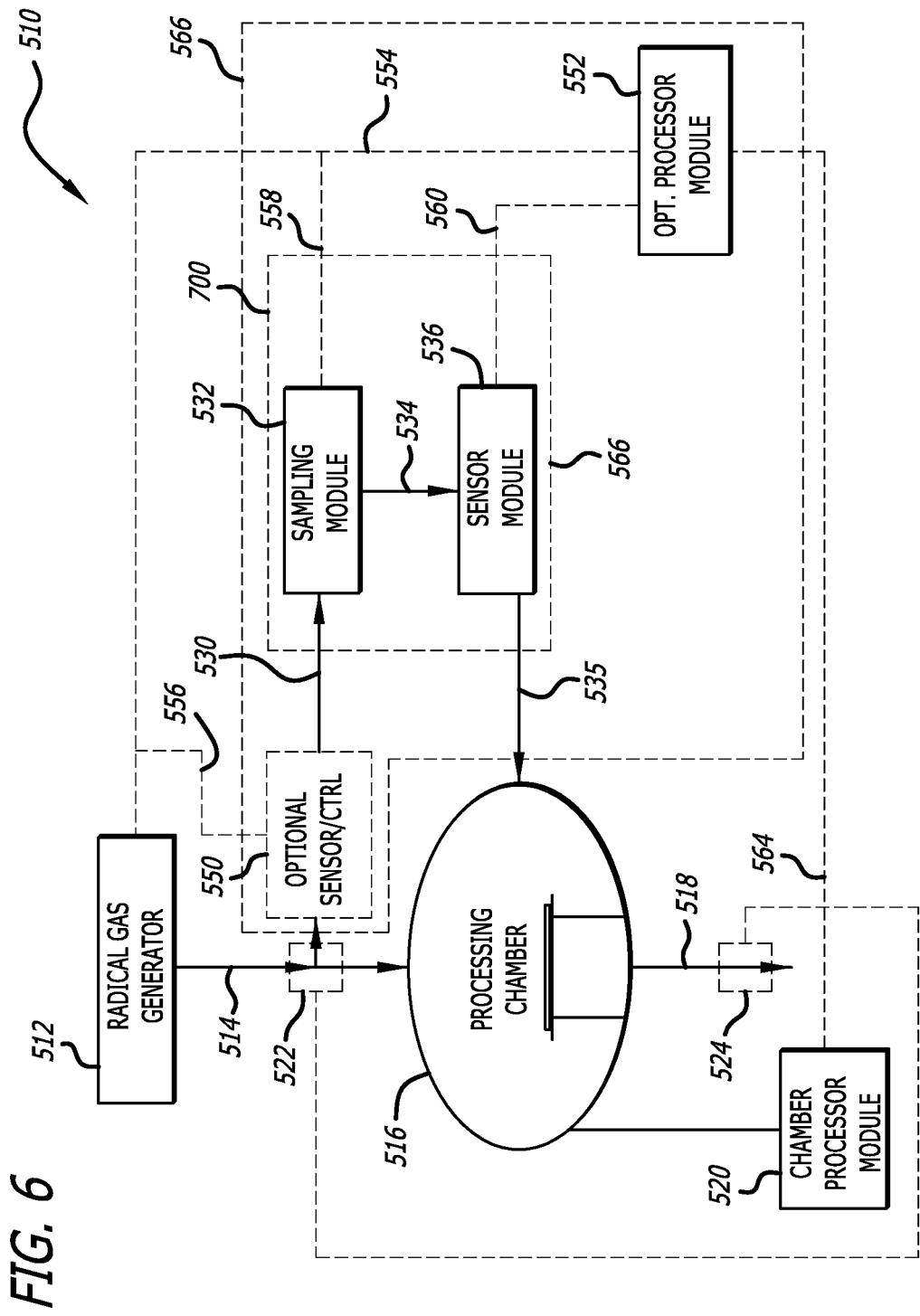
FIG. 6 shows a schematic diagram of another alternate embodiment of a multi-sensor gas sampling detection system.

FIG. 6 shows schematically an embodiment of a gas sampling detection system useful for detecting the concentration of radicals within a gas stream. As shown, the gas sampling detection system 510 includes at least one plasma generator and/or radical gas generator 512 in fluid communication with at least one processing chamber 516 via at least one gas passage 514. In one embodiment, the radical gas generator 512 is in communication with at least one sample gas source and at least one plasma source configured to energize and dissociate sample gases and generate at least one reactive gas stream. In one specific embodiment the radical gas generator 512 comprises a RF toroidal plasma source; although those skilled in the art will appreciate that any variety of plasma sources or radical gas sources may be used with the present systems. In one embodiment the radical gas generator 512 uses hydrogen ($H_2$) plasma to create atomic hydrogen. In another embodiment the radical gas generator 512 utilizes oxygen ($O_2$) plasma to create atomic oxygen. Optionally, the radical gas generator 512 may utilize nitrogen trifluoride ($NF_3$), fluorine ($F_2$), chlorine ($Cl_2$) or any variety of other materials to create a reactive plasma containing one or more radicals within the gas stream. Alternatively, radical gases may be generated by other gas excitation methods, including electron beam excitation, laser excitation, or hot-filament excitation. Further, the above description discloses various embodiments of RF-based plasma generation systems; although those skilled in the art will appreciate that any variety of alternate radical gas generation systems may be used with the present system. Exemplary alternate radical gas generation systems include, without limitation, glow discharge plasma systems, capacitively coupled plasma systems, cascade art plasma systems, inductively coupled plasma systems, wave heated plasma systems, arc discharge plasma systems, coronal discharge plasma systems, dielectric barrier discharge systems, capacitive discharge systems, Piezoelectric direct discharge plasma systems, and the like.

Referring again to FIG. 6, at least one processing chamber 516 may be in fluid communication with the radical gas generator 512 via at least one reactive gas conduit 514. In some applications, the reactive gas conduit 514 is manufactured from a chemically inert material or a material having low chemical reactivity. Exemplary materials include, without limitation, quartz, sapphire, stainless steel, strengthened steel, aluminum, ceramic materials, glass, brass, nickel, $Y_2O_3$, $YAlO_x$, various alloys, and coated metal such as anodized aluminum. In one embodiment, a single reactive gas conduit 514 is in fluid communication with a single radical gas generator 512. In another embodiment multiple reactive gas conduits 514 are in fluid communication with a single reactive gas generator 512. In yet another embodiment a single reactive gas conduit 514 is in communication with multiple radical gas generators 512. As such, any number of reactive gas conduits 514 may be in communication with any number of radical gas generators 512. Optionally, the reactive gas conduit 514 may include one or more valve devices or systems, sensors, or similar devices 522 coupled thereto or in communication there with. For example, one or more valve devices 522 may be coupled to the reactive gas conduit 514 thereby permitting a user to selectively permit and/or restrict the flow of at least one reactive gas stream through the reactive gas conduit 514.

As shown in FIG. 6, the processing chamber 516 may be coupled to or in communication with the radical gas generator 512 via the reactive gas conduit 514. In one embodiment, the processing chamber 516 comprises one or more vacuum chambers or vessels configured to have one or more substrates, semiconductor wafers, or similar materials positioned therein. For example, the processing chamber 516 may be used for atomic layer processing of semiconductor substrates or wafers. Optionally, the processing chamber 516 may be used for processing any variety of substrates or materials using any variety of processing methods were systems. Exemplary processing methods include, without limitation, physical vapor deposition (PVD), chemical vapor deposition (CVD), rapid thermal chemical vapor deposition (RTCVD), atomic layer deposition (ALD), atomic layer etching (ALE), and the like. Those skilled in the art will appreciate that the processing chamber 516 may be manufactured from any variety of materials, including, without limitation, stainless steel, aluminum, mild steel, brass, high-density ceramics, glass, acrylic, and the like. For example, at least one interior surface of the processing chamber 516 may include at least one coating, anodized material, sacrificial material, physical feature or element, and the like intended to selectively vary the reactivity, durability, and/or fill micro-pores of the interior surfaces of the processing chamber 16. At least one exhaust conduit 518 may be coupled to the processing chamber 516 and configured to evacuate one or more gases or materials from the processing chamber 516. Optionally, one or more control sensors, valves, scrubbers, or similar devices 524 may be coupled to or positioned proximate to the exhaust conduit 518, thereby permitting the user to selectively evacuate one or more gases or other materials from the processing chamber 516.

Referring again to FIG. 6, at least one chamber processor module 520 may be coupled to or otherwise in communication with the processing chamber 518 and/or various components of the processing system. The chamber processing module 520 may be configured to provide localized control of the various components forming the processing system 510. In the illustrated embodiment the chamber processing module 520 is in communication with the processing chamber 516 via a conduit, although those skilled in your will appreciate that the chamber processing module 520 may communicate with any of the components forming the processing system 510 via conduit, wirelessly, or both.

As shown in FIG. 6, at least one sampling module 532 may be in fluid communication with the radical gas generator 512 via at least one sampling conduit 530. Those skilled in the art will appreciate that the sampling conduit 530 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, in some embodiments the sampling conduit 530 may be configured to chemically react with the highly reactive atomic radicals, molecular radicals, and short-lived molecules contained within the radical gas stream flowing therein. In yet another embodiment, the sampling conduit 530 may consist of a catalytic material to facilitate the recombination of atomic gas species into its molecular gas species, such that the recombination energy of the atomic gas is released and measured. In other embodiments, the sampling conduit 530 may be configured to be chemically inert. In yet another embodiment, the sampling conduit 530 may consist of a catalyst material configured to facilitate the recombination of the radical species into its molecular gas species. Optionally, the sampling conduit 530 may include any variety of sensors, valves, heating elements, cooling elements, and the like thereon. In one embodiment, the sampling conduit 530 is coupled directly to and in fluid communication with the radical gas generator 512. In the illustrated embodiment the sampling conduit 530 is in fluid communication with the radical gas generator 512 via the reactive gas conduit 514. Optionally, the sampling conduit 530 may be in fluid communication with the sampling control valve 522 positioned on the reactive gas conduit 514. For example, the sampling control valve 522 may be configured to selectively direct a prescribed volume of reactive gas traversing through the reactive gas conduit 514 to the sampling module 532 via the sampling conduit 530. In another embodiment, the sampling control valve 522 may be configured to selectively direct a prescribed flow rate of reactive gas traversing through the reactive gas conduit 514 to the sampling module 532 via the sampling conduit 530. Further, any number of additional components, valves, sensors, and the like may be positioned anywhere along the sampling conduit 530. For example, in the illustrated embodiment at least one sensor and/or control device 550 may be positioned along the sampling conduit 530. Exemplary sensor devices include, without limitations, thermocouples, temperature sensors, optical sensors, UV, optical or infrared spectrometers, charge particle detectors, vacuum gauges, mass spectrometers, and the like. For example, in one embodiment the sensor device 550 comprises at least one thermistor. In another embodiment the sensor device 550 comprises at least one calorimetry system or device. An embodiment of a novel calorimetry system is discussed in detail and shown in FIGS. 8-15 of the present application. Optionally, the sensor device 550 may comprise one or more titration systems or devices. Those skilled in the arts will appreciate the sensor device 550 may comprise any number of in situ measuring devices were systems, flow valves, flowmeters, flow verifiers, and the like.

Referring again to FIG. 6, in the illustrated embodiment the sampling module 532 is coupled to at least one molecular compound stream conduit 534. Like the sampling conduit 530, the molecular compound stream conduit 534 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. One embodiment at least a portion of at least one of the sampling conduit 530 and/or the molecular compound stream conduit 534 may be configured to react with the radical gas stream flowing therein. For example, one embodiment at least a portion of the sampling conduit 530 and/or molecular compound stream conduit 534 may be configured to react with radicals within the gas flow to form chemical species more stable and capable of accurate measurement as compared to the radicals.

As shown in FIG. 6, at least one sensor module 536 is in fluid communication with the sampling module 532 via at least one molecular compound stream conduit 534. In one embodiment, the sensor module 536 may be configured to detect and measure the concentration of radicals in at least one gas flow. Any variety of devices or systems may be used within or to form the sensor module 536. For example, in one embodiment the sensor module 536 comprises at least one detector configured to measure the radical flux within the radical gas stream. In another embodiment, the sensor module 536 is configured to measure the concentration of at least one chemical species within a gas flow. For example, the sensor module 536 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment, the sensor module includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 536 may further include at least one titration system or device. In one embodiment, the sensing module 536 may be configured to reduce or eliminate recombination of the radicals within the gas stream into its molecular species. In another embodiment, the sensor module 536 may be configured to permit recombination of the radicals within a gas stream to its molecular species. At least one sensor module return conduit 535 may be in fluid communication with the sensor module 536 and the processing chamber 520. During use, the radical gas or similar material outputted from the sensing module 535 may be selectively directed to the processing chamber 520

As shown in FIG. 6, the processing system 510 may include at least one optional processor module 552 in communication with at least one component of the processing system 510. For example, in the illustrated embodiment, an optional processor module 552 is in communication with the radical gas generator 512 via at least one processor conduit 554. Further, the optional processor system 552 may be in communication with at least one of the optional sensor 550 via the processor conduit 554 and at least one optional sensor conduit 556, the sampling module 532 via the processor conduit 554 and at least one sampling conduit 558, and the sensor module 536 via at least one sensor module conduit 560. In one embodiment, the optional processor module 552 may be configured to provide and receive data from at least one of the radical gas generator 512, the optional sensor 550, the sampling module 532, and the sensor module 536. As such, the optional processor module 552 may be configured to measure the flows condition within the processing system 510 and selectively vary the operating conditions of the processing system 510 to optimize system performance. More specifically, the optional processor module 552 may be configured to measure the concentration of radicals and/or short-lived molecules within the radical stream and vary the operating characteristics of the radical generator 52 to increase or decrease the concentration of radicals within the radical gas stream. Further, the optional processor module 552 may be in communication with and provide/receive data from at least one of the optional valve device 522, sensor 524, and chamber processor module 520 via at least one optional processing conduit 564. Optionally, the processor 552 may be in communication with the various components of the processing system 510 wirelessly. Further, the processor 552 may be configured to store performance data, processing formulas and times, lot number, and the like. In addition, the processor 552 may be configured to communicate with one or more external processors via at least one computer network.

Optionally, as shown in FIG. 6, at least one analysis system or circuit 566 may be formed within the processing system 510. As shown, the analysis system 566 may include at least one of the sampling module 532, sensor module 536, optional sensor 550, optional processor module 552, and the like. Further, the analysis system 566 may further include valve device 522 or other devices and components within the processing system 510.

Figure 7:
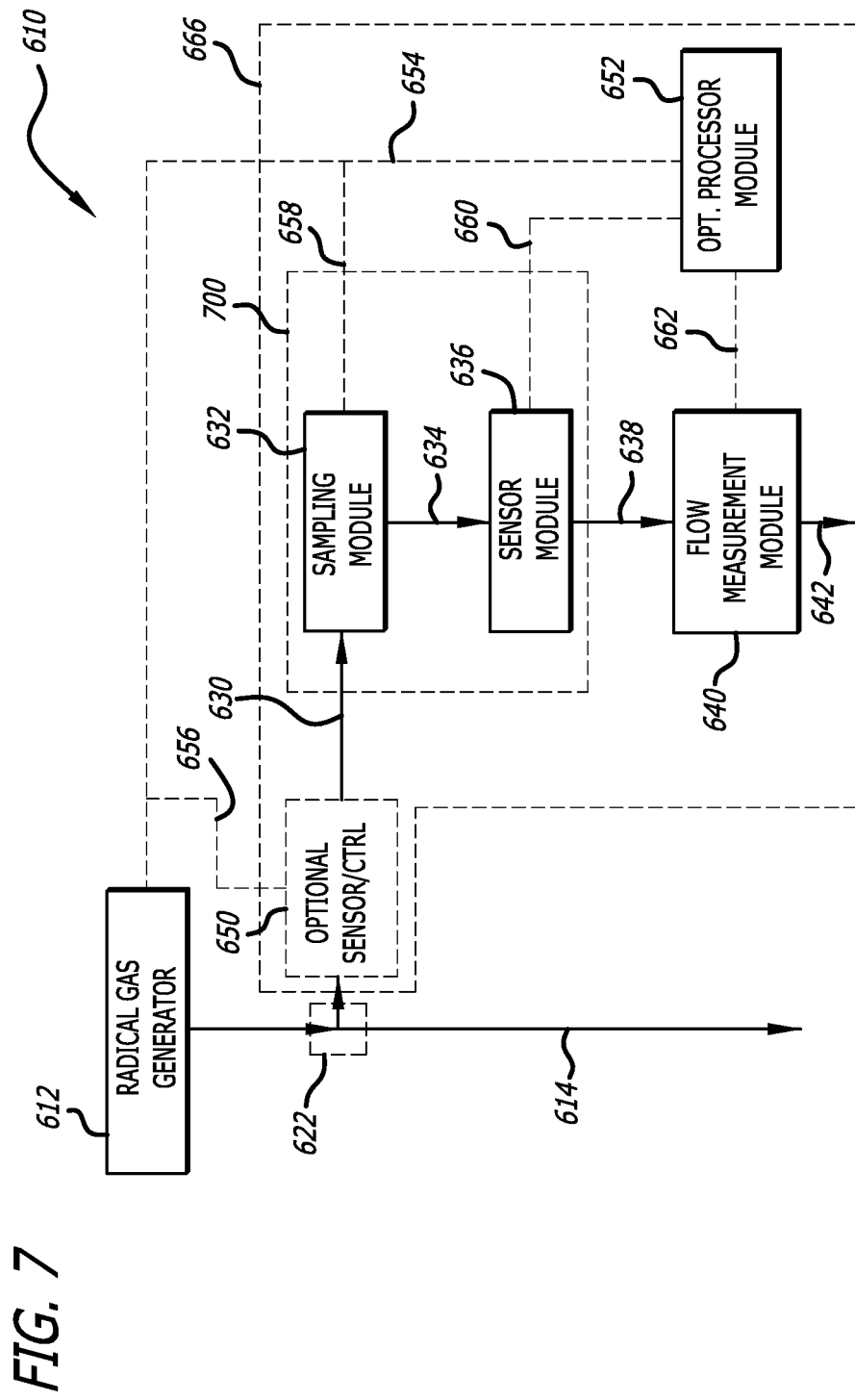
FIG. 7 shows a schematic diagram of another alternate embodiment of a multi-sensor gas sampling detection system.

Like the previous embodiments, FIG. 7 shows schematically an embodiment of a gas sampling detection system useful for detecting the concentration of radicals within a gas stream. As shown, the gas sampling detection system 610 includes at least one plasma generator and/or radical gas generator 612 in fluid communication with at least one gas passage 614. In one embodiment, the radical gas generator 612 is in communication with at least one sample gas source and at least one plasma source configured to energize and dissociate sample gases and generate at least one reactive gas stream. In one specific embodiment the radical gas generator 612 comprises a RF toroidal plasma source; although those skilled in the art will appreciate that any variety of plasma sources or radical gas sources may be used with the present systems. In one embodiment the radical gas generator 612 uses hydrogen ($H_2$) plasma to create atomic hydrogen. In another embodiment the radical gas generator 612 utilizes oxygen ($O_2$) plasma to create atomic oxygen. Optionally, the radical gas generator 612 may utilize nitrogen trifluoride ($NF_3$), fluorine ($F_2$), chlorine ($Cl_2$) or any variety of other materials to create a reactive plasma containing one or more radicals within the gas stream. Alternatively, radical gases may be generated by other gas excitation methods, including electron beam excitation, laser excitation, or hot-filament excitation. Further, the above description discloses various embodiments of RF-based plasma generation systems; although those skilled in the art will appreciate that any variety of alternate radical gas generation systems may be used with the present system. Exemplary alternate radical gas generation systems include, without limitation, glow discharge plasma systems, capacitively coupled plasma systems, cascade art plasma systems, inductively coupled plasma systems, wave heated plasma systems, arc discharge plasma systems, coronal discharge plasma systems, dielectric barrier discharge systems, capacitive discharge systems, Piezoelectric direct discharge plasma systems, and the like.

Referring again to FIG. 7, at least one reactive gas conduit 614 may be in fluid communication with the radical gas generator 612. In some applications, the reactive gas conduit 614 is manufactured from a chemically inert material or a material having low chemical reactivity. Exemplary materials include, without limitation, quartz, sapphire, stainless steel, strengthened steel, aluminum, ceramic materials, glass, brass, nickel, $Y_2O_3$, $YAlO_x$, various alloys, and coated metal such as anodized aluminum. In one embodiment, a single reactive gas conduit 614 is in fluid communication with a single radical gas generator 12. Like the previous embodiment, any number of reactive gas conduits 614 may be in communication with any number of radical gas generators 612. Further, optionally, the reactive gas conduit 614 may include one or more valve devices or systems, sensors, or similar devices 622 coupled thereto or in communication there with. For example, one or more valve devices 622 may be coupled to the reactive gas conduit 614 thereby permitting a user to selectively permit and/or restrict the flow of at least one reactive gas stream through the reactive gas conduit 614. The reactive gas conduit 614 may be coupled to or otherwise in communication with any variety of test systems, vessels, containers, processing fixtures and/or systems, and the like.

As shown in FIG. 7, at least one sampling module 632 may be in fluid communication with the radical gas generator 612 via at least one sampling conduit 630. Those skilled in the art will appreciate that the sampling conduit 630 may be manufactured from any variety of materials including, without limitations, stainless steel, alloys, aluminum, brass, ceramics materials, glass, polymers, plastics, carbon fiber carbon-based materials, graphite, silicon, silicon dioxide, silicon carbide, and the like. As such, in some embodiments the sampling conduit 630 may be configured to chemically react with the highly reactive atomic radicals, molecular radicals, and short-lived molecules contained within the radical gas stream flowing therein. In yet another embodiment, the sampling conduit 630 may consist of a catalytic material to facilitate the recombination of atomic gas species into its molecular gas species, such that the recombination energy of the atomic gas is released and measured. In other embodiments, the sampling conduit 630 may be configured to be chemically inert. In yet another embodiment, the sampling conduit 630 may consist of a catalyst material configured to facilitate the recombination of the radical species into its molecular gas species. Optionally, the sampling conduit 30 may include any variety of sensors, valves, heating elements, cooling elements, and the like thereon. In one embodiment, the sampling conduit 630 is coupled directly to and in fluid communication with the radical gas generator 612. In the illustrated embodiment the sampling conduit 630 is in fluid communication with the radical gas generator 612 via the reactive gas conduit 614. Optionally, the sampling conduit 630 may be in fluid communication with the sampling control valve 622 positioned on the reactive gas conduit 614. For example, the sampling control valve 622 may be configured to selectively direct a prescribed volume of reactive gas traversing through the reactive gas conduit 614 to the sampling module 632 via the sampling conduit 630. In another embodiment, the sampling control valve 622 may be configured to selectively direct a prescribed flow rate of reactive gas traversing through the reactive gas conduit 614 to the sampling module 632 via the sampling conduit 630. Further, any number of additional components, valves, sensors, and the like may be positioned anywhere along the sampling conduit 630. For example, in the illustrated embodiment, at least one sensor and/or control device 650 may be positioned along the sampling conduit 630. Exemplary sensor devices include, without limitations, thermocouples, temperature sensors, optical sensors, UV, optical or infrared spectrometers, charge particle detectors, vacuum gauges, mass spectrometers, and the like. For example, in one embodiment, the sensor device 650 comprises at least one thermistor. In another embodiment, the sensor device 650 comprises at least one calorimetry system or device. An embodiment of a novel calorimetry system is discussed in detail and shown in FIGS. 8-15 of the present application. Optionally, the sensor device 650 may comprise one or more titration systems or devices. Those skilled in the art will appreciate the sensor device 650 may comprise any number of in situ measuring devices were systems, flow valves, flowmeters, flow verifiers, and the like.

Referring again to FIG. 7, in the illustrated embodiment the sampling module 632 is coupled to at least one molecular compound stream conduit 634. Like the sampling conduit 630 the molecular compound stream conduit 634 may be manufactured from any variety of materials including, without limitation, graphite, silica, carbon fiber, silicon dioxide, silica and carbide, carbon-based materials, silica-based materials, stainless steel, alloys, aluminum, brass, ceramics materials, glass, polymers, plastics, and the like. One embodiment at least a portion of at least one of the sampling conduit 630 and/or the molecular compound stream conduit 634 may be configured to react with the radical gas stream flowing therein. For example, one embodiment at least a portion of the sampling conduit 630 and/or molecular compound stream conduit 634 may be configured to react with radicals within the gas flow to form chemical species more stable and capable of accurate measurement as compared to the radicals.

As shown in FIG. 7, at least one sensor module 636 is in fluid communication with the sampling module 632 via molecular compound stream conduit 634. In one embodiment, the sensor module 636 may be configured to detect and measure the concentration of radicals in at least one gas flow. Any variety of devices or systems may be used within or to form the sensor module 636. For example, in one embodiment the sensor module 636 comprises at least one detector configured to measure the radical flux within the radical gas stream. In another embodiment, the sensor module 636 is configured to measure the concentration of at least one chemical species within a gas flow. For example, the sensor module 636 may be configured to measure the concentration for carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds. In one specific embodiment the sensor module includes at least one optical gas imaging camera or device such as Fourier Transform Infrared spectroscopy system (hereinafter FTIR system), tunable filter spectroscopy system (hereinafter TFS system), mass spectrography, optical absorption spectroscopy and the like. Optionally, the sensing module 636 may further include at least one titration system or device. In one embodiment, the sensing module 636 may be configured to reduce or eliminate recombination of the radicals within the gas stream into its molecular species. In another embodiment the sensor module 636 may be configured to permit recombination of the radicals within a gas stream to its molecular species.

Referring again to FIG. 7, at least one sensor module output conduit 638 is in fluid communication with the sensor module 636 and the flow measurement and/or flow control module 640. In some embodiments, the flow measurement module 640 is configured to accurately measure a portion of the gas stream flowing there through. For example, the flow of the gas stream may be measured using a mass flow verifier (MFV). In another embodiment, the flow of the gas stream may be measured using a mass flow meter (MFM). Optionally, the flow may be determined by measuring the pressure differential between an orifice of known size within the multi-sensor gas sampling detection system 610 with the fluid conductance. Those skilled in the art will appreciate that any variety of flow measuring devices or systems may be used with the gas sampling detection system 610 disclosed herein. As shown in FIG. 7, at least one exhaust conduit 642 may be coupled to or in communication with the flow measurement module 640 and configured to exhaust the radical gas stream from the gas sampling detection system 610. Optionally, the exhaust conduit 642 may be in fluid communication with at least one vacuum source (not shown).

As shown in FIG. 7, the processing system 610 may include at least one optional processor module 652 which may be in communication with at least one component of the processing system 610. For example, in the illustrated embodiment, an optional processor module 652 is in communication with the radical gas generator 612 via at least one processor conduit 654. Further, the optional processor system 652 may be in communication with at least one of the optional sensor 650 via the processor conduit 654 and at least one optional sensor conduit 656, the sampling module 632 via the processor conduit 654 and at least one sampling conduit 658, the sensor module 636 via at least one sensor module conduit 660, and the flow measurement module 640 via at least one flow measurement conduit 662. In one embodiment, the optional processor module 652 may be configured to provide and receive data from at least one of the radical gas generator 612, the optional sensor 650, the sampling module 632, the sensor module 636, and the flow measurement module 640. As such, the optional processor module 652 may be configured to measure the flow conditions within the processing system 610 and selectively vary the operating conditions of the processing system 610 to optimize system performance. More specifically, the optional processor module 652 may be configured to measure the concentration of radicals within the gas stream vary the operating characteristics of the radical gas generator 612 to increase or decrease the concentration of radicals within the radical gas stream. Further, the optional processor module 652 may be in communication with and provide/receive data from at least one of the optional valve device 622, and sensor 624. Optionally, the processor 652 may be in communication with the various components of the processing system 610 wirelessly. Further, the processor 652 may be configured to store performance data, processing formulas and times, lot number, and the like. In addition, the processor 652 may be configured to communicate with one or more external processors via at least one computer network.

Optionally, as shown in FIG. 7, at least one analysis system or circuit 666 may be formed within the processing system 610. As shown, the analysis system 666 may include at least one of the sampling module 632, sensor module 636, flow measurement module 649, optional sensor 650, optional processor module 652, and the like. Further, the analysis system 666 may further include valve device 622 or other devices and components within the processing system 610.

Figure 8:
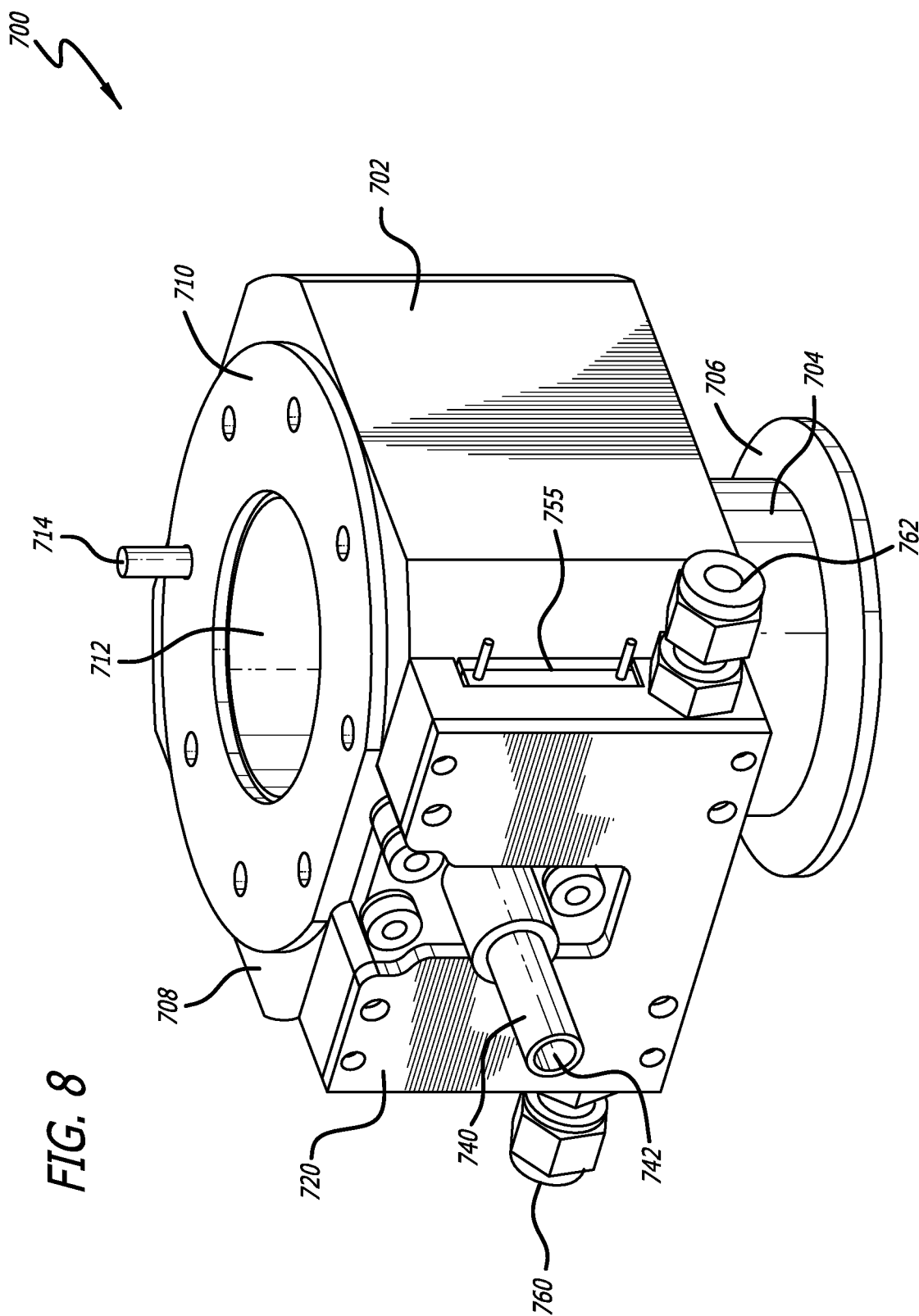
FIG. 8 shows an elevated perspective view of an embodiment of a sampling reaction module for use in a multi-sensor gas sampling detection system.
Figure 9:
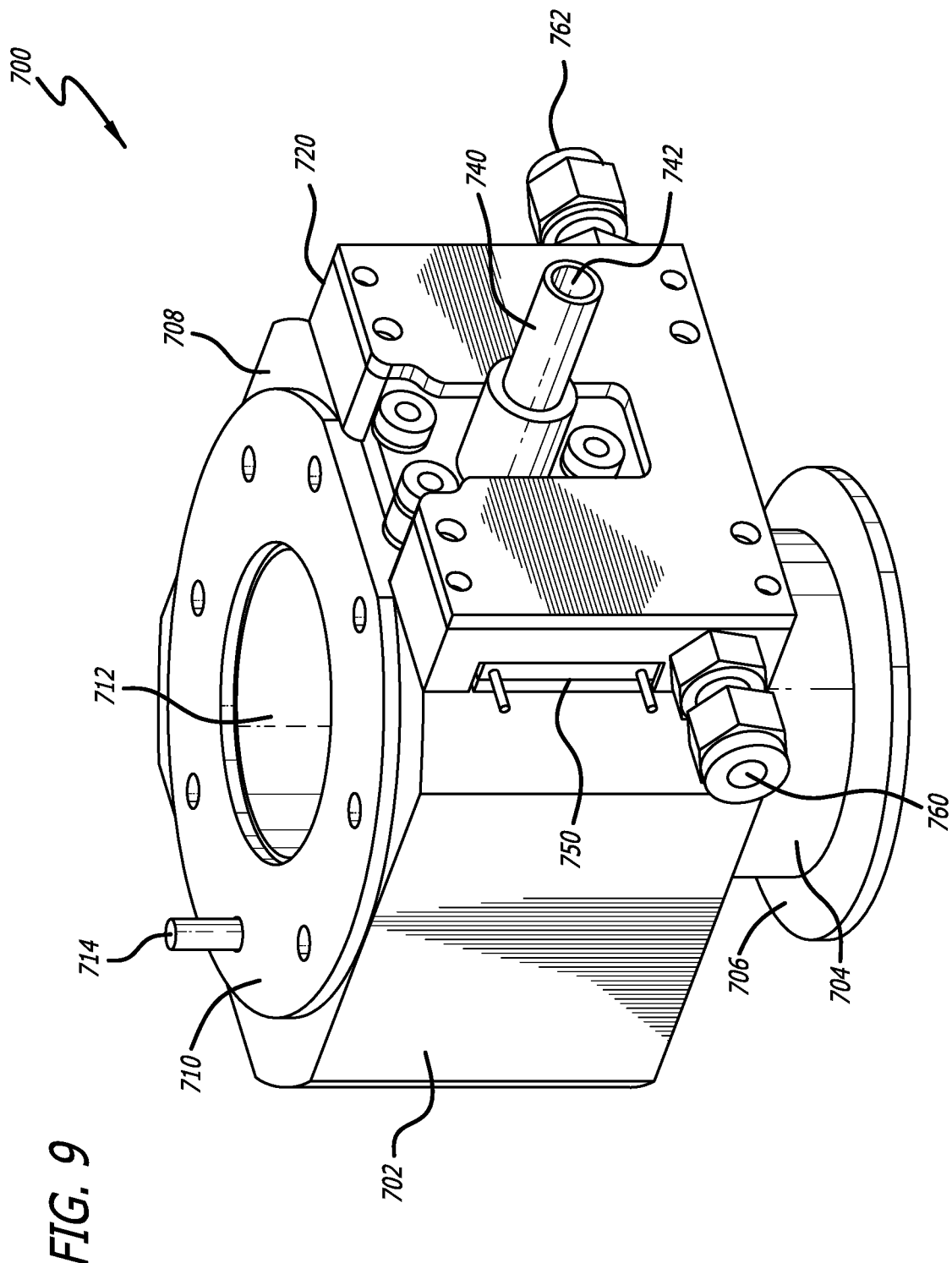
FIG. 9 shows an alternate elevated perspective view of an embodiment of the sampling reaction module for use in a multi-sensor gas sampling detection system shown in FIG. 1.
Figure 10:
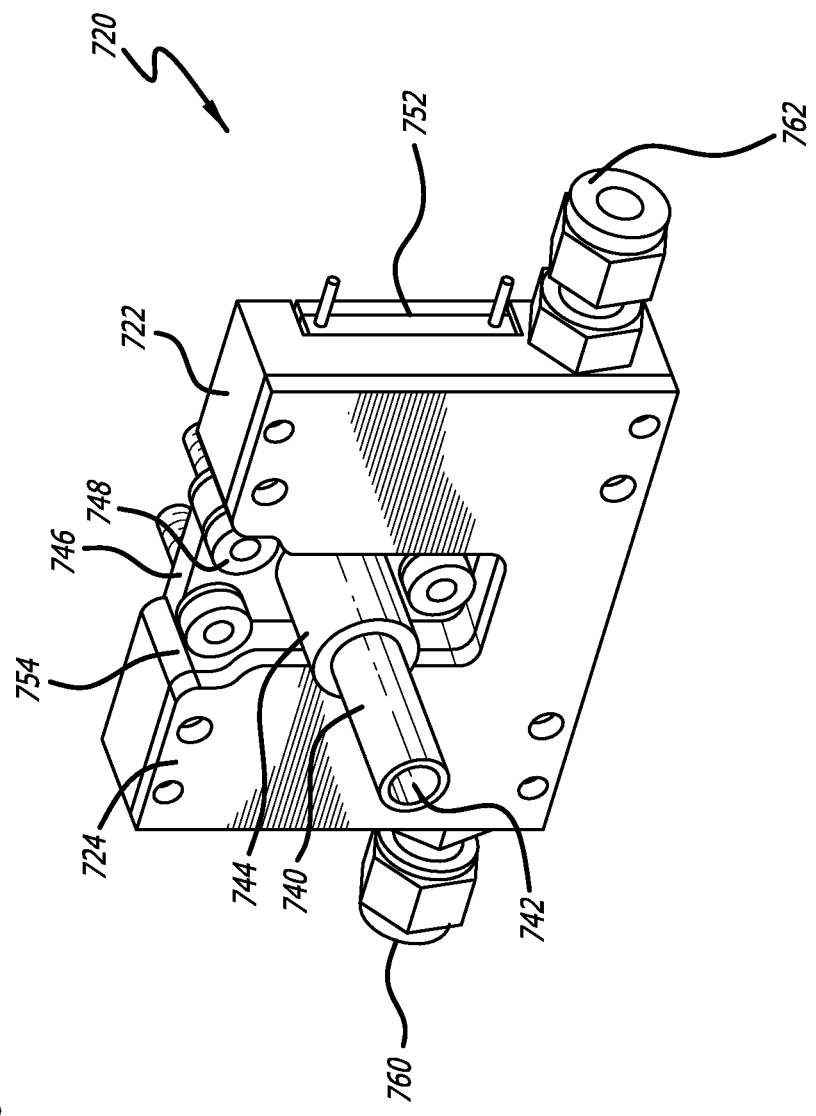
FIG. 10 shows an elevated frontal perspective view of an embodiment of an analysis fixture used with the sampling reaction module shown in FIG. 1.
Figure 11:
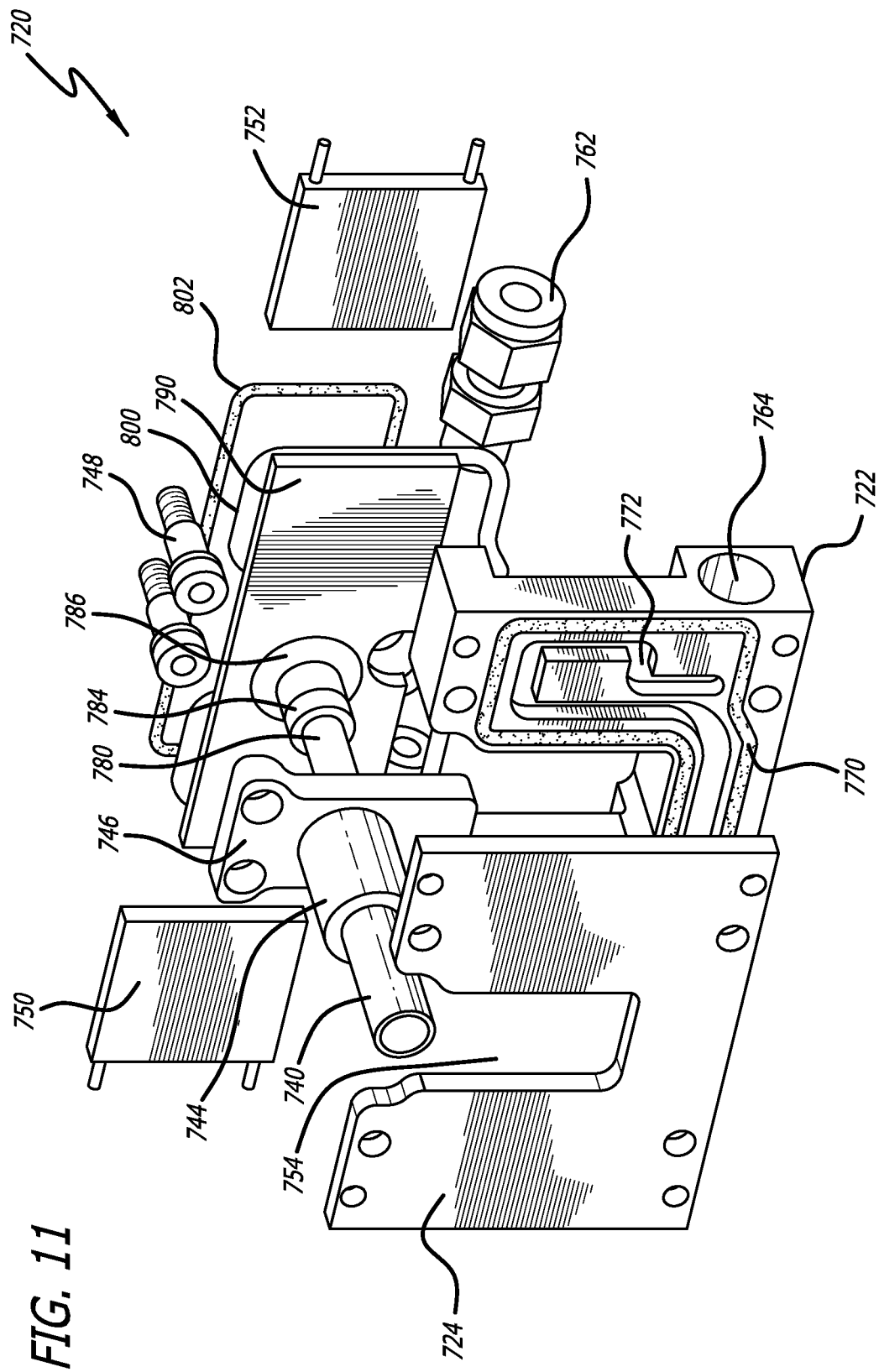
FIG. 11 shows an elevated frontal exploded view of the embodiment of an analysis fixture used with the sampling reaction module shown in FIG. 1.

As stated above, the various embodiments of the processing system disclosed in FIGS. 1-7 include at least one sampling module and at least one sensor module. Optionally, as shown in FIGS. 1-7, portions of the sampling module and sensor module may be combined in a single unit or device. For example, as shown in FIG. 1 the sampling module 32 and sensor module 36 may be combined in at least one sampling reaction module 700. FIGS. 1-7 show various embodiments of processing systems having at least one sampling reaction module 700 therein. In the illustrated embodiments the sampling modules and sensor modules are included within the sampling reaction module 700. Optionally, portions of the sampling modules and portions of the sensor modules may be included within the sampling reaction module 700. FIGS. 8 and 9 show various views of an embodiment of a sampling reaction module 700 configured for use with the processing systems disclosed herein, while FIGS. 10-15 show various views of the components forming the sampling reaction module 700. Further, those skilled in the art will appreciate that the sampling reaction module 700 may be used in any variety of systems. Optionally, the processing systems disclosed herein may be operated without the inclusion of the sampling reaction module 700.

As shown in FIGS. 8 and 9 the sampling reaction module 700 includes at least one module body 702 having at least one coupling body 704 extending therefrom. At least one coupling body flanged 706 may be positioned on the coupling body 704. The module body 702 further includes at least one coupling surface 708 having at least one coupling flanged 710 formed thereon. At least one vacuum passage 712 may be formed in the coupling surface 708 proximate to the coupling flanged 710. One or more coupling devices 714 may be positioned anywhere on the module body 702. In one embodiment, the module body 702 is manufactured from stainless steel. In another embodiment the module body 702 is manufactured from brass. Still another embodiment the module body 702 is manufactured from copper. Optionally, the module body 702 may be manufactured from any variety of materials including, without limitations, aluminum alloys, copper alloys, tungsten alloys, tungsten, metallic alloys, ceramics, and similar materials.

Referring again to FIGS. 8 and 9, at least one analysis fixture 720 may be positioned on or otherwise coupled to the module body 702. At least one coupling body 740 defining at least one coupling passage 742 may extend from the module body 702. In the illustrated embodiment at least one fluid inlet port 760 and at least one fluid outlet port 762 may be positioned on or otherwise in communication with the analysis fixture 720. One or more thermal control modules 750, 752 may be positioned proximate to at least one of the module body 702 in the analysis fixture 720. The various features and components of the module body 702 and the analysis fixture 720 will be described in greater detail in the following paragraphs.

FIGS. 10-13 show various views of the elements forming the analysis fixture 720. As shown, the analysis fixture 720 includes at least one analysis fixture body 722 having at least one analysis fixture cover plate 724 position thereon. In the illustrated embodiment the analysis fixture cover plate 724 is selectively detachable from the analysis fixture body 722; although those skilled in the art will appreciate that the analysis fixture cover plate 724 need not be separable from the analysis fixture body 722. The coupling body 740 having at least one coupling passage 742 included therein may also include at least one coupling passage support 744 extending from at least one passage mount mounting plate 746. One or more fasteners 748 may traverse through the passage mounting plate 746 and be configured to couple at least a portion of the analysis fixture 720 to the module body 702 (see FIGS. 5-6).

As shown in FIGS. 10-13, one or more thermal control modules 750, 752 may be positioned proximate to the analysis fixture 720. In one embodiment, the thermal control modules 750, 752 comprise thermoelectric modules configured to regulate the temperature of the sampling tube 780 within the analysis fixture 720. In another embodiment, the thermal control modules 750, 752 may comprise at least one thermistor or similar device. As such, the thermal control modules 750, 752 may include a variety of heating and cooling devices. Optionally, any variety of temperature regulating devices, fixtures, components, or devices may be used with the analysis fixture 720. In the illustrated embodiment to thermal control modules 750, 752 are used to regulate the temperature of various components of the analysis fixture 720 which in turn may regulate the temperature of the radical gas stream under analysis. In one embodiment thermal control modules 750, 752 may be in communication with at least one optional processor module used in the processing system (see FIGS. 1-7, ref. no. 52, 152, 252, 382, 452, 552, and 652, respectively).

Referring again to FIGS. 10-13, at least one connector relief 754 may be formed in at least one of the analysis fixture body 722 and the analysis fixture cover plate 724. As shown, at least one sampling tube 780 may be positioned within the coupling body 740. Further, the sampling tube 780 may be positioned proximate to the thermal control modules 750, 752. In one embodiment the sampling tube 780 is manufactured from at least one chemically reactive material. For example, in one embodiment at least a portion of the sampling tube 780 is manufactured from carbon, graphite, silica, carbon fiber, silicon dioxide, silica and carbide, carbon-based materials, silica-based materials, and the like. As such, at least a portion of the sampling tube 780 may be configured to react with radicals contained within the radical gas stream flowing through the sampling tube passage 782 formed within the sampling tube 780, thereby forming chemical species such as carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds which may be more easily detected and whose concentrations can be easily measured. Optionally, the sampling tube 780 may be manufactured from any variety of chemically inert materials such as stainless steel, ceramics, aluminum, various alloys, and the like. Similarly, the coupling body 740 may be manufactured from any variety of materials. In the illustrated embodiment, the coupling body 740 is manufactured from a substantially chemically inert material such as stainless steel while sampling tube 780 is manufactured from a chemically reactive material such as silicon carbide. As such, the coupling body 740 may be manufactured from chemically inert or chemically reactive materials.

In one embodiment, the sampling tube 780 is thermally isolated from the surrounding environment. For example, the sampling tube 780 may be positioned within the coupling body 740. A vacuum may be maintained within the void between the connection tube 740 and the sampling tube 780 thereby thermally isolating the sampling tube 780 from the environment. Optionally, the sampling tube 780 may be manufactured in any variety of diameters, lengths, and/or transverse dimensions.

As shown in FIGS. 10-13, one or more seal devices or members may be positioned on or proximate to sampling passage 780. In the illustrated embodiment, at least one seal device 784 is positioned on the sampling tube 780 and configured to isolate the sampling tube 780 from the coupling body 740. In one embodiment, the seal device 784 is configured to minimize the conduction of heat between the connection body 740 and the sampling tube 780. Further, at least one seal member 786 is positioned on or near the sampling tube 780 proximate to at least one plate member 790. In one embodiment, the seal member 786 comprises at least one crush seal although those skilled in the art will appreciate the any variety of seal members may be used.

Referring again to FIGS. 10-13, the fluid inlet port 760 and fluid outlet port 762 may be in communication with one or more fluid port receivers 764 formed in the analysis fixture body 722. One or more fluid channels 772 may be in fluid communication with the fluid inlet port 760 and the fluid outlet port 762 via the fluid port receivers 764. During use, one or more fluids may be directed through the fluid inlet port 760, fluid channel 772, and fluid outlet port 762. As such, various fluids may be directed through the analysis fixture body 722 to selectively control the temperature of the analysis fixture 720 in the radical gas stream flowing proximate thereto. Further, optionally, at least one seal member 770 may be positioned proximate to the fluid channel 772.

As shown in FIGS. 10-13, the plate member 790 may be positioned proximate to the thermal control modules 750, 752. In one embodiment, the plate member 790 is configured to position the thermal control modules 750, 752 proximate to the sampling tube 780 and the analysis fixture body 722. In one embodiment, at least one seal body 800 and/or at least one interface seal body 802 may be positioned on or proximate to the plate member 790. As shown, the plate member 790 may include at least one sampling tube orifice 804 configured to have at least a portion of the sampling tube 780 traverse there through.

Figure 12:
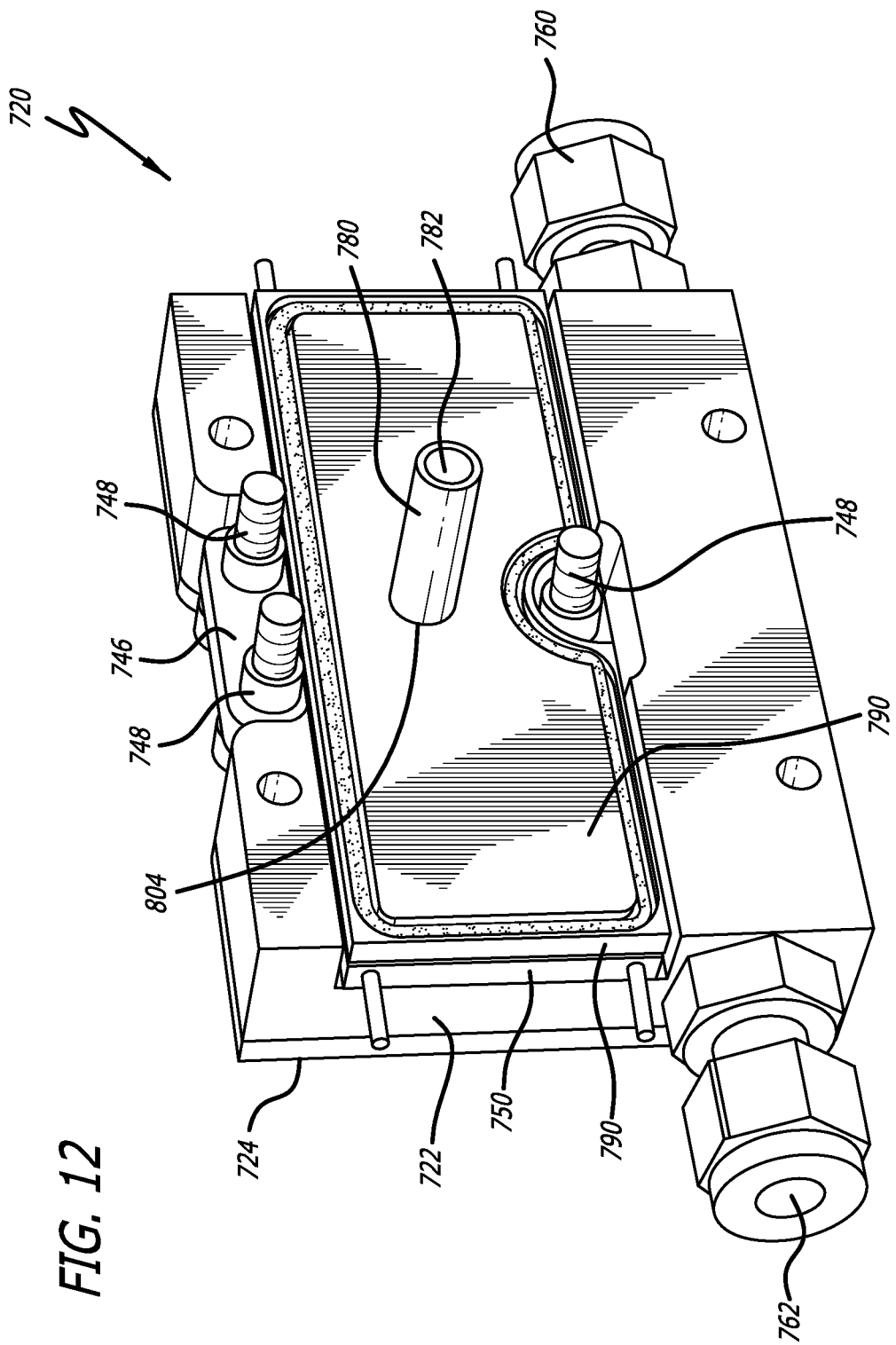
FIG. 12 shows an elevated posterior perspective view of an embodiment of an analysis fixture used with the sampling reaction module shown in FIG. 1.
Figure 13:
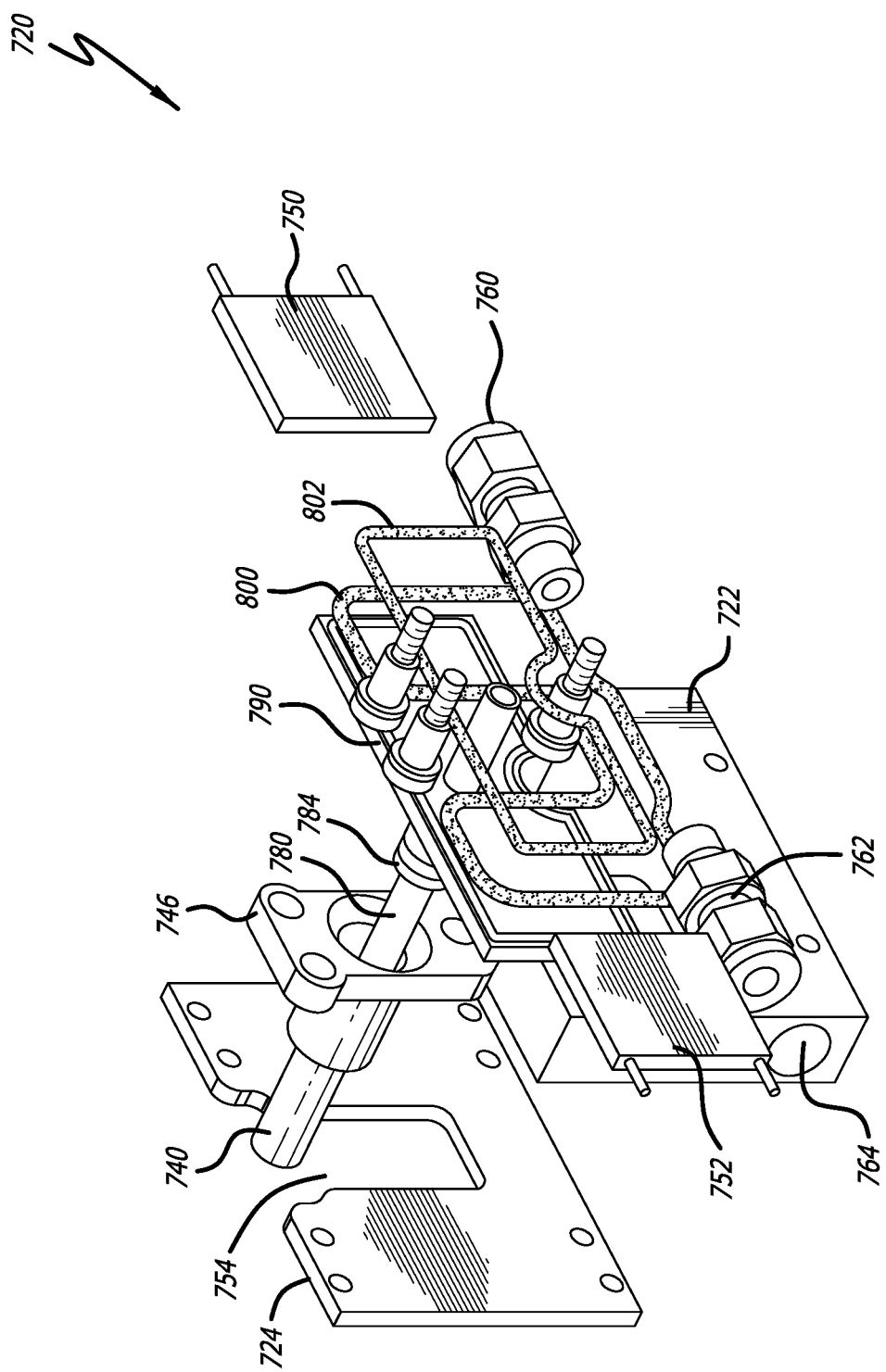
FIG. 13 shows an elevated posterior exploded view of the embodiment of an analysis fixture used with the sampling reaction module shown in FIG. 1.
Figure 14:
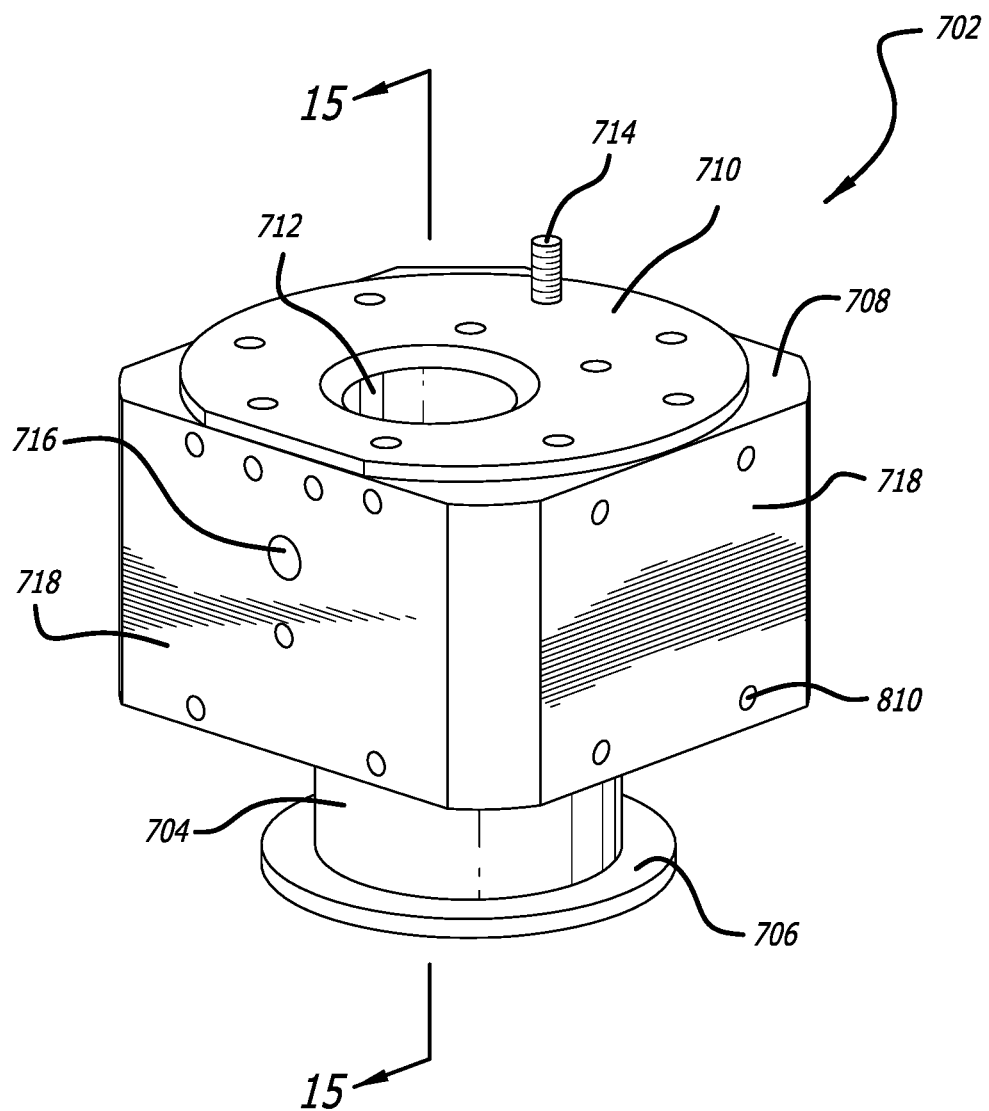
FIG. 14 shows an elevated perspective view of an embodiment of a sampling reaction module body.
Figure 15:
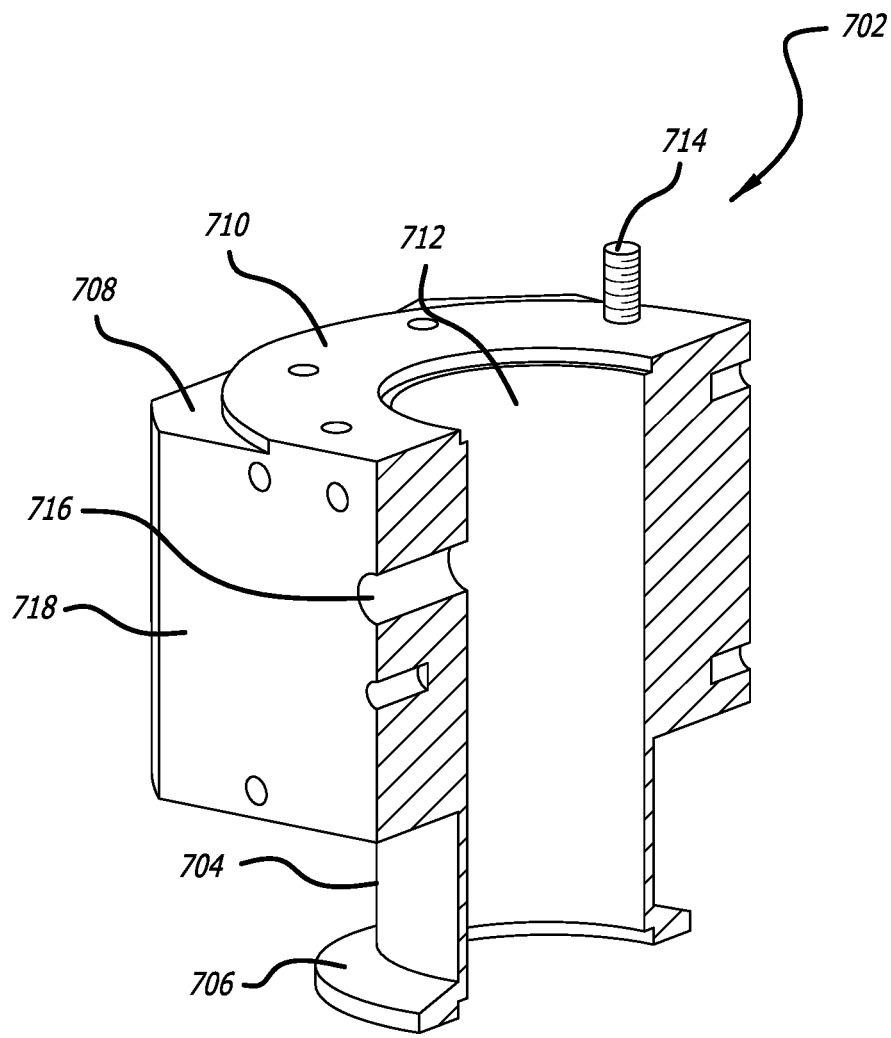
FIG. 15 shows an elevated cross-sectional perspective view of an embodiment of the sampling reaction module body shown in FIG. 14 viewed along the line 15-15.

FIGS. 14 and 15 show various views of the module body 702 for use with their sampling reaction module 700. As shown, the module body 702 includes at least one module body face 718. Optionally, at least one fastener receiver may be formed on at least one module body face 718. In one embodiment, the module body face 718 may be configured to receive at least one cooling element, body, and/or feature (not shown) thereon or formed therein. For example, in one embodiment cooling elements or fins configured to increase the surface area of the module body 702 may be formed on the face of at least one module body face 718. Further, the module body face 718 may include at least one sampling tube receiver 716 configured to receive at least a portion of the sampling tube 780 therein (see FIGS. 10-13). As shown in FIG. 12, at least a portion of the sampling tube receiver 716 is in fluid communication with at least a portion of the vacuum passage 712 formed in the module body 712. During use, the vacuum passage 712 is coupled to or otherwise in fluid communication with a vacuum source (not shown). As such sampling tube receiver 716 is in fluid communication with the vacuum formed within the vacuum passage 712.

Figure 16:
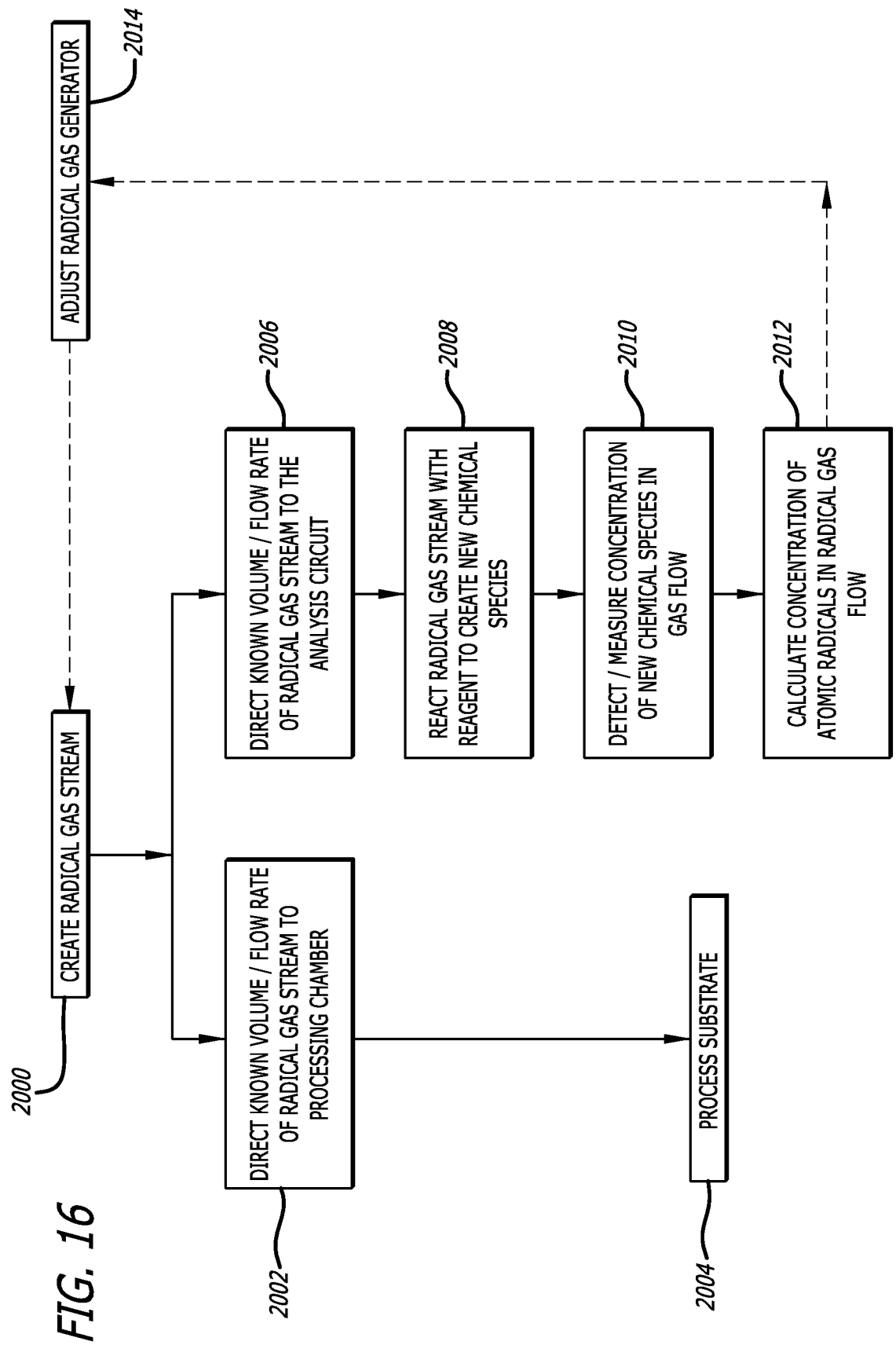
FIG. 16 shows a flow diagram describing a method of using the multi-sensor gas sampling detection system described in FIGS. 1-7.

The present application also discloses various methods of measuring the concentration of radicals in a radical gas stream. FIG. 16 shows a general flowchart of the measurement process when used with the processing system 10 shown in FIG. 1, although those skilled in the art will appreciate that the process disclosed herein may be easily adapted for use with the various embodiments of the processing systems shown in FIGS. 2-7. As shown, a radical gas stream is created, denoted by reference number 2000 in FIG. 16. Typically, the radical gas stream is generated by the radical gas generator 12 shown in FIG. 1. Thereafter, a known volume and/or flow rate of the radical gas stream is directed to at least one analyzing circuit 66, denoted by reference number 2006 in FIG. 16, while the remaining portion of the radical gas stream is directed to the processing chamber 16, denoted by reference number 2002, and used to process at least one substrate or otherwise used within the processing chamber, denoted by reference number 2004. The known volume and/or flow rate of radical gas within the analyzing circuit 66 is reacted, denoted by reference number 2008 in FIG. 16, with a reagent to create a new, more easy-to-detect/measure chemical species or molecules, or, in the alternative, to recombine back to its molecular species. Exemplary reagents are shown below and include, without limitation: Ni, Al, W, Cu, Co, Zn, C, quartz, alumina, organic carbo-hydrate containing materials and various associated oxides, nitrides, and the like.

Optionally, one or more reaction sources 472 may be used to provide one or more reagents, reactive materials, and/or excitation energy to the sample module 432 to react the radical gas stream to create a new, more easy-to-detect/measure chemical species or molecules (See FIG. 5). Typically, the reagent is reacted with the radical gas stream within proximate to the sampling module 32 to create a compound stream. Thereafter, the compound stream may be directed into the sensor module 36 which measures the concentration of the new chemical species or molecules within the compound stream, denoted by reference number 2010 in FIG. 16. Thereafter, the concentration of radicals within the processing chamber may be calculated, denoted by reference number 2012 in FIG. 16, by comparing the ratio of the concentration of chemical species within the compound stream per defined volume of the radical gas stream forming the sampling gas stream to the remaining volume of the at least one radical gas stream. Optionally, the optional processor module 52 may be configured to receive data sensor module 36 and selectively adjust the radical gas generator to optimize the concentration of radicals within a radical gas stream, denoted by reference number 2014 in FIG. 16. Optionally, as shown in FIG. 6, the radical gas stream 535 from the sensor module 536 may be directed to the processing chamber 520. In another embodiment, those skilled in the art will appreciate that the measurement systems and methods disclosed herein may be used to measure the concentration of atomic radicals, molecular radicals, and other short-lived molecules in any variety of applications. As such, the measurement systems described herein need not include or be coupled to a processing chamber 16 (See FIG. 1). For example, FIG. 7 shows an embodiment of a measurement system 610 wherein the processing chamber has been eliminated. As such, the measurement systems described herein may be used in any variety of application wherein in situ measurement of atomic radicals, molecular radicals, and/or other short-lived molecules is desired.

Figure 17:
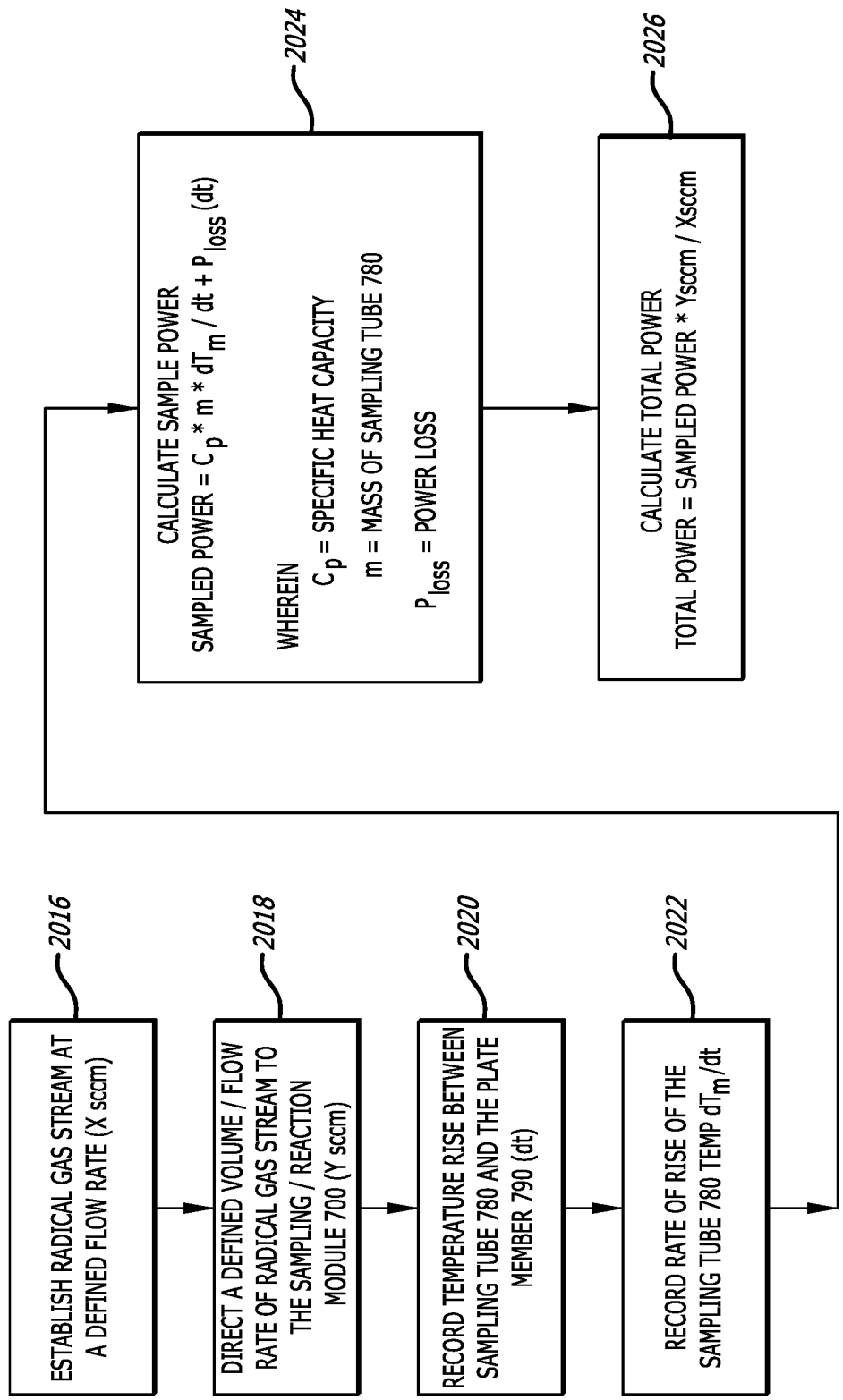
FIG. 17 shows a flow diagram describing a method of using the multi-sensor gas sampling detection system described in FIGS. 1-7.

As stated above, the sampling reaction module 700 shown in FIGS. 1-15 may be used to determine the concentration of atomic radicals, molecular radicals, short-lived molecules, and other difficult-to-measure molecules or compounds in situ. In one embodiment, the multi-sensor gas sampling detection systems disclosed herein may be configured to use calorimetry to determine the concentration of molecules or other compounds within a gas stream wherein the recombination reaction is measured using the sampling reaction module 700. FIG. 17 shows a flow chart of one calorimetry-based method utilizing the sampling reaction module 700 shown in FIGS. 1 and 8-15. In this embodiment, a flow of a radical gas stream is established within the multi-sensor gas sampling detection system 10 as a defined flow rate (X sccm), as denoted by reference number 2016. Thereafter, a define flow rate (Y sccm) or volume of the radical gas stream is directed to the sampling reaction module 700 (see reference number 2018 in FIG. 17). The flow of the radical gas stream through the sampling reaction module 700 results in the temperature of the sampling tube 780 increasing (or decreasing in some circumstances) in relation to the temperature of the plate member 790 (hereinafter dT), which is recorded (see reference number 2020). Further, the rate of temperature variation between the sampling tube 780 and the plate member 790 ($dT_m/dt$) is noted (see reference number 2022). Thereafter, as denoted as reference number 2024 in FIG. 17, the calculated sample power may be calculated as follows:

$$\text{Sampled power} = C_p * m * dT_m/dt + P_{loss}(dT)$$

Wherein: $C_p$=specific heat capacity
m=mass of sampling tube
$P_{loss}$=power loss As shown in FIG. 17, reference number 2026, the total power may be calculated as follows:

$$\text{Total power} = \text{Sampled power} * Y sccm/X sccm$$

Figure 18:
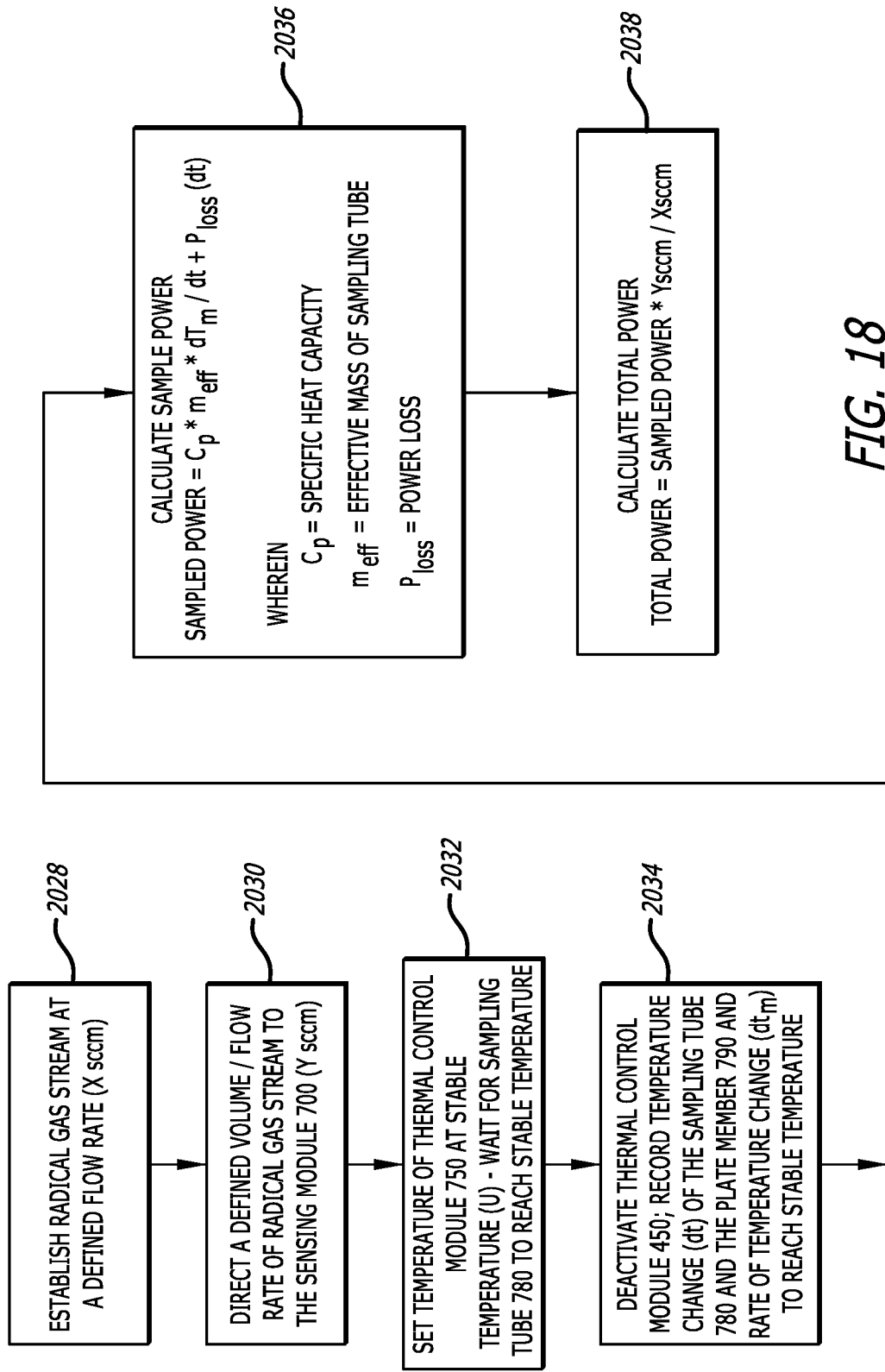
FIG. 18 shows a flow diagram describing an alternate method of using the multi-sensor gas sampling detection system described in FIGS. 1-7.

In another embodiment, the multi-sensor gas sampling detection systems disclosed herein may be configured to use an alternate calorimetry to determine the concentration of molecules or other compounds within a gas stream. FIG. 18 shows a flow chart of an alternate calorimetry-based method utilizing a pre-calibrated curve determines the function $P_{loss}$ of components of the sampling reaction module 700 shown in FIGS. 1 and 8-15. Like the previous embodiments, a radical gas steam flow is established as denoted by reference number 2028. A defined volume, flow rate, or portion of the radical gas steam is directed to at least one sensing unit or device (see reference number 2030). The thermal control module 750 is activated and the time for the sampling tube 780 to reach a stable temperature is observed (see reference number 2032). As such, the recombination reaction is measured at the fixed sampling tube temperature (U) degrees. In addition, to calculate the sampled power, the mass of the sampling tube 780 is no longer determined by the entire mass of the sampling tube, but rather only a fraction of the mass of the sampling tube 780, denoted as the effective mass $m_{eff}$. As a result, the response time of the sampling reaction module 700 is now faster due to a smaller thermal mass. The total power may be calculated based on the sample power.

During use, the sampling tube 780 is heated to a higher temperature (U) (reference number 2032) and then allowed to cool to its steady state temperature (see reference number 2034). Thereafter, a pre-calibration curve may be established based on the observed thermal characteristics of the sampling reaction module 700. Once the pre-calibration curve has been established a defined flow rate (X sccm) of a radical gas is established. A defined flow rate (Y sccm) or volume of radical gas is directed into the sampling reaction module 700. The thermal control module 750 of the sampling reaction module 700 is set to a prescribed temperature. Thereafter, the thermal control module 750 is deactivated and the temperature change to a stable temperature (dT) and rate of temperature change ($dt_m$) between the sampling tube 780 and the plate member 790 is recorded (reference number 2034).

Thereafter, the calculated sample power may be calculated (reference number 2036) as follows:

$$\text{Sampled power} = C_p * m_{eff} * dT_m/dt + P_{loss}(dT)$$

Wherein: $C_p$=specific heat capacity
$m_{eff}$=effective mass of sampling tube
$P_{loss}$=power loss The total power (reference number 2038) may be calculated as follows:

$$\text{Total power} = \text{Sampled power} * Y sccm/X sccm$$

Figure 19:
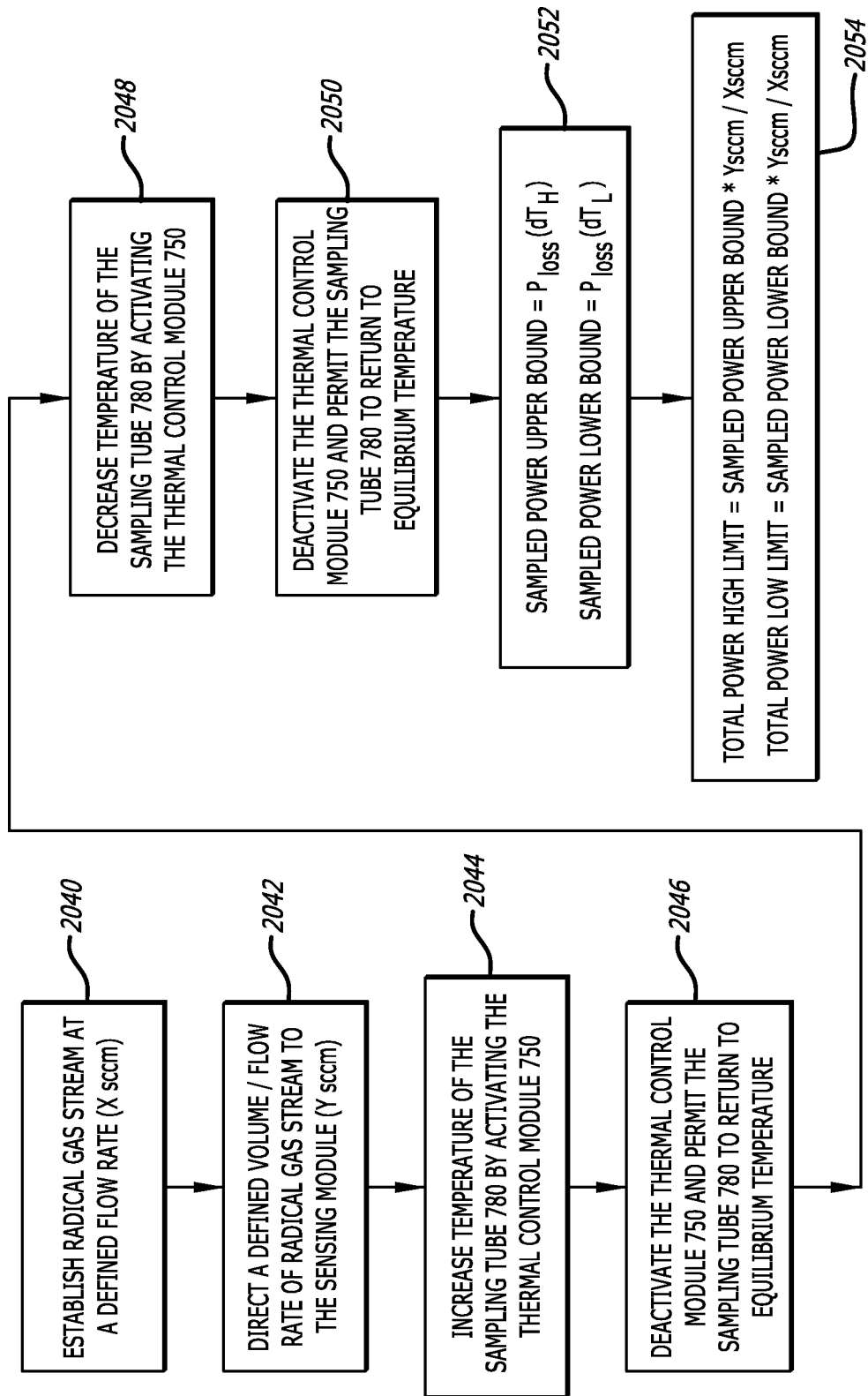
FIG. 19 shows a flow diagram describing an another method of using the multi-sensor gas sampling detection system described in FIGS. 1-7.

FIG. 19 shows a flow chart of another method of utilizing the sampling reaction module 700 shown in FIGS. 1 and 8-15 wherein the recombination reaction is measured at the fixed sampling tube temperature. In this embodiment, a flow radical gas stream is established (reference number 2040) within the multi-sensor gas sampling detection system 10 as a defined flow rate (X sccm). Thereafter, a defined flow rate (Y sccm) or volume of the radical gas stream is directed to the sampling reaction module 700 (reference number 2042). Thereafter, the temperature of the sampling tube 480 is selectively increased using the thermal control module 750 of the sampling reaction module 700 (reference number 2044). Once the sampling tube 780 reaches a prescribed high temperature ($dT_H$) the thermal control module 750 is deactivated, thereby permitting the sampling tube 780 to return to an equilibrium temperature (reference number 2046). Thereafter, the temperature of the sampling tube 480 is selectively decreased using the thermal control module 750 of the sampling reaction module 700 (reference number 2048). Once the sampling tube 780 reaches a prescribed low temperature ($dT_L$) the thermal control module 750 is deactivated, thereby permitting the sampling tube 780 to return to an equilibrium temperature (reference number 2050).

Thereafter, the calculated sample high limit power and low limit power may be calculated (reference number 2052) as follows:

$$\text{Sampled power high limit} = P_{loss}(dT_H)$$

$$\text{Sampled power low limit} = P_{loss}(dT_L)$$

Wherein: $P_{loss}$=power loss
The upper and lower bound of the reaction may be calculated as follows (reference number 2054):

$$\text{Total power upper bound} = \text{Sampled power high limit} * Y sccm/X sccm$$

$$\text{Total power lower bound} = \text{Sampled power low limit} * Y sccm/X sccm$$

The upper and lower bounds determine the error limits of the actual reaction.

Figure 20:
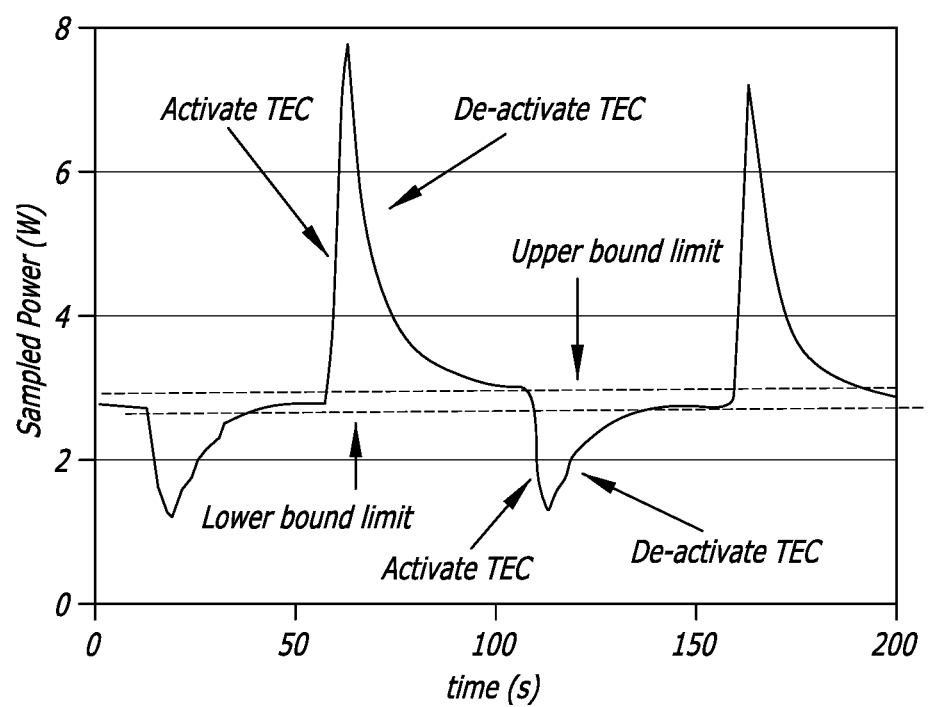
FIG. 20 shows graphically the method of using the multi-sensor gas sampling detection system described in FIG. 19 to establish the upper bound limit and lower bound limit.

FIG. 20 shows graphically an example of the process flow described in FIG. 19 above. As shown, the thermal control module 750, referred to as the TEC in FIG. 20 is activated to obtain the upper bound of the process and de-activated to obtain the lower bound of the process.

Figure 21:
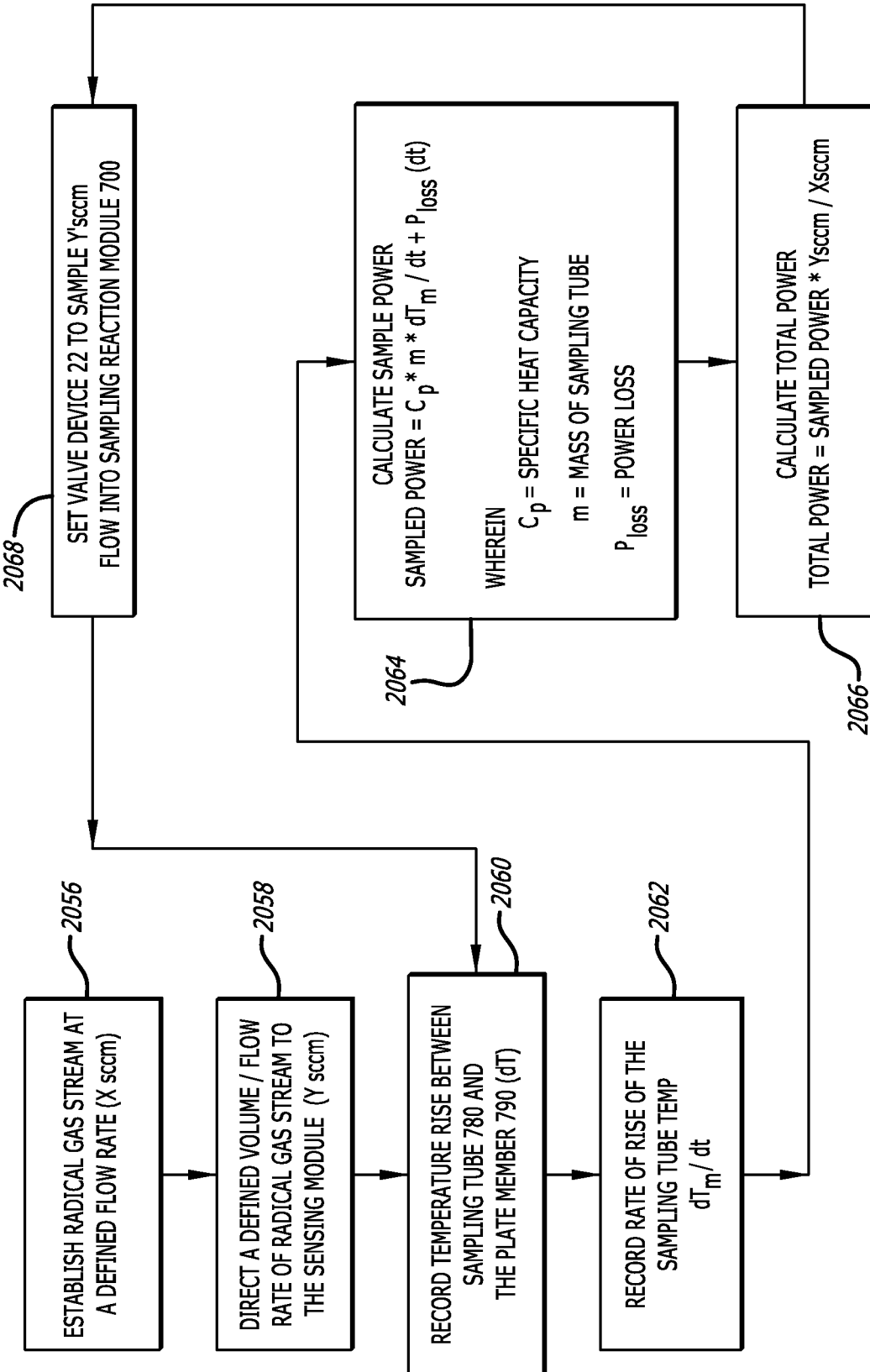
FIG. 21 shows a flow diagram describing a method of calibrating the multi-sensor gas sampling detection system described in FIGS. 1-7.

In some instances, determination of the sampled power may require further calibration as distinguishing between the heat generated from the radicals recombination as opposed to from the hot gas of the plasma source is difficult. As such, FIG. 21 shows a calibration process configured to distinguishing between the heat generated from the radicals recombination as opposed to from the hot gas of the plasma source. As shown, a defined flow rate (X sccm) of a radical gas is established (reference number 2056). Thereafter, a defined flow rate (Y sccm) or volume of the radical gas stream is directed to the sampling reaction module 700 (reference number 2058). The flow of the radical gas stream through the sampling reaction module 700 results in the temperature of the sampling tube 780 increasing or decreasing in some circumstances) in relation to the temperature of the plate member 790 (hereinafter dT). The change in temperature of the sampling tube 780 and plate member 790 is recorded (reference number 2060). Further, the rate of temperature variation between the sampling tube 780 and the plate member 790 ($dT_{m/dt}$) is noted (reference number 2062). Thereafter, the calculated sample power may be calculated (reference number 2064) as follows:

$$\text{Sampled power} = C_p * m * dT_m/dt + P_{loss}(dT)$$

Wherein: $C_p$=specific heat capacity
m=mass of sampling tube
$P_{loss}$=power loss The total power may be calculated (reference number 2066) as follows:

Total power=Sampled power*Y sccm/X sccm

Figure 22:
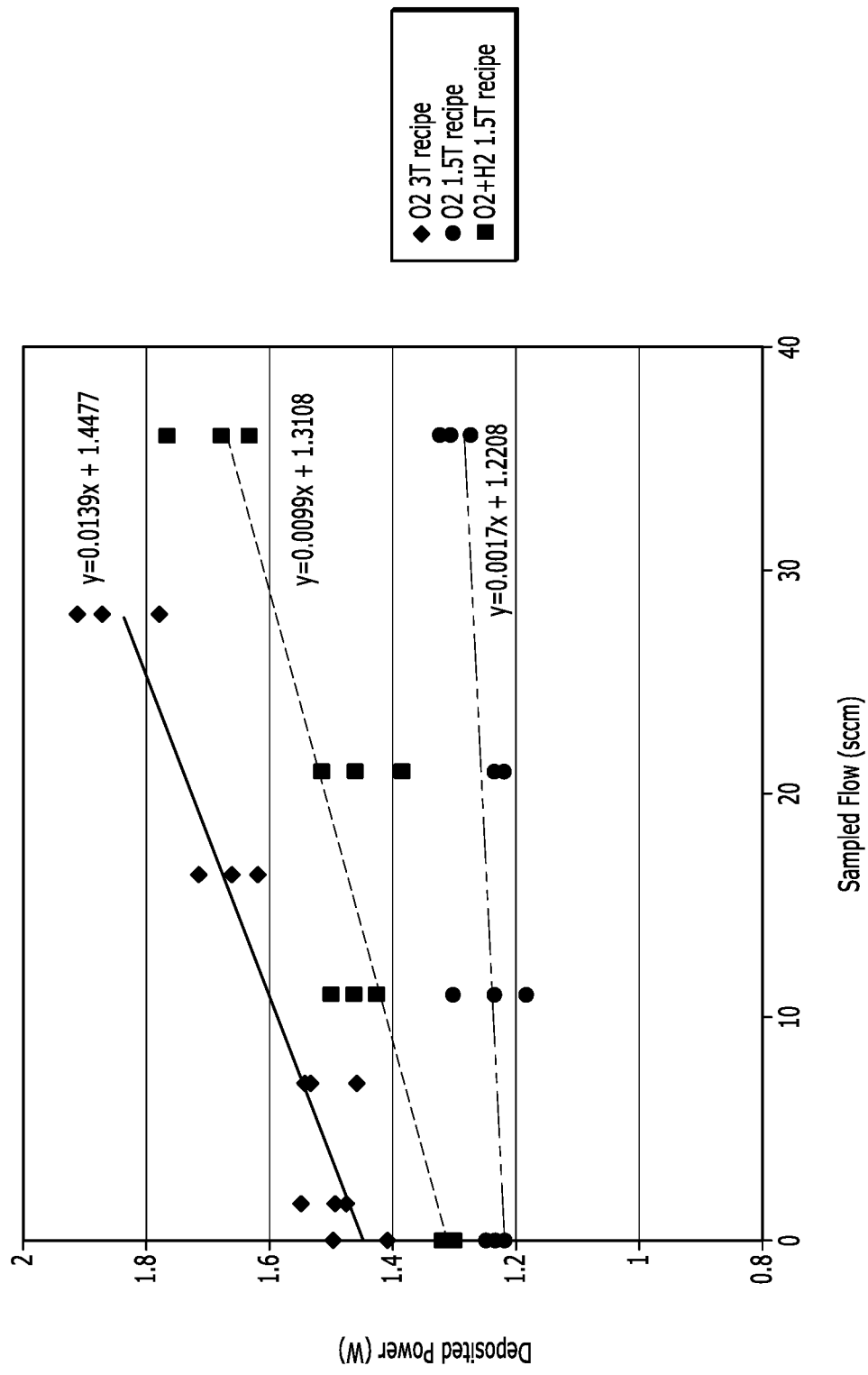
FIG. 22 shows graphically the extrapolated power measurements calculated while calibrating the multi-sensor gas sampling detection system described in FIG. 21.

Thereafter, the flow rate (Y' sccm) or volume of the radical gas stream directed to the sampling reaction module 700 may be selectively adjusted (reference number 2068). For example, at least one valve device 22 (See FIG. 1) may be adjusted to vary the flow of radical gas into the sampling reaction module 700. As shown in FIG. 22, after collecting the sampled power at several different sampling flows, the results can be plotted and used to extrapolate a reading at 0 flow (valve closed). The slope of the extrapolated line is then the sensitivity of the measurement to the sampled flow, which will have a greater dependence on the radicals recombination, and less on the heat from the hot gas.

Figure 23:
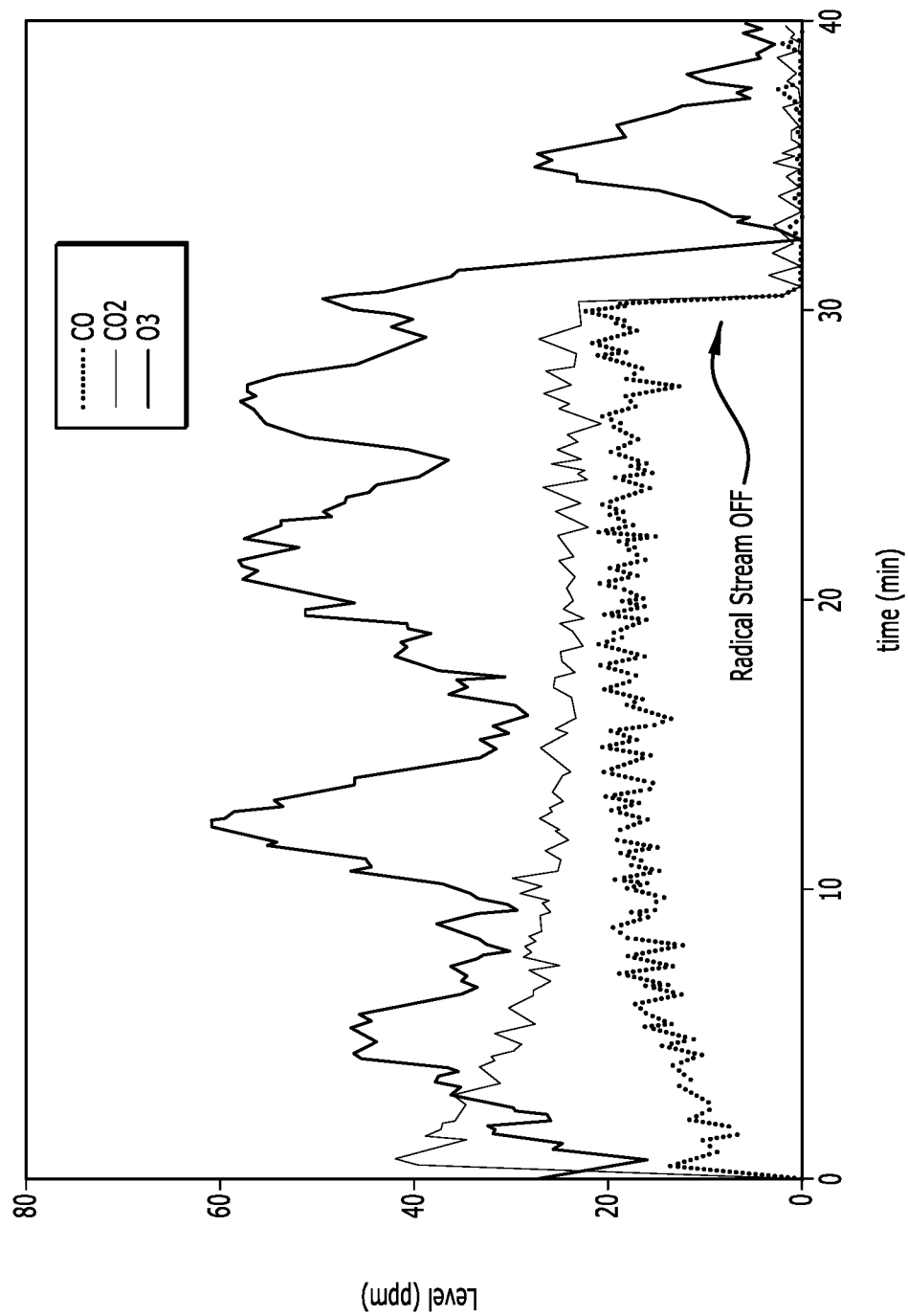
FIG. 23 shows graphically the measured concentration of oxygen radical measured using an optical-based measurement system with the multi-sensor gas sampling detection system described in the present application.

Optionally, multi-sensor gas detection sampling system 700 may include at least one optically reactive material and at least one detector such as an FTIR or TFS thereby using optically-based determination of the sampled power. As such, rather than performing the diagnostics in situ where it is exposed to the radical elements materials, the user may wish to recombine the radical species into a molecular gas species first, then transport the molecular gas species to the optical sensing device, which may now be located farther away. For example, in one specific example, a carbon material may be used within the multi-sensor gas detection sampling system 700. During use, an atomic species such as oxygen react with the carbon and produce $CO$ or $CO_2$. The $CO$ or $CO_2$ gases can then be diverted to a remote optical sensor to detect the amount $CO$ or $CO_2$ present. Thereafter, as shown in FIG. 23, the concentration of $CO$, $CO_2$, can be optically determined, thereby providing the concentration of O-radicals within the gas stream. The reagent material may be chosen such that it only reacts with the atomic species and not with its molecular species. Exemplary reagent materials include:

| Radical to be sensed/reacted | Material for reaction | Gases that cannot be sensed | Species to be detected |
|---|---|---|---|
| H | Carbon (graphite, C-fiber, a-C), Si, $SiO_2$ | $H_2$ | $CH_x$ |
| O | Carbon(graphite, C-fiber, a-C) | $O_2$, $H_2O$ | $CO$, $CO_2$ |
| F, Cl | Silicon, $SiO_2$, SiC | $NF_3$, $F_2$, $Cl_2$ | $SiF_4$ |

Figure 24:
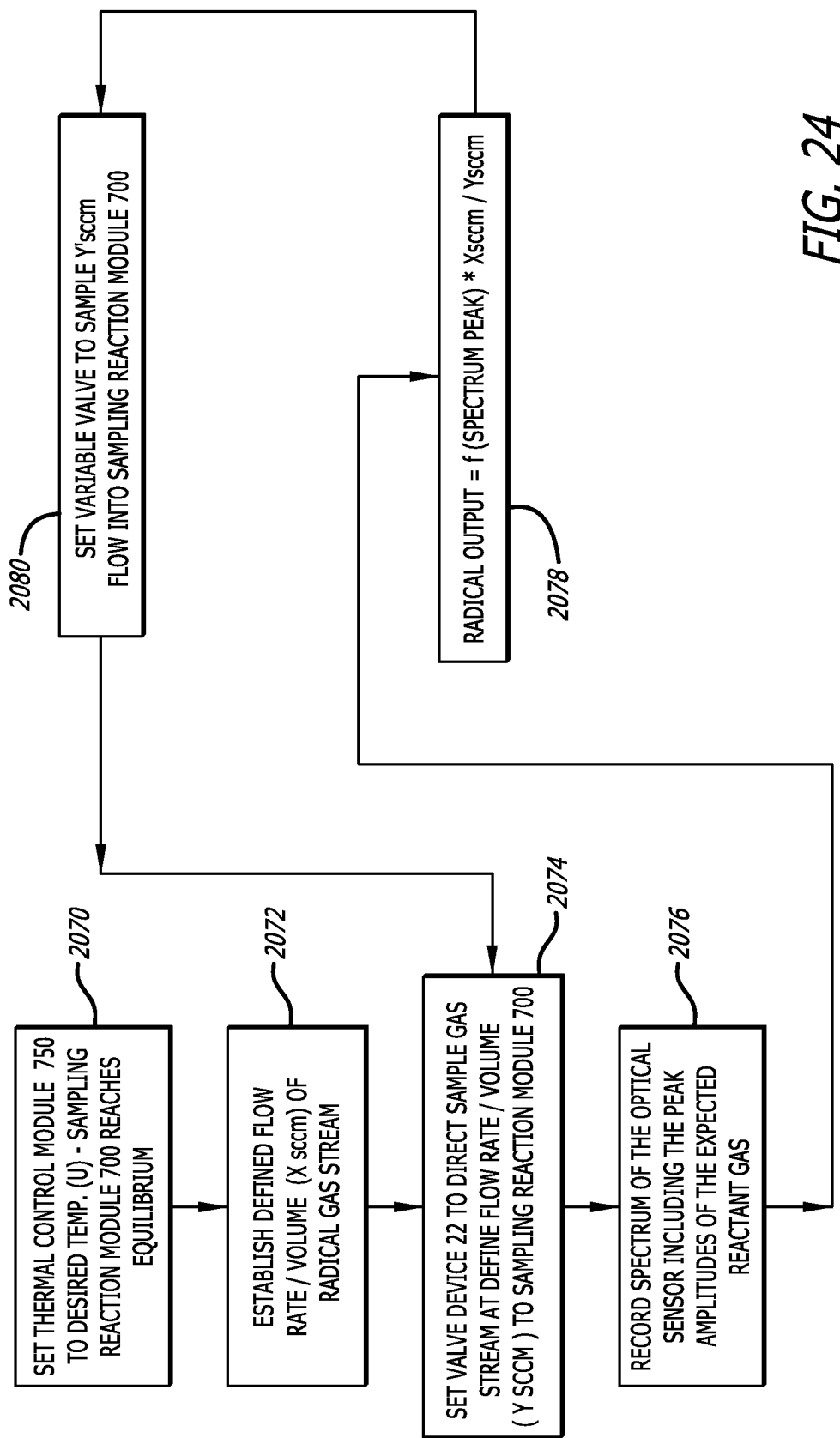
FIG. 24 shows a flow diagram describing an optical-based method of using the multi-sensor gas sampling detection system described in FIGS. 1-7.

FIG. 24 shows a flow chart of an exemplary optically-based measurement process. As shown, the thermal control module 750 of the sampling reaction module 700 is set to a stable desired temperature (U) (reference number 2070). Thereafter, a defined flow rate (X sccm) of a radical gas is established (reference number 2072). Further, a defined flow rate (Y sccm) or volume of the radical gas stream is directed to the sampling reaction module 700 (reference number 2074). A spectrum from the optical sensor or detector (FTIP/TFS) within the thermal control module 750 may be recorded (reference number 2076). Thereafter, the radical output may be calculated (reference number 2078) as follows:

Radical output=f(spectrum peak)*X sccm/Y sccm

The flow rate (Y' sccm) or volume of the radical gas stream directed to the sampling reaction module 700 may be selectively adjusted (reference number 2080). For example, at least one valve device 22 (See FIG. 1) may be adjusted to vary the flow of radical gas into the sampling reaction module 700. As a result, the measured result indicates the relative amplitude of a given radical stream, which can be used for process monitoring. Also, the sampling tube 780 may be set to a fixed temperature to improve the selectivity of the reaction. For example, a temperature may be chosen so that the reacting material will preferentially react with the atomic radical species and not the molecular gas species.

Figure 25:
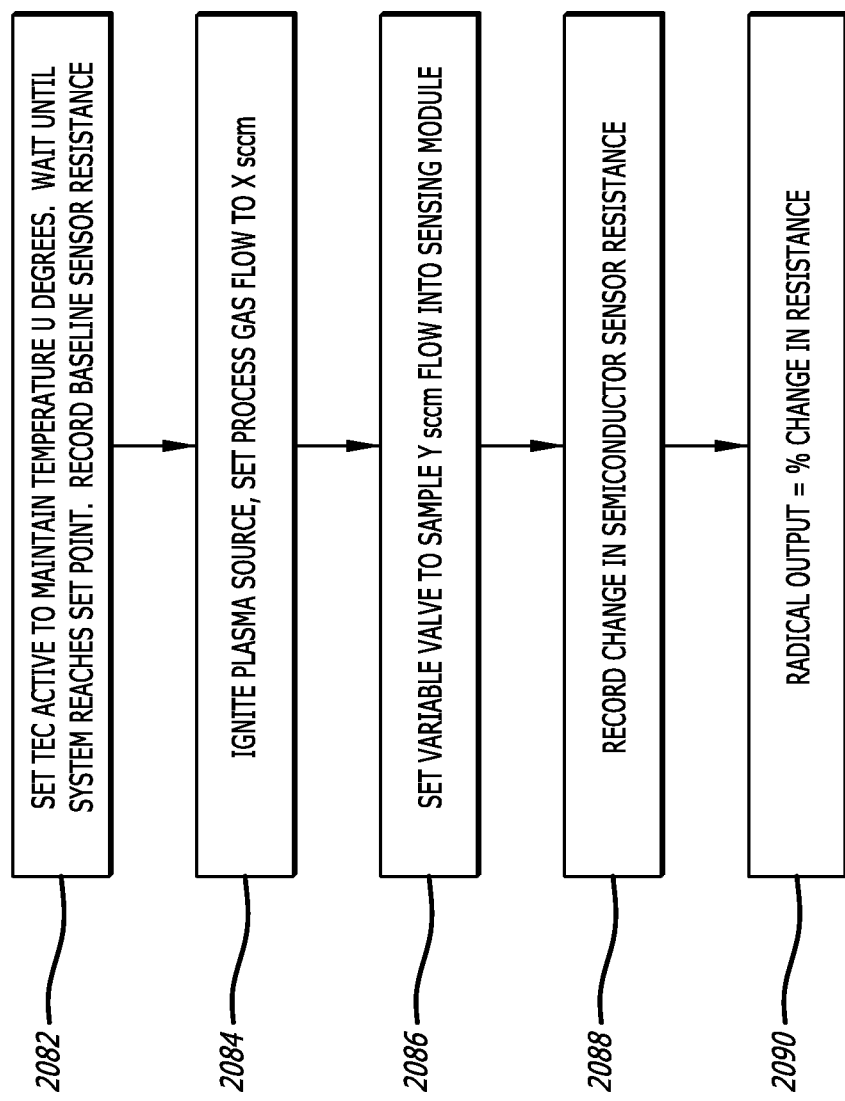
FIG. 25 shows a flow diagram describing a semiconductor-based method of using the multi-sensor gas sampling detection system described in FIGS. 1-7.

In another embodiment, the sampling reaction module 700 may include a semiconductor-based sampling architecture in which at least one semiconductor material is positioned within the sampling reaction module 700. More specifically, as shown in FIG. 25, the thermal control module 750 of the sampling reaction module 700 is set to a stable desired temperature (U) (reference number 2082). Thereafter, a defined flow rate (X sccm) of a radical gas is established (reference number 2084). Further, a defined flow rate (Y sccm) or volume of the radical gas stream is directed to the sampling reaction module 700 (reference number 2086). A resistance from at least one semiconductor sensor positioned within the sampling reaction module 700 may be recorded (reference number 2088). Thereafter, the radical output may be calculated (reference number 2090) as follows:

Radical output=% of change in resistance

Figure 26:
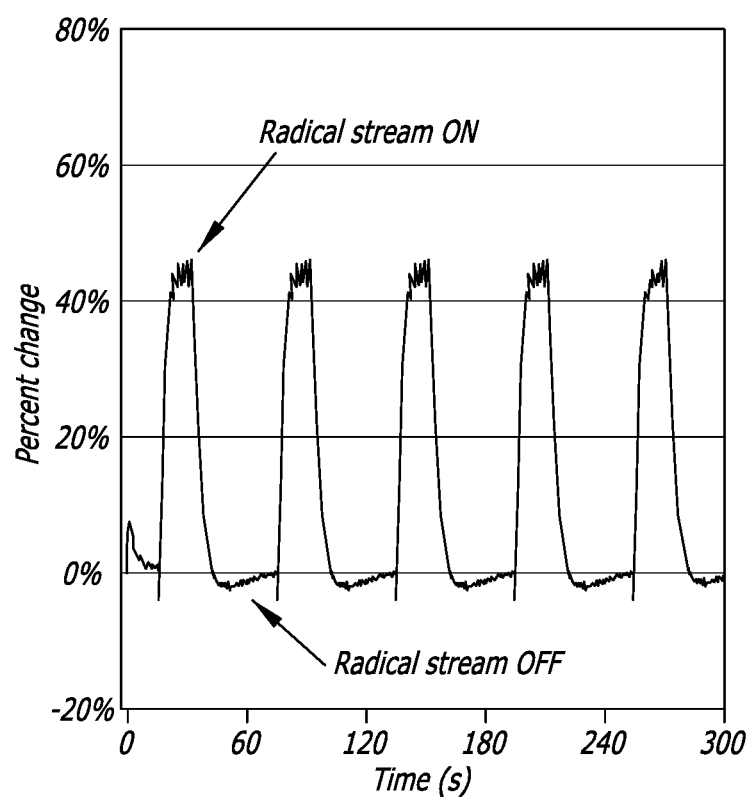
FIG. 26 shows graphically the result of resistance change as the radical output stream is activated and deactivated when using the resistance-based sampling architecture shown in FIG. 25.

FIG. 26 shows graphically the result of resistance change as the radical output stream is activated and deactivated when using the resistance-based sampling architecture described above and shown in FIG. 25.

Figure 27:
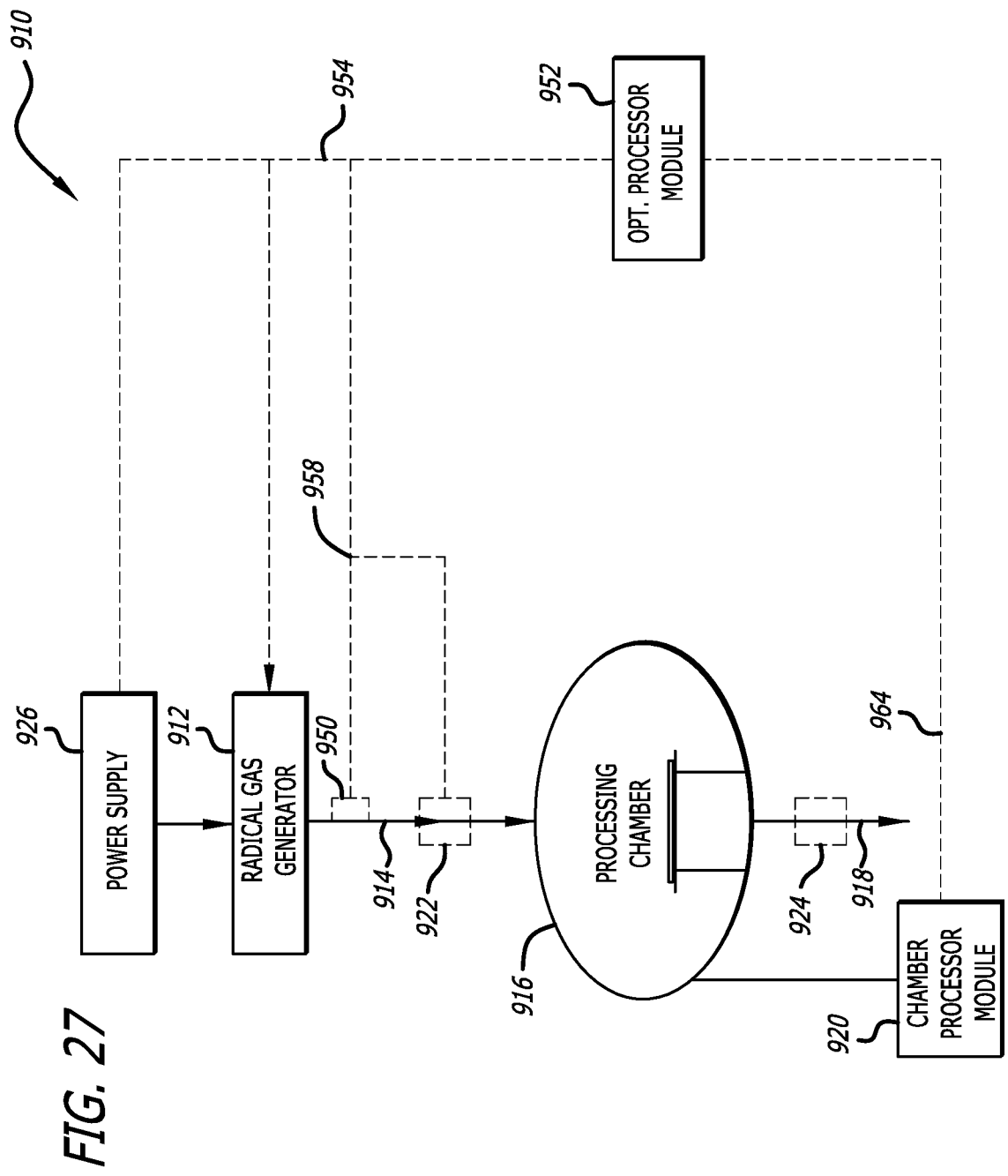
FIG. 27 shows a schematic diagram of another alternate embodiment of a multi-sensor gas sampling detection system.

FIG. 6 described above shows schematically embodiment of a gas sampling detection system useful for detecting the concentration of radicals within a gas stream. In contrast to the system described in FIG. 6, FIG. 27 shows an embodiment of a gas sampling detection system 910 which includes a novel calorimetry architecture positioned downstream of the radical gas generator or remote plasma source. As shown in FIG. 27, the gas sampling detection system 910 includes at least one plasma generator and/or radical gas generator 912 in fluid communication with at least one processing chamber 916 via at least one reactive gas conduit 914. In one embodiment, the radical gas generator 912 is in communication with at least one sample gas source and at least one plasma source configured to energize and dissociate sample gases and generates at least one reactive gas stream. In one specific embodiment the radical gas generator 912 comprises a RF toroidal plasma source; although those skilled in the art will appreciate that any variety of plasma sources or radical gas sources may be used with the present systems. In one embodiment the radical gas generator 912 uses hydrogen ($H_2$) plasma to create atomic hydrogen. In another embodiment the radical gas generator 912 utilizes oxygen ($O_2$) plasma to create atomic oxygen. Optionally, the radical gas generator 912 may utilize nitrogen trifluoride ($NF_3$), fluorine ($F_2$), chlorine ($Cl_2$), ammonia ($NH_3$) or any variety of other materials to create a reactive plasma containing one or more radicals within the gas stream. Alternatively, radical gases may be generated by other gas excitation methods, including electron beam excitation, laser excitation, or hot-filament excitation. Further, the above description discloses various embodiments of RF-based plasma generation systems; although those skilled in the art will appreciate that any variety of alternate radical gas generation systems may be used with the present system. Exemplary alternate radical gas generation systems include, without limitation, glow discharge plasma systems, capacitively coupled plasma systems, cascade arc plasma systems, inductively coupled plasma systems, wave heated plasma systems, arc discharge plasma systems, coronal discharge plasma systems, dielectric barrier discharge systems, capacitive discharge systems, Piezoelectric direct discharge plasma systems, and the like.

Referring again to FIG. 27, at least one processing chamber 916 may be in fluid communication with the radical gas generator 912 via at least one reactive gas conduit 914. In some applications, the reactive gas conduit 914 is manufactured from a chemically inert material or a material having low chemical reactivity. Exemplary materials include, without limitation, quartz, sapphire, stainless steel, strengthened steel, aluminum, ceramic materials, glass, brass, nickel, $Y_2O_3$, $YAlO_x$, various alloys, and coated metal such as anodized aluminum. In one embodiment a single reactive gas conduit 914 is in fluid communication with a single radical gas generator 912. In another embodiment multiple reactive gas conduits 914 are in fluid communication with a single radical gas generator 912. In yet another embodiment, a single reactive gas conduit 914 is in communication with multiple radical gas generators 912. Optionally, the reactive gas conduit 914 may comprise a sampling conduit or tube performing a similar function to the sampling tube 780 described above and shown in FIGS. 11-13. As such, any number of reactive gas conduits 914 may be in communication with any number of radical gas generators 912. Further, at least one valve device or sensor device 922 may be included on the reactive gas conduit 914 between the radical gas generator 912 and the processing chamber 916. For example, in one embodiment the valve device 922 may be configured to selectively permit or restrict the flow of at least one fluid through the reactive gas conduit 914 to create a desired pressure differential between the radical gas generator 912 and the processing chamber 916. In one embodiment, the valve device 922 may comprise a variable valve or, in the alternative, a fixed-sized orifice. In one embodiment, the valve device 922 may be positioned downstream of sensor device 950, as shown in FIG. 27. Alternatively, the valve device 922 may be positioned upstream of sensor device 950.

As shown in FIG. 27, the processing chamber 916 may be coupled to or in communication with the radical gas generator 912 via the reactive gas conduit 914. In one embodiment, the processing chamber 916 comprises one or more vacuum chambers or vessels configured to have one or more substrates, semiconductor wafers, or similar materials positioned therein. For example, the processing chamber 916 may be used for atomic layer processing of semiconductor substrates or wafers. Optionally, the processing chamber 916 may be used for processing any variety of substrates or materials using any variety of processing methods or systems. Exemplary processing methods include, without limitation, physical vapor deposition (PVD), chemical vapor deposition (CVD), rapid thermal chemical vapor deposition (RTCVD), atomic layer deposition (ALD), atomic layer etching (ALE), and the like. Those skilled in the art will appreciate that the processing chamber 916 be manufactured from any variety of materials, including, without limitation, stainless steel, aluminum, mild steel, brass, high-density ceramics, glass, acrylic, and the like. For example, at least one interior surface of the processing chamber 916 may include at least one coating, anodized material, sacrificial material, physical feature or element, and the like intended to selectively vary the reactivity, durability, and/or fill micro-pores of the interior surfaces of the processing chamber 916. At least one exhaust conduit 918 may be coupled to the processing chamber 916 and configured to evacuate one or more gases or materials from the processing chamber 916. Optionally, one or more control sensors, valves, scrubbers, or similar devices 924 may be coupled to or positioned proximate to the exhaust conduit 918, thereby permitting the user to selectively evacuate one or more gases or other materials from the processing chamber 916.

Referring again to FIG. 27, at least one chamber processor module 920 may be coupled to or otherwise in communication with the processing chamber 916 and/or various components of the processing system. The chamber processing module 920 may be configured to provide localized control of the various components forming the processing system 910. In the illustrated embodiment the chamber processing module 920 is in communication with the processing chamber 916 via at least one conduit, although those skilled in your will appreciate that the chamber processing module 920 may communicate with any of the components forming the processing system 910 via conduit, wirelessly, or both.

As shown in FIG. 27, the reactive gas conduit 914 may include one or more sensor systems and/or similar devices 950 coupled thereto or in communication there with. For example, in the illustrated embodiment, at least one calorimetry sensor device 950 may be positioned within and/or coupled to the reactive gas conduit 914, although those skilled in the art will appreciate any variety of sensor devices or systems may be used in the present system. Unlike the embodiments shown in FIG. 6 and described above, the embodiment of the gas sampling detection system 910 shown in FIG. 27 need not include the embodiment of the sample reaction module 700 included in gas sampling detection system 510 shown in FIG. 6.

As shown in FIG. 27, the processing system 910 may include at least one optional processor module 952 in communication with at least one component of the processing system 910. For example, in the illustrated embodiment, an optional processor module 952 is in communication with the radical gas generator 912 and power supply 926 via at least one processor conduit 954. Further, the optional processor system 952 may be in communication with the sensor 950 via the processor conduit 954 and the sensor conduit 958. In one embodiment, the optional processor module 952 may be configured to provide and receive data from at least one of the radical gas generator 912, the power supply 926 and the sensor device 950. As such, the optional processor module 952 may be configured to measure the flow conditions within the processing system 910 via the sensor device 950 and selectively vary the operating conditions of the processing system 910 or the power supply 926 to optimize system performance. More specifically, the optional processor module 952 may be configured to measure the concentration of radicals and/or short-lived molecules within the radical gas stream and vary the operating characteristics of the radical gas generator 912 to increase or decrease the concentration of radicals within the radical gas stream. As stated above, the sensor device 950 may comprise a calorimetry sensor device 950. Further, the optional processor module 952 may be in communication with and provide/receive data from at least one of the optional valve device 922 (via conduit 958) and chamber processor module 920 (via conduit 964). The optional processor module 952 may also be configured to provide and receive plasma power or input power to the power supply 926. Optionally, the processor 952 may be in communication with the various components of the processing system 910 wirelessly. Further, the processor 952 may be configured to store performance data, processing formulas and times, lot number, and the like. In addition, the processor 952 may be configured to communicate with one or more external processors via at least one computer network.

Figure 29:
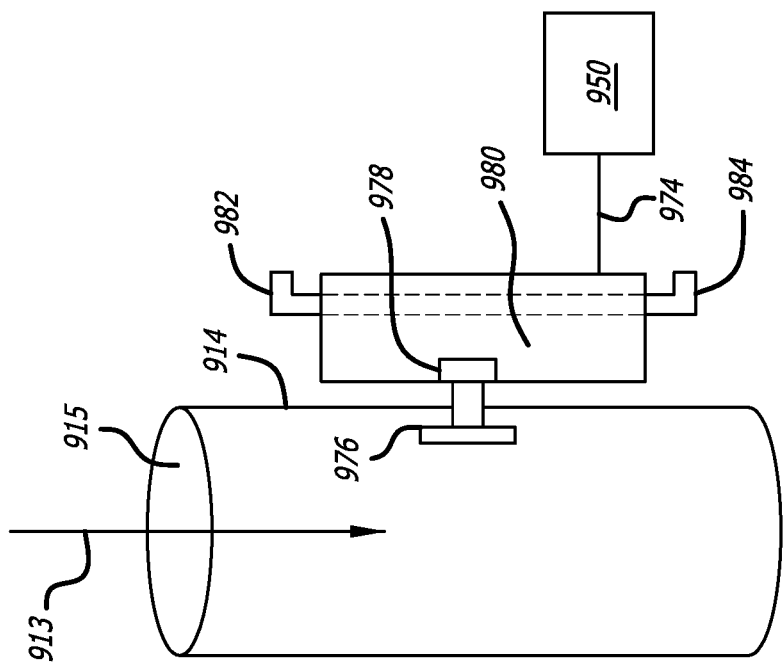
FIG. 29 shows an elevated perspective view of another embodiment of a reactive gas conduit having at least one sensor body positioned within the reactive gas conduit for use in the embodiment of the gas sampling detection system shown in FIG. 27.
Figure 28:
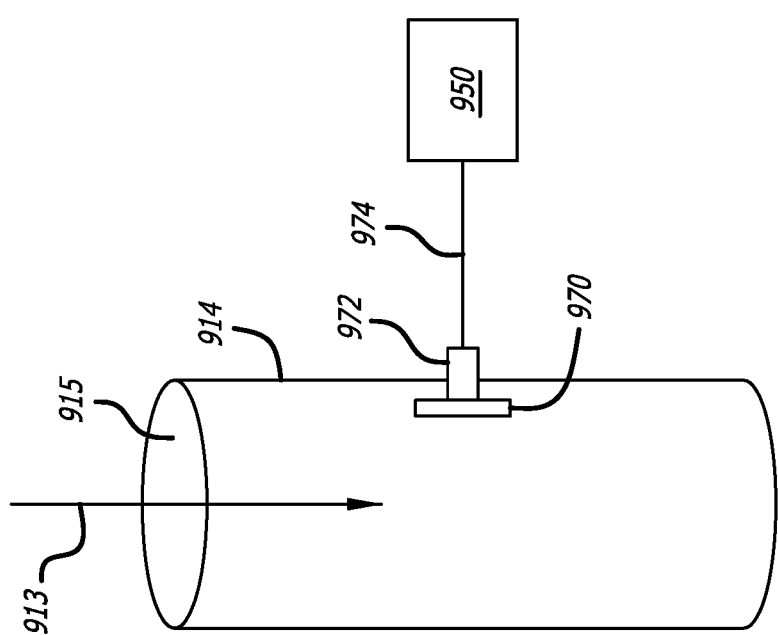
FIG. 28 shows an elevated perspective view of an embodiment of a reactive gas conduit having at least one sensor body positioned within the reactive gas conduit for use in the embodiment of the gas sampling detection system shown in FIG. 27.

FIGS. 28 and 29 show various embodiments of a sensor architecture or device which may be used to form the sensor device 950. As shown in FIG. 28, in one embodiment the sensor device 950 may be coupled to or otherwise in communication with the reactive gas conduit 914 via at least one conduit 974. Further, at least one sensor body 970 may be positioned within at least one gas passage 915 formed within the reactive gas conduit 914 and in communication with the sensor device 950 via the conduit 974. In the illustrated embodiment, a single sensor body 970 is positioned within the reactive gas conduit 914, although those skilled in art will appreciate any number of sensor bodies may be positioned within the reactive gas conduit 914 and coupled to the sensor device 950. Further, in one embodiment the sensor body 970 is thermally isolated from the reactive gas conduit 914 using at least one isolation device 972. In the alternative, those skilled in the art will appreciate that the sensor body 970 need not be thermally isolated from the reactive gas conduit 914. The sensor body 970 may be manufactured from any variety of materials, including, without limitations, carbon, graphite, silica, carbon fiber, silicon dioxide, silica and carbide, carbon-based materials, silica-based materials, and the like. As such, at least a portion of the sensor body 970 may be configured to react with radicals contained within the radical gas stream flowing through the reactive gas conduit 914, thereby forming chemical species such as carbon monoxide (CO), carbon dioxide ($CO_2$), carbon-hydrogen molecules (methylidyne radical), methylene ($CH_2$), methyl-group compounds ($CH_3$), methane ($CH_4$), silicon tetrafluoride, and similar compounds which may be more easily detected. Optionally, the sensor body 970 may be manufactured from any variety of chemically inert materials such as stainless steel, ceramics, nickel, tungsten, aluminum, various alloys, and the like. Optionally, the sensor body 970 may also be manufactured from a catalytic material such as platinum, palladium, nickel that may react with one or more elements or chemical compounds in the radical gas stream, providing chemical composition and/or concentration of specific gases in the radical gas.

During use, a reactive gas 913 generated by the plasma generator is directed through the reactive gas conduit 914. The sensor body 970 positioned within the gas passage 915 formed in the reactive gas conduit 914 is located within the stream of radical gas 913. The temperature of the thermally isolated sensor body 970 is measured by the sensor device 950. Thereafter, sensor device 950 provides the calorimetric data measured by the sensor body 970 to at least one of the optional processor module 952 and/or the plasma generator 912. As such, the operational parameters of the radical gas generator 912 may be adjusted based on the calorimetric measurements performed by the sensor device 950.

FIG. 29 shows another embodiment of a reactive gas conduit 914 having a sensor device 950 in communication therewith. More specifically, the sensor device 950 includes a first sensor body 976 and a second sensor body 978 positioned on or otherwise coupled to at least one thermal body 980. As shown in the illustrated embodiment, the first sensor body 976 may be positioned within at least one gas passage 915 formed in the reactive gas conduit 914 (and within the radical gas stream 913) while the second sensor body 978 is located distally from the reactive gas conduit 914. In an alternate embodiment, the first sensor body 976 and second sensor body 978 are both positioned within the proximate to the reactive gas conduit 914. Further, the thermal body 980 may include at least one fluid inlet 982 and at least one fluid outlet 984. In one embodiment, the thermal body 980 may be configured to maintain at least a portion of the reactive gas conduit 914 at a desired temperature. Like the previous embodiment, at least one of the first sensor body 976 and/or the second sensor body 978 is in communication with the sensor device 950 via at least one conduit 978. During use, the temperature of the first sensor body 976 positioned within the gas passage 915 formed within the radical gas stream is measured by the sensor device 950 when a reactive gas 913 flows through the reactive gas conduit 914. In addition, the temperature of the second sensor body 978 is similarly measured by the sensor device 950. Thereafter, the temperature gradient between the first sensor body 976 and second sensor body 978 may be calculated by at least one of the sensor device 950 and the optional processor module 952. Thereafter, the performance characteristics of the radical gas generator 912 may be adjusted to optimize performance. Optionally, the temperature of the fluid flowing into the thermal body 980 via the fluid inlet 982 may be compared to the temperature of the fluid flowing out of the thermal body 980 via the fluid outlet 984 and fluid outlet 984, thereby permitting a user to calculate heat transfer within the thermal body 980. In one embodiment, the reactive gas conduit 914 may be configured to permit radicals within the gas stream flowing within the reactive gas conduit 914 to recombine. As such, those skilled in the art will appreciate that the recombination power of the gas stream (output calorimetry) may be calculated by at least one of the sensor body 950 in the optional processor module 952.

Figure 30:
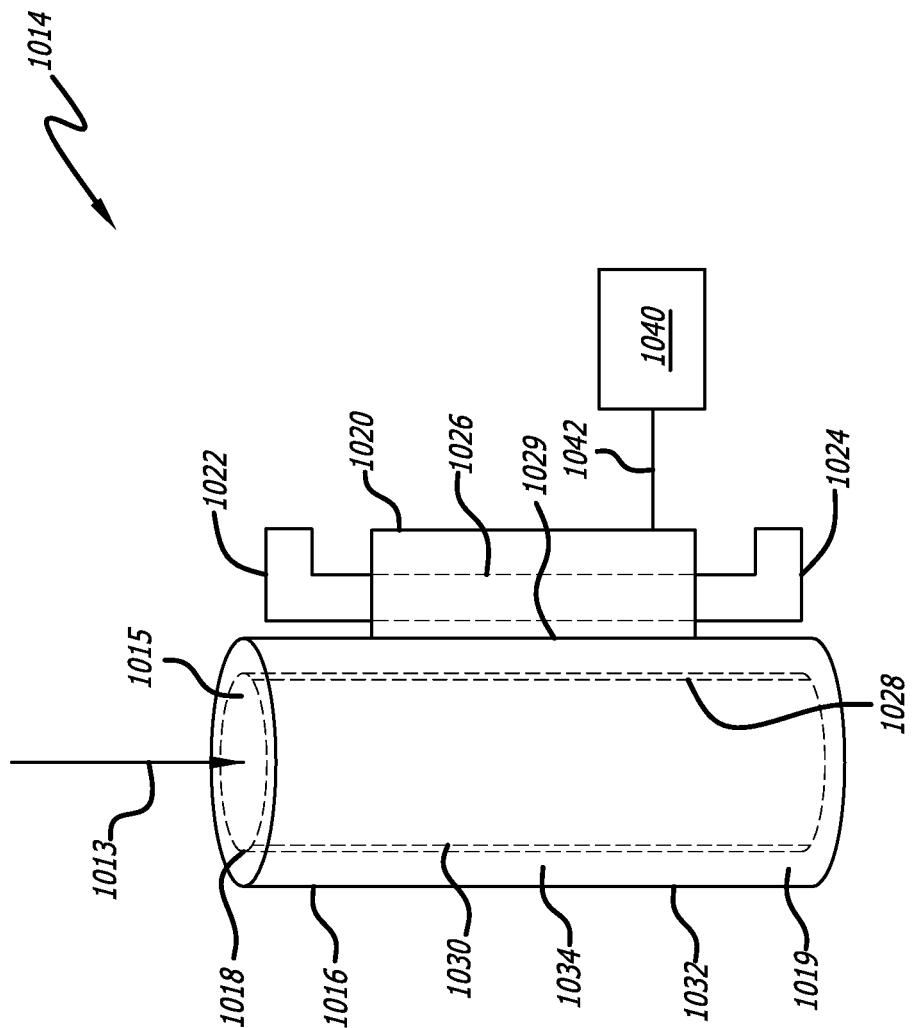
FIG. 30 shows an elevated perspective view of another embodiment of a reactive gas conduit having at least one sensor body positioned within the reactive gas conduit for use in the embodiment of the gas sampling detection system shown in FIG. 27.

FIG. 30 shows an alternate embodiment of a radical gas conduit 1014 in which at least one surface of the reactive gas conduit 1014 forms a thermal sensor device. More specifically, the reactive gas conduit 1014 includes a conduit body 1016 having at least one inner surface 1018 and at least one outer surface 1019. As such, the inner surface 1016 of the reactive gas conduit 1014 defines at least one gas passage 1015. Further, at least one thermal body 1020 may be coupled to or otherwise in communication with at least a portion of the reactive gas conduit 1014. As shown, the thermal body 1020 may include at least one inlet 1022 and at least one outlet 1024. The inlet 1022 and outlet 1024 may be in communication with at least one conduit 1026 traversing through or positioned proximate to the thermal body 1020. In one embodiment, at least one fluid may be flowed through the thermal body 1020 via the inlet 1022, outlet 1024, and conduit 1026. In the illustrated embodiment, a thermal body 1020 is positioned proximate to a section of the reactive gas conduit 1014. Optionally, the thermal body 1020 may be positioned along the entire length of the reactive gas conduit 1014.

Referring again to FIG. 30, at least one sensor device 1028 may be positioned within the conduit body 1016 of the reactive gas conduit 1014. For example, in the illustrated embodiment, the sensor device 1028 is positioned on or proximate to the inner surface 1015 of the conduit body 1016. In one embodiment, the sensor device 1028 includes at least one sensor therein. In the illustrated embodiment, the sensor device 1028 includes a first sensor region 1030 and at least a second sensor region or device 1032. In the illustrated embodiment, the first sensor 1030 may be located within or proximate to the inner surface 1018 of the conduit body 1016. Optionally, the entire inner surface 1018 may be configured to form the first sensor region 1030. As such, the first sensor region 1030 may be configured to measure recombination temperature/energy of the radical flow within the reactive gas conduit 1014. The second sensor region 1032 may be positioned external of the conduit body 1016. For example, in one embodiment the second sensor region 1032 may be positioned proximate to the outer surface 1019 of the conduit body 1016. In one embodiment, the second sensor region 1032 is configured to measure temperature external of the conduit body 1016. During use, the user may calculate a temperature gradient between the first sensor region 1030 positioned on or proximate to the inner surface 1018 within the conduit body 1016 and the second sensor region 1032 positioned proximate to the outer surface 1019 external of the conduit body 1016. Optionally, additional sensor regions 1029 may be positioned on the gas conduit 1014. For example, in the illustrated embodiment an additional sensor 1029 is positioned proximate to the thermal body 1020. The first and second sensor regions 1030, 1032 may be separated by at least one thermal region 1034 which is in communication with the thermal body 1020. Optionally, the thermal region 1034 may include one or more conduits (not shown) configured to have one or more fluids flowed there through. As such, the thermal region 1034 may be in communication with the inlet 1022 and outlet 1024 formed on the thermal body 1020. In another embodiment, the inner surface 1018 of the conduit body 1016 may be configured to act as a sensor. Like the previous embodiment, the sensor device 1028 may be in communication with at least one sensor controller 1040 via at least one sensor conduit 1042.

During use, the temperature of the recombination heat of the reactive gas flow flowing through the reactive gas conduit 1014 is measured by the sensor device 1028 for sensor region 1030, and the additional sensor region 1029 for sensor region 1032, which are both in communication with the sensor device 1040. Thereafter, the performance characteristics of the radical gas generator 912 may be adjusted to optimize performance (See FIG. 27). Optionally, the temperature of the fluid flowing into the thermal body 1020 via the fluid inlet 1022 may be compared to the temperature of the fluid flowing out of the thermal body 1020 via the fluid outlet 1024, thereby permitting a user to calculate heat transfer within the thermal body 1020. In one embodiment, the reactive gas conduit 1014 may be configured to permit radicals within the gas stream flowing within the reactive gas conduit 1014 to recombine. As such, those skilled in the art will appreciate that the recombination power of the gas stream (total output calorimetry) may be calculated by at least one of the sensor body 1040 in the optional processor module 952 (See FIG. 27).

Figure 31:
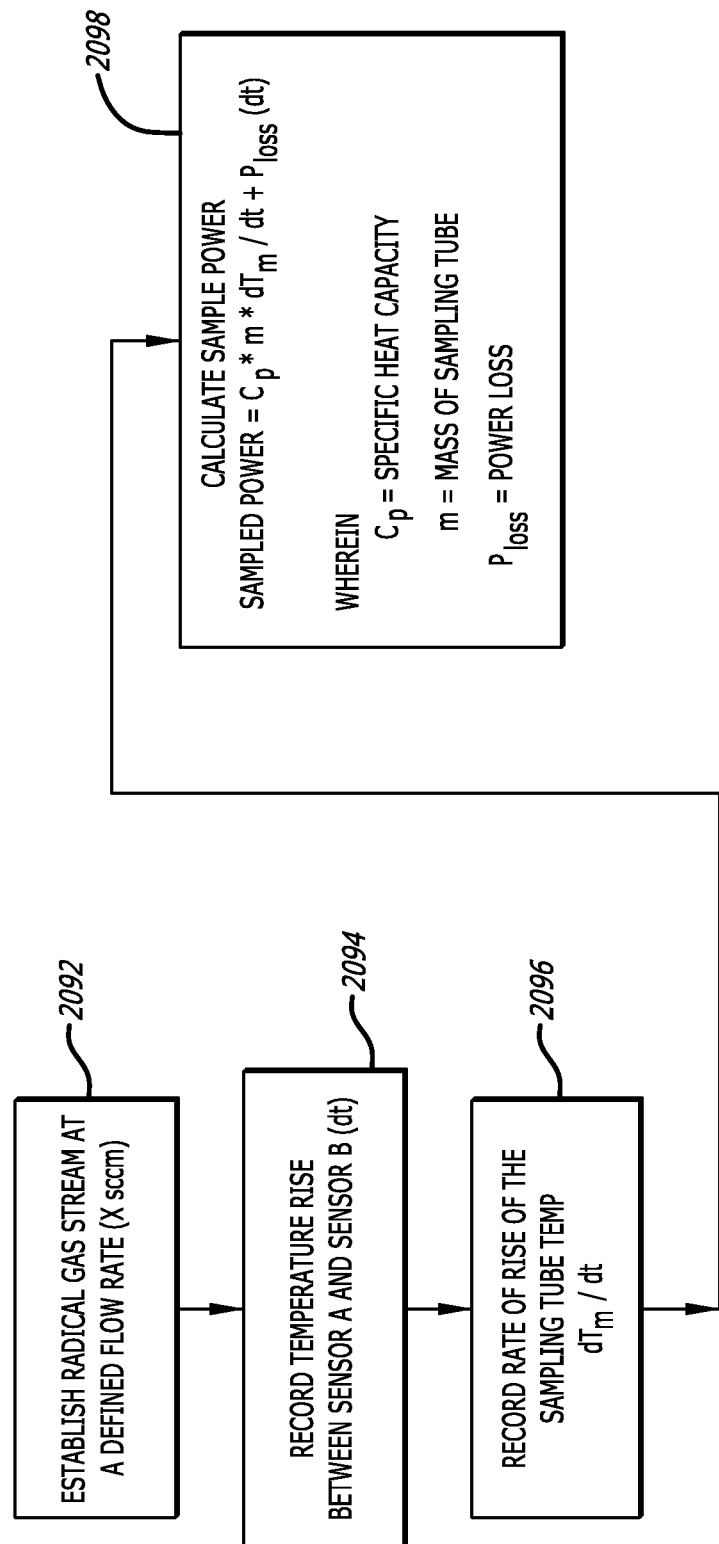
FIG. 31 shows a flow diagram describing a method of using the multi-sensor gas sampling detection system described in FIGS. 27, 29, and 30.

FIG. 31 shows a flow chart of another method of utilizing the sampling reaction module 910 shown in FIGS. 27, 29 and 30. In this embodiment, a flow radical gas stream is established within the multi-sensor gas sampling detection system 910 as a defined flow rate (X sccm) (reference number 2092). Thereafter, the change in temperatures of the first sensor body 982 and second sensor body 984 is recorded (reference number 2094). Further, the rate of the temperature change ($dT_m/dt$) of the reactive gas conduit 914 is also recorded (reference number 2096). Thereafter, the sample power may be calculated (reference number 2098) as follows:

$$\text{Sampled power} = C_p * m_{rgc} * dT_m/dt + P_{loss}(dT)$$

Figure 32:
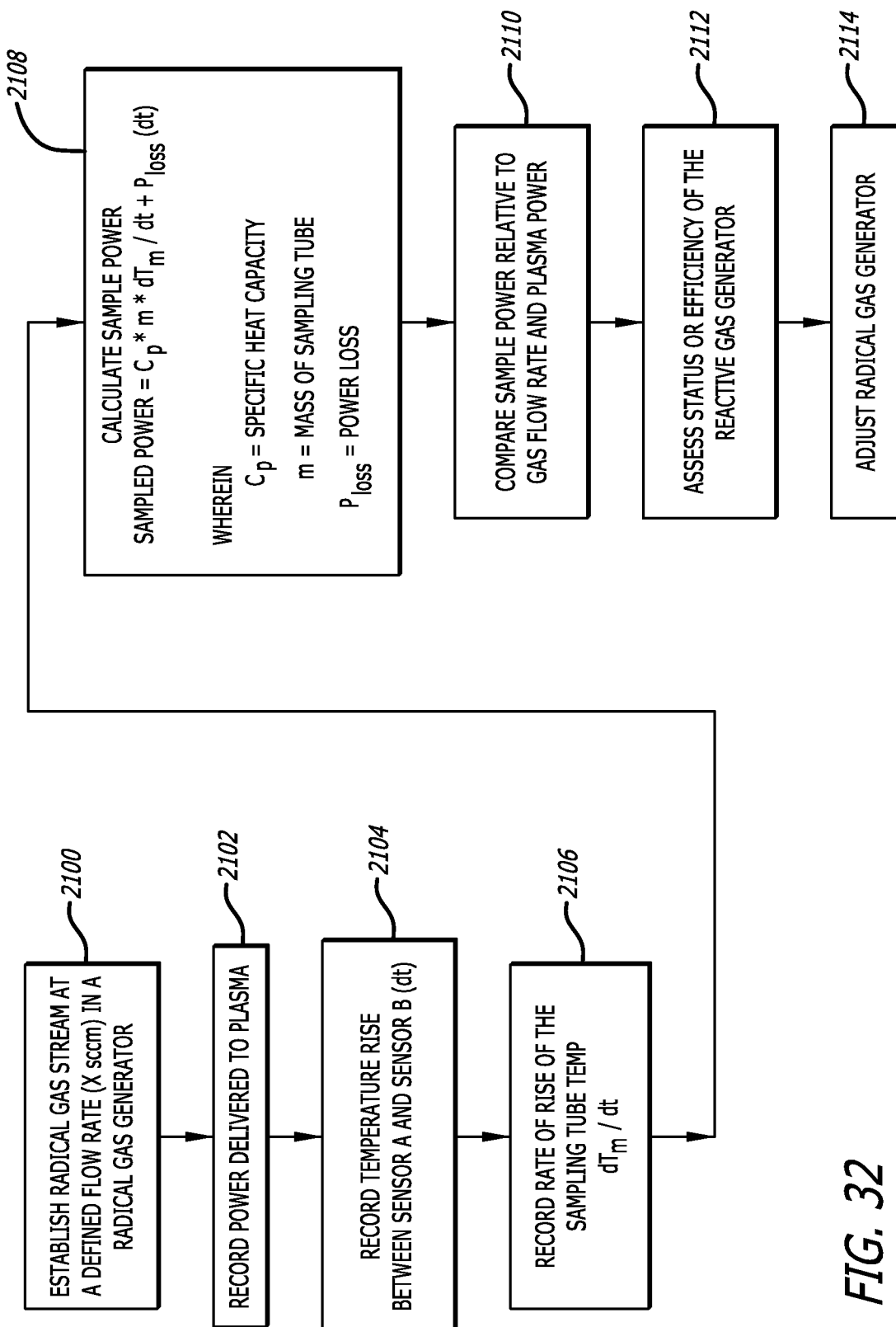
FIG. 32 shows a flow diagram describing another method of using the multi-sensor gas sampling detection system described in FIGS. 27, 29, and 30.

Wherein: $C_p$=specific heat capacity
$m_{eff}$=effective mass of sampling tube
$P_{loss}$=power loss FIG. 32 shows another flow chart of an alternate method of utilizing the sampling reaction module 910 shown in FIGS. 27, 29 and 30. In this embodiment, a flow radical gas stream is established within the multi-sensor gas sampling detection system 910 as a defined flow rate (X sccm) (reference number 2100). Thereafter, the power delivered to the reactive gas flow may be recorded 2102. In addition, the temperature rise (dT) and rate of temperature rise ($dT_m/dT$) may be measured between at least two sensors positioned or proximate to the reactive gas conduit 914 (See FIGS. 27, 29, and 30, FIG. 31 reference number 2104). Optionally, the temperature rise (dT) and rate of temperature rise ($dT_m/dT$) may be measured (reference number 2106) between at least two sensors locations formed in the sensor device 1028 shown in FIG. 31. Thereafter, the sample power may be calculated (reference number 2108) as follows:

$$\text{Sampled power} = C_p * m * dT_m/dt + P_{loss}(dT)$$

Wherein: $C_p$=specific heat capacity
m=mass of sampling tube
$P_{loss}$=power loss Thereafter, the sample power may be compared (reference number 2110) to the gas flow rate and power of the reactive gas, thereby allowing the efficiency of the reactive gas generator to be accurately calculated. Further, the output of the radical gas generator 912 may be assessed (reference number 2112) and selectively adjusted (reference number 2114) by the optional processor module 952, the power supply 926, or both.

Figure 33:
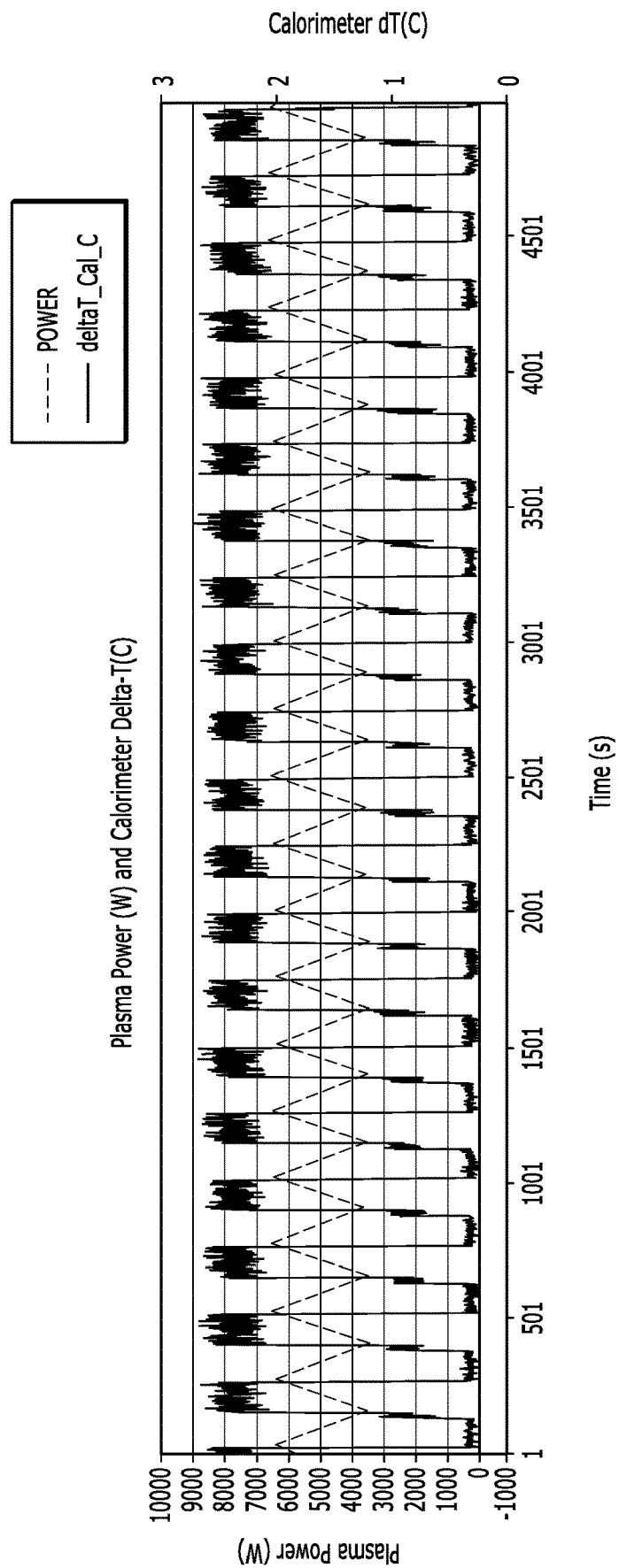
FIG. 33 shows graphically the temperature delta of sensors bodies positioned within the reactive gas conduit of the multi-sensor gas sampling detection system described in FIGS. 27-30.

FIG. 33 shows graphically the temperature change (dT) of the fluid to a reactive gas conduit 914 downstream of the radical gas generators 912 when the radical gas generators 912 is repeatedly cycled between on and off. As shown, when the radical gas generator 912 is initially activated the temperature of the fluid rises and subsequently drops to a lower value during the off cycle. As shown in FIG. 33, with the temperature change (dT) far from reaching steady state during each cycle, the slope of the temperature rise is proportional to the power absorbed by the reactive gas conduit 914 from the radical gas stream generated by the radical gas generators 912.

Figure 34A:
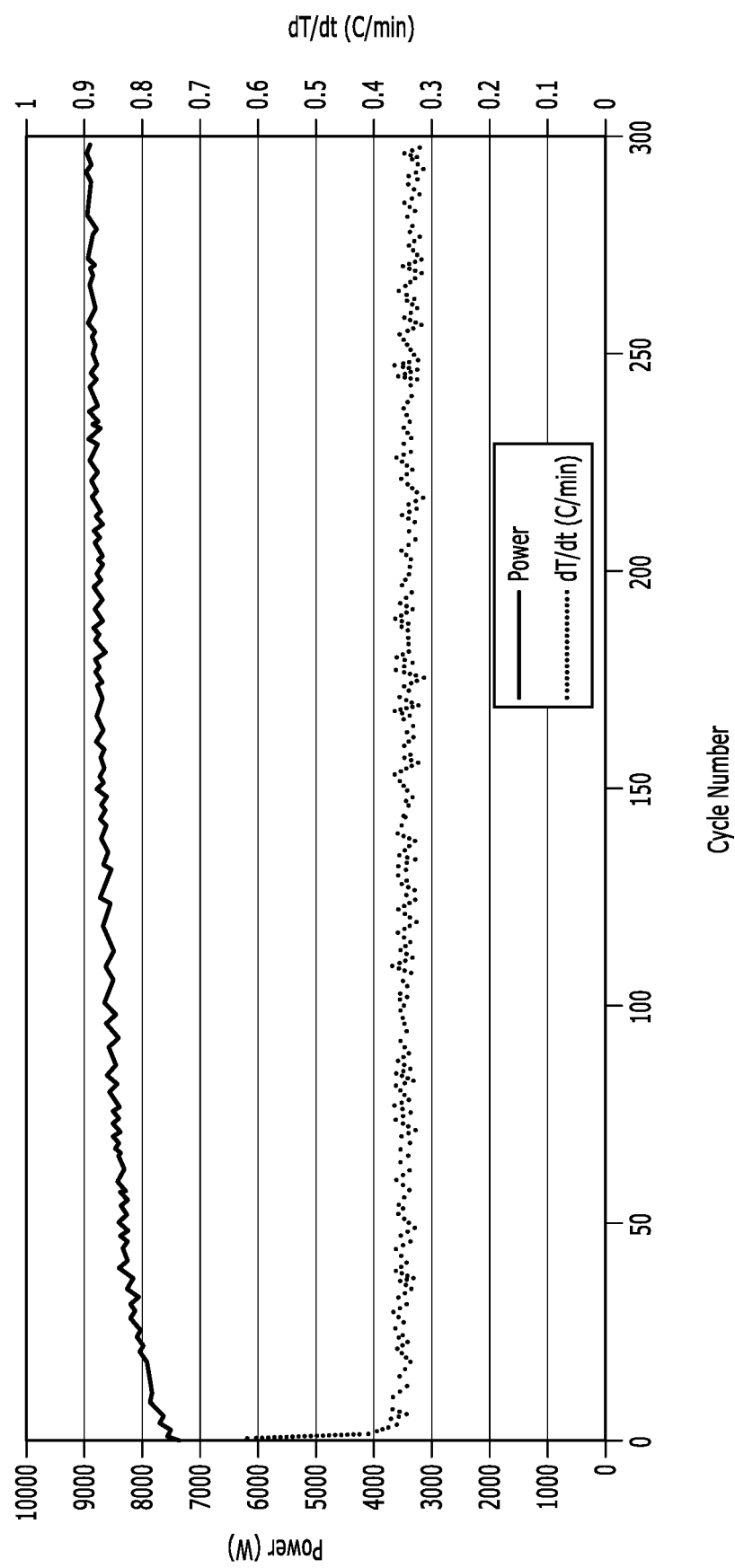
FIG. 34A shows graphically the performance of a first radical gas generator used in the embodiment of the sensor gas sampling detection system described in FIGS. 27 and 30.
Figure 34B:
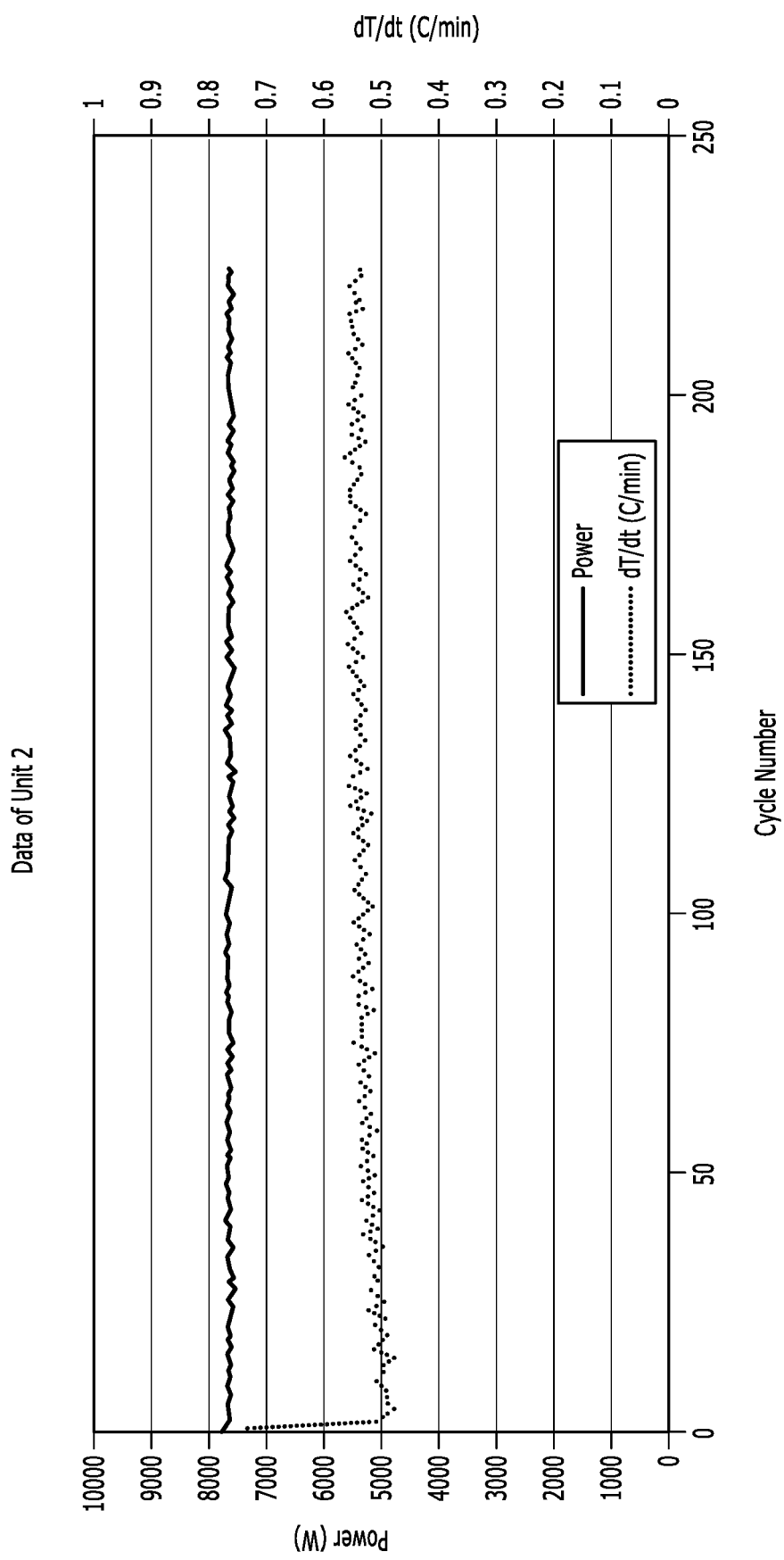
FIG. 34B shows graphically the performance of a second radical gas generator used in the embodiment of the sensor gas sampling detection system described in FIGS. 27 and 30.

FIGS. 34A and 34B shows graphically that two different radical gas generators may have different radical outputs. More specifically, the data of radical gas generator unit #1 shown in FIG. 34A has lower slope in temperature rise (dT/dt) compared to the radical generator unit #2 shown in FIG. 34B. On the other hand, the power input to radical generator unit #1 is higher than the power to radical gas generator #2.

As shown in FIG. 34A, the input power to radical gas generator unit #1 increases from about 7.5 kW to about 10 kW during 300 operation cycles. During the same time, power in the radical gas output decreases. There is a rapid drop during the initial few cycles when the surface of the radical gas generator is changed by plasma-surface interactions in the process chemistry. Subsequently, there is a slow drop of power in the radical gas output stream while the input plasma power increases. This behavior is quite different from that of radical gas generator unit #2 shown in FIG. 34B. Not only the power in the output radical gas steam is higher by as much as 30-40%, the input power to radical gas generator #2 is lower during the entire test. It shows that the radical gas generator unit #2 is more efficient than unit #1. The higher input power and lower power in the output radical gas stream show that there is higher loss of radical gases in radical gas generator #1, which relates to difference in surface compositions of the two radical gas generators.

Therefore, the method of FIG. 32 can not only be used to control or adjust the operation of a radical gas generator, but may also be used to determine and characterize the performance status of a radical gas generator. The ability of separating a bad or deteriorated radical gas generator from the normal ones is particularly useful in an industrial manufacturing environment to ensure consistency of the products.

The embodiments disclosed herein are illustrative of the principles of the invention. Other modifications may be employed which are within the scope of the invention. Accordingly, the devices disclosed in the present application are not limited to that precisely as shown and described herein.

What is claimed is:

1. A system for measuring the concentration of radicals in a gas stream, comprising:
   at least one radical gas generator in communication with at least one gas source, the radical gas generator configured to generate at least one radical gas stream;
   at least one processing chamber in fluid communication with the at least one radical gas generator, the at least one processing chamber configured to receive a portion of the at least one radical gas stream;
   at least one sampling reaction module in fluid communication with the at least one radical gas generator, the sampling reaction module having at least one thermal control module in thermal communication with at least one sampling tube, the at least one sampling tube configured to receive a portion of the radical gas stream from the at least one radical gas generator therein and react at least one reagent with at least one radical gas within a defined volume of the at least one radical gas stream thereby forming at least one chemical species within at least one compound stream;
   at least one sensor module positioned within the at least one sampling reaction module and configured to measure a change of temperature of the at least one sampling tube due to interaction of the at least one chemical species within the at least one compound stream and the sampling tube and calculate a concentration of the at least one chemical species within the at least one compound stream flowing within the at least on sampling tube based on the measured temperature change of the at least one sampling tube;
   at least one flow measurement module in fluid communication with at least one sampling reaction module, the at least one flow measurement module configured to measure a volume of the at least one of the at least one radical gas stream and at least one compound stream; and
   at least one exhaust conduit configured to exhaust the at least one radical gas stream from the flow measurement module.

2. The system of claim 1 wherein the at least one reagent comprises carbon-based materials.

3. The system of claim 1 wherein the at least one reagent comprises at least one material selected from the group consisting of graphite, silica, carbon fiber, silicon dioxide, and silicon carbide.

4. The system of claim 1 wherein the at least one sampling module includes at least one calorimetry measurement system.

5. The system of claim 1 wherein the at least one sensor module comprises at least one Fourier transform infrared spectroscopy system.

6. The system of claim 1 wherein at least one flow measurement module includes at least one mass flow verifier.

7. The system of claim 1 further comprising at least one processor in communication with at least one of the at least one radical gas generator, at least one sampling module, at least one sensor module, and at least one flow measurement module, the at least one processor configured to controllably adjust to generation of at least one radical gas stream emitted from the at least one radical gas generator based on data received from at least one of the at least one analysis circuit, the at least one sampling module, the at least one sensor module, and the at least one flow measurement module.

* * * * *